(12) United States Patent
Kamath et al.

(10) Patent No.: US 8,774,888 B2
(45) Date of Patent: Jul. 8, 2014

(54) SYSTEM AND METHODS FOR PROCESSING ANALYTE SENSOR DATA

(75) Inventors: Apurv Ullas Kamath, San Diego, CA (US); Paul V. Goode, Jr., Cherry Hill, NJ (US); James H. Brauker, Addison, MI (US); James Patrick Thrower, Oakland, NJ (US)

(73) Assignee: DexCom, Inc., San Diego, CA (US)

( * ) Notice: Subject to any disclaimer, the term of this patent is extended or adjusted under 35 U.S.C. 154(b) by 1202 days.

(21) Appl. No.: 12/690,792

(22) Filed: Jan. 20, 2010

(65) Prior Publication Data

US 2010/0217557 A1  Aug. 26, 2010

Related U.S. Application Data

(62) Division of application No. 10/633,329, filed on Aug. 1, 2003, now Pat. No. 8,060,173.

(51) Int. Cl.
*A61B 5/05* (2006.01)

(52) U.S. Cl.
USPC ............... 600/345; 600/347; 600/365

(58) Field of Classification Search
USPC ........ 600/309, 316, 345–347, 365; 435/4, 14; 436/68; 422/50, 420–429; 204/403.01–403.15; 702/23; 604/64–66; 606/167, 181–183
See application file for complete search history.

(56) References Cited

U.S. PATENT DOCUMENTS

| 3,210,578 | A | 10/1965 | Sherer |
| 3,219,533 | A | 11/1965 | Mullins |
| 3,775,182 | A | 11/1973 | Patton et al. |
| 3,780,727 | A | 12/1973 | King |
| 3,898,984 | A | 8/1975 | Mandel et al. |
| 3,929,971 | A | 12/1975 | Roy |
| 3,943,918 | A | 3/1976 | Lewis |
| 3,964,974 | A | 6/1976 | Banauch et al. |

(Continued)

FOREIGN PATENT DOCUMENTS

| CA | 2127172 | 7/1998 |
| EP | 0 098 592 | 1/1984 |

(Continued)

OTHER PUBLICATIONS

Adilman, Glenn, Videogames: Knowing the Score, Creative Computing, V9, p. 224(5), Dec. 1983, Dialog: File 148, Acc# 01891055.

(Continued)

*Primary Examiner* — Michael D'Angelo
(74) *Attorney, Agent, or Firm* — Knobbe Martens Olson Bear LLP

(57) ABSTRACT

Systems and methods for processing sensor analyte data, including initiating calibration, updating calibration, evaluating clinical acceptability of reference and sensor analyte data, and evaluating the quality of sensor calibration. During initial calibration, the analyte sensor data is evaluated over a period of time to determine stability of the sensor. The sensor may be calibrated using a calibration set of one or more matched sensor and reference analyte data pairs. The calibration may be updated after evaluating the calibration set for best calibration based on inclusion criteria with newly received reference analyte data. Fail-safe mechanisms are provided based on clinical acceptability of reference and analyte data and quality of sensor calibration. Algorithms provide for optimized prospective and retrospective analysis of estimated blood analyte data from an analyte sensor.

34 Claims, 14 Drawing Sheets

(56) References Cited

U.S. PATENT DOCUMENTS

| | | |
|---|---|---|
| 3,979,274 A | 9/1976 | Newman |
| 4,024,312 A | 5/1977 | Korpman |
| 4,076,656 A | 2/1978 | White et al. |
| 4,197,840 A | 4/1980 | Beck et al. |
| 4,215,703 A | 8/1980 | Willson |
| 4,240,889 A | 12/1980 | Yoda et al. |
| 4,253,469 A | 3/1981 | Aslan |
| 4,255,500 A | 3/1981 | Hooke |
| 4,259,540 A | 3/1981 | Sabia |
| 4,374,013 A | 2/1983 | Enfors |
| 4,403,984 A | 9/1983 | Ash et al. |
| 4,415,666 A | 11/1983 | D'Orazio et al. |
| 4,431,004 A | 2/1984 | Bessman et al. |
| 4,436,094 A | 3/1984 | Cerami |
| 4,454,295 A | 6/1984 | Wittmann et al. |
| 4,494,950 A | 1/1985 | Fischell |
| 4,506,680 A | 3/1985 | Stokes |
| RE31,916 E | 6/1985 | Oswin et al. |
| 4,554,927 A | 11/1985 | Fussell |
| 4,577,642 A | 3/1986 | Stokes |
| RE32,361 E | 2/1987 | Duggan |
| 4,655,880 A | 4/1987 | Liu |
| 4,663,824 A | 5/1987 | Kenmochi |
| 4,671,288 A | 6/1987 | Gough |
| 4,680,268 A | 7/1987 | Clark, Jr. |
| 4,703,756 A | 11/1987 | Gough et al. |
| 4,711,251 A | 12/1987 | Stokes |
| 4,721,677 A | 1/1988 | Clark |
| 4,731,726 A | 3/1988 | Allen |
| 4,736,748 A | 4/1988 | Nakamura et al. |
| 4,757,022 A | 7/1988 | Shults et al. |
| 4,759,828 A | 7/1988 | Young et al. |
| 4,781,798 A | 11/1988 | Gough |
| 4,805,625 A | 2/1989 | Wyler |
| 4,849,458 A | 7/1989 | Reed et al. |
| 4,852,573 A | 8/1989 | Kennedy |
| 4,858,615 A | 8/1989 | Meinema |
| 4,871,440 A | 10/1989 | Nagata et al. |
| 4,890,620 A | 1/1990 | Gough |
| 4,890,621 A | 1/1990 | Hakky |
| 4,907,857 A | 3/1990 | Giuliani et al. |
| 4,919,141 A | 4/1990 | Zier et al. |
| 4,927,407 A | 5/1990 | Dorman |
| 4,927,516 A | 5/1990 | Yamaguchi et al. |
| 4,944,299 A | 7/1990 | Silvian |
| 4,953,552 A | 9/1990 | DeMarzo |
| 4,975,636 A | 12/1990 | Desautels |
| 4,986,671 A | 1/1991 | Sun et al. |
| 4,988,341 A | 1/1991 | Columbus et al. |
| 4,994,167 A | 2/1991 | Shults et al. |
| 5,002,572 A | 3/1991 | Picha |
| 5,030,333 A | 7/1991 | Clark, Jr. |
| 5,050,612 A | 9/1991 | Matsumura |
| 5,067,491 A | 11/1991 | Taylor, II et al. |
| 5,068,536 A | 11/1991 | Rosenthal |
| 5,077,476 A | 12/1991 | Rosenthal |
| 5,097,834 A | 3/1992 | Skrabal |
| 5,101,814 A | 4/1992 | Palti |
| 5,108,819 A | 4/1992 | Heller et al. |
| 5,137,028 A | 8/1992 | Nishimura |
| 5,140,985 A | 8/1992 | Schroeder et al. |
| 5,160,418 A | 11/1992 | Mullen |
| 5,165,407 A | 11/1992 | Wilson et al. |
| 5,171,689 A | 12/1992 | Kawaguri et al. |
| 5,190,041 A | 3/1993 | Palti |
| 5,198,771 A | 3/1993 | Fidler et al. |
| 5,208,147 A | 5/1993 | Kagenow et al. |
| 5,243,983 A | 9/1993 | Tarr et al. |
| 5,264,104 A | 11/1993 | Gregg et al. |
| 5,266,179 A | 11/1993 | Nankai et al. |
| 5,269,891 A | 12/1993 | Colin |
| 5,282,848 A | 2/1994 | Schmitt |
| 5,285,513 A | 2/1994 | Kaufman et al. |
| 5,287,753 A | 2/1994 | Routh et al. |
| 5,299,571 A | 4/1994 | Mastrototaro |
| 5,304,468 A | 4/1994 | Phillips et al. |
| 5,310,469 A | 5/1994 | Cunningham et al. |
| 5,312,361 A | 5/1994 | Zadini et al. |
| 5,316,008 A | 5/1994 | Suga et al. |
| 5,324,322 A | 6/1994 | Grill et al. |
| 5,330,521 A | 7/1994 | Cohen |
| 5,330,634 A | 7/1994 | Wong et al. |
| 5,331,555 A | 7/1994 | Hashimoto et al. |
| 5,337,747 A | 8/1994 | Neftel |
| 5,342,409 A | 8/1994 | Mullett |
| 5,343,869 A | 9/1994 | Pross et al. |
| 5,368,224 A | 11/1994 | Richardson et al. |
| 5,372,133 A | 12/1994 | Hogen Esch |
| 5,376,070 A | 12/1994 | Purvis et al. |
| 5,384,028 A | 1/1995 | Ito |
| 5,390,671 A | 2/1995 | Lord et al. |
| 5,391,250 A | 2/1995 | Cheney, II et al. |
| 5,411,647 A | 5/1995 | Johnson et al. |
| 5,411,866 A | 5/1995 | Luong |
| 5,429,735 A | 7/1995 | Johnson et al. |
| 5,431,160 A | 7/1995 | Wilkins |
| 5,434,412 A | 7/1995 | Sodickson et al. |
| 5,448,992 A | 9/1995 | Kuperschmidt |
| 5,462,051 A | 10/1995 | Oka et al. |
| 5,462,064 A | 10/1995 | D'Angelo et al. |
| 5,469,846 A | 11/1995 | Khan |
| 5,474,552 A | 12/1995 | Palti |
| 5,484,404 A | 1/1996 | Schulman et al. |
| 5,491,474 A | 2/1996 | Suni et al. |
| 5,494,562 A | 2/1996 | Maley et al. |
| 5,496,453 A | 3/1996 | Uenoyama et al. |
| 5,497,772 A * | 3/1996 | Schulman et al. ............ 600/347 |
| 5,502,396 A | 3/1996 | Desarzens et al. |
| 5,507,288 A | 4/1996 | Bocker et al. |
| 5,513,636 A | 5/1996 | Palti |
| 5,518,601 A | 5/1996 | Foos et al. |
| 5,531,878 A | 7/1996 | Vadgama et al. |
| 5,540,828 A | 7/1996 | Yacynych |
| 5,553,616 A | 9/1996 | Ham et al. |
| 5,568,806 A | 10/1996 | Cheney, II et al. |
| 5,569,186 A | 10/1996 | Lord et al. |
| 5,571,395 A | 11/1996 | Park et al. |
| 5,575,930 A | 11/1996 | Tietje-Girault et al. |
| 5,582,184 A | 12/1996 | Ericson et al. |
| 5,584,813 A | 12/1996 | Livingston et al. |
| 5,584,876 A | 12/1996 | Bruchman et al. |
| 5,586,553 A | 12/1996 | Halili et al. |
| 5,590,651 A | 1/1997 | Shaffer et al. |
| 5,593,852 A | 1/1997 | Heller et al. |
| 5,624,537 A | 4/1997 | Turner et al. |
| 5,653,863 A | 8/1997 | Genshaw et al. |
| 5,660,163 A | 8/1997 | Schulman et al. |
| 5,683,562 A | 11/1997 | Schaffar et al. |
| 5,686,829 A | 11/1997 | Girault |
| 5,695,623 A | 12/1997 | Michel et al. |
| 5,711,861 A | 1/1998 | Ward et al. |
| 5,730,654 A | 3/1998 | Brown |
| 5,743,262 A | 4/1998 | Lepper, Jr. et al. |
| 5,749,907 A | 5/1998 | Mann |
| 5,779,665 A | 7/1998 | Mastrototaro et al. |
| 5,781,455 A | 7/1998 | Hyodo et al. |
| 5,787,900 A | 8/1998 | Butler et al. |
| 5,791,344 A | 8/1998 | Schulman et al. |
| 5,795,774 A | 8/1998 | Matsumoto et al. |
| 5,800,420 A | 9/1998 | Gross |
| 5,807,247 A | 9/1998 | Merchant et al. |
| 5,807,375 A | 9/1998 | Gross et al. |
| 5,814,599 A | 9/1998 | Mitragotri et al. |
| 5,822,715 A | 10/1998 | Worthington et al. |
| 5,833,603 A | 11/1998 | Kovacs et al. |
| 5,836,887 A | 11/1998 | Oka et al. |
| 5,836,989 A | 11/1998 | Shelton |
| 5,837,728 A | 11/1998 | Purcell |
| 5,840,020 A | 11/1998 | Heinonen et al. |
| 5,851,197 A | 12/1998 | Marano et al. |
| 5,861,019 A | 1/1999 | Sun et al. |
| 5,871,514 A | 2/1999 | Wiklund et al. |
| 5,882,494 A | 3/1999 | Van Antwerp |
| 5,897,578 A | 4/1999 | Wiklund et al. |

(56) References Cited

U.S. PATENT DOCUMENTS

| | | |
|---|---|---|
| 5,899,855 A | 5/1999 | Brown |
| 5,904,708 A | 5/1999 | Goedeke |
| 5,913,998 A | 6/1999 | Butler et al. |
| 5,914,026 A | 6/1999 | Blubaugh, Jr. et al. |
| 5,917,346 A | 6/1999 | Gord |
| 5,919,215 A | 7/1999 | Wiklund et al. |
| 5,928,130 A | 7/1999 | Schmidt |
| 5,928,155 A | 7/1999 | Eggers et al. |
| 5,931,814 A | 8/1999 | Alex et al. |
| 5,933,136 A | 8/1999 | Brown |
| 5,944,661 A | 8/1999 | Swette et al. |
| 5,957,854 A | 9/1999 | Besson et al. |
| 5,957,903 A | 9/1999 | Mirzaee et al. |
| 5,961,451 A | 10/1999 | Reber et al. |
| 5,964,993 A | 10/1999 | Blubaugh et al. |
| 5,965,380 A | 10/1999 | Heller et al. |
| 5,971,922 A | 10/1999 | Arita et al. |
| 5,976,085 A | 11/1999 | Kimball et al. |
| 5,995,860 A | 11/1999 | Sun et al. |
| 5,999,848 A | 12/1999 | Gord et al. |
| 6,001,067 A | 12/1999 | Shults et al. |
| 6,001,471 A | 12/1999 | Bries et al. |
| 6,011,984 A | 1/2000 | Van Antwerp et al. |
| 6,013,113 A | 1/2000 | Mika |
| 6,016,448 A | 1/2000 | Busacker et al. |
| 6,027,445 A | 2/2000 | Von Bahr |
| 6,036,924 A | 3/2000 | Simons et al. |
| 6,049,727 A | 4/2000 | Crothall |
| 6,059,946 A | 5/2000 | Yukawa et al. |
| 6,063,637 A | 5/2000 | Arnold et al. |
| 6,081,735 A | 6/2000 | Diab et al. |
| 6,081,736 A | 6/2000 | Colvin et al. |
| 6,083,523 A | 7/2000 | Dionne et al. |
| 6,083,710 A | 7/2000 | Heller et al. |
| 6,088,608 A | 7/2000 | Schulman et al. |
| 6,091,975 A | 7/2000 | Daddona et al. |
| 6,093,172 A | 7/2000 | Funderburk et al. |
| 6,103,033 A | 8/2000 | Say et al. |
| 6,107,083 A | 8/2000 | Collins et al. |
| 6,115,634 A | 9/2000 | Donders et al. |
| 6,120,676 A | 9/2000 | Heller et al. |
| 6,121,009 A | 9/2000 | Heller et al. |
| 6,122,536 A | 9/2000 | Sun et al. |
| 6,123,827 A | 9/2000 | Wong et al. |
| 6,134,461 A | 10/2000 | Say et al. |
| 6,135,978 A | 10/2000 | Houben et al. |
| 6,144,869 A | 11/2000 | Berner et al. |
| 6,162,611 A | 12/2000 | Heller et al. |
| 6,167,614 B1 | 1/2001 | Tuttle et al. |
| 6,168,568 B1 | 1/2001 | Gavriely |
| 6,175,752 B1 | 1/2001 | Say et al. |
| 6,180,416 B1 | 1/2001 | Kurnik et al. |
| 6,187,062 B1 | 2/2001 | Oweis et al. |
| 6,189,536 B1 | 2/2001 | Martinez et al. |
| 6,201,980 B1 | 3/2001 | Darrow et al. |
| 6,201,993 B1 | 3/2001 | Kruse et al. |
| 6,206,856 B1 | 3/2001 | Mahurkar |
| 6,208,894 B1 | 3/2001 | Schulman et al. |
| 6,212,416 B1 | 4/2001 | Ward et al. |
| 6,212,424 B1 | 4/2001 | Robinson |
| 6,214,185 B1 | 4/2001 | Offenbacher et al. |
| 6,223,083 B1 | 4/2001 | Rosar |
| 6,230,059 B1 | 5/2001 | Duffin |
| 6,233,080 B1 | 5/2001 | Brenner et al. |
| 6,233,471 B1 | 5/2001 | Berner et al. |
| 6,241,863 B1 | 6/2001 | Monbouquette |
| 6,248,067 B1 | 6/2001 | Causey, III et al. |
| 6,256,522 B1 | 7/2001 | Schultz |
| 6,259,937 B1 | 7/2001 | Schulman et al. |
| 6,272,364 B1 | 8/2001 | Kurnik |
| 6,272,480 B1 | 8/2001 | Tresp et al. |
| 6,275,717 B1 | 8/2001 | Gross et al. |
| 6,284,478 B1 | 9/2001 | Heller et al. |
| 6,293,925 B1 | 9/2001 | Safabash et al. |
| 6,299,578 B1 | 10/2001 | Kurnik et al. |
| 6,300,002 B1 | 10/2001 | Webb et al. |
| 6,302,855 B1 | 10/2001 | Knobbe et al. |
| 6,309,351 B1 | 10/2001 | Kurnik et al. |
| 6,309,884 B1 | 10/2001 | Cooper et al. |
| 6,312,388 B1 | 11/2001 | Marcovecchio et al. |
| 6,325,978 B1 | 12/2001 | Labuda et al. |
| 6,325,979 B1 | 12/2001 | Hahn et al. |
| 6,326,160 B1 | 12/2001 | Dunn et al. |
| 6,329,161 B1 | 12/2001 | Heller et al. |
| 6,329,929 B1 | 12/2001 | Weijand et al. |
| 6,330,464 B1 | 12/2001 | Colvin, Jr. et al. |
| 6,343,225 B1 | 1/2002 | Clark, Jr. |
| 6,356,776 B1 | 3/2002 | Berner et al. |
| 6,366,794 B1 | 4/2002 | Moussy et al. |
| 6,368,274 B1 | 4/2002 | Van Antwerp et al. |
| 6,370,941 B2 | 4/2002 | Nakamura |
| 6,379,301 B1 | 4/2002 | Worthington et al. |
| 6,400,974 B1 | 6/2002 | Lesho |
| 6,405,066 B1 | 6/2002 | Essenpreis et al. |
| 6,406,426 B1 | 6/2002 | Reuss et al. |
| 6,409,674 B1 | 6/2002 | Brockway et al. |
| 6,413,393 B1 | 7/2002 | Van Antwerp et al. |
| 6,416,651 B1 | 7/2002 | Miller |
| 6,424,847 B1 | 7/2002 | Mastrototaro et al. |
| 6,447,448 B1 | 9/2002 | Ishikawa et al. |
| 6,454,710 B1 | 9/2002 | Ballerstadt et al. |
| 6,461,496 B1 | 10/2002 | Feldman et al. |
| 6,466,810 B1 | 10/2002 | Ward et al. |
| 6,471,689 B1 | 10/2002 | Joseph et al. |
| 6,475,750 B1 | 11/2002 | Han et al. |
| 6,477,392 B1 | 11/2002 | Honigs et al. |
| 6,477,395 B2 | 11/2002 | Schulman et al. |
| 6,481,440 B2 | 11/2002 | Gielen et al. |
| 6,484,046 B1 | 11/2002 | Say et al. |
| 6,494,830 B1 | 12/2002 | Wessel |
| 6,498,043 B1 | 12/2002 | Schulman et al. |
| 6,510,329 B2 | 1/2003 | Heckel |
| 6,512,939 B1 | 1/2003 | Colvin et al. |
| 6,526,298 B1 | 2/2003 | Khalil et al. |
| 6,527,729 B1 | 3/2003 | Turcott |
| 6,544,212 B2 | 4/2003 | Galley et al. |
| 6,546,268 B1 | 4/2003 | Ishikawa et al. |
| 6,546,269 B1 | 4/2003 | Kurnik |
| 6,547,839 B2 | 4/2003 | Zhang et al. |
| 6,551,496 B1 | 4/2003 | Moles et al. |
| 6,553,241 B2 | 4/2003 | Mannheimer et al. |
| 6,553,244 B2 | 4/2003 | Lesho et al. |
| 6,558,320 B1 * | 5/2003 | Causey et al. ................ 600/300 |
| 6,558,321 B1 | 5/2003 | Burd et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,565,509 B1 | 5/2003 | Say et al. |
| 6,569,521 B1 | 5/2003 | Sheridan et al. |
| 6,572,545 B2 | 6/2003 | Knobbe et al. |
| 6,574,490 B2 | 6/2003 | Abbink et al. |
| 6,575,905 B2 | 6/2003 | Knobbe et al. |
| 6,579,498 B1 | 6/2003 | Eglise |
| 6,579,690 B1 | 6/2003 | Bonnecaze et al. |
| 6,585,644 B2 | 7/2003 | Lebel et al. |
| 6,585,763 B1 | 7/2003 | Keilman et al. |
| 6,589,229 B1 | 7/2003 | Connelly et al. |
| 6,591,125 B1 | 7/2003 | Buse et al. |
| 6,595,919 B2 | 7/2003 | Berner et al. |
| 6,605,072 B2 | 8/2003 | Struys et al. |
| 6,607,509 B2 | 8/2003 | Bobroff et al. |
| 6,613,379 B2 | 9/2003 | Ward et al. |
| 6,618,934 B1 | 9/2003 | Feldman et al. |
| 6,633,772 B2 | 10/2003 | Ford et al. |
| 6,641,533 B2 | 11/2003 | Causey et al. |
| 6,642,015 B2 | 11/2003 | Vachon et al. |
| 6,645,181 B1 | 11/2003 | Lavi et al. |
| 6,648,821 B2 | 11/2003 | Lebel et al. |
| 6,654,625 B1 | 11/2003 | Say et al. |
| 6,673,022 B1 | 1/2004 | Bobo et al. |
| 6,673,596 B1 | 1/2004 | Sayler et al. |
| 6,683,535 B1 | 1/2004 | Utke |
| 6,694,191 B2 | 2/2004 | Starkweather et al. |
| 6,695,860 B1 | 2/2004 | Ward et al. |

(56) References Cited

U.S. PATENT DOCUMENTS

| | | |
|---|---|---|
| 6,699,188 B2 | 3/2004 | Wessel |
| 6,699,218 B2 | 3/2004 | Flaherty et al. |
| 6,702,857 B2 | 3/2004 | Brauker et al. |
| 6,702,972 B1 | 3/2004 | Markle |
| 6,721,587 B2 | 4/2004 | Gough |
| 6,731,976 B2 | 5/2004 | Penn et al. |
| 6,740,075 B2 | 5/2004 | Lebel et al. |
| 6,741,877 B1 | 5/2004 | Shults et al. |
| 6,810,290 B2 | 10/2004 | Lebel et al. |
| 6,869,413 B2 | 3/2005 | Langley et al. |
| 6,892,085 B2 | 5/2005 | McIvor et al. |
| 6,895,263 B2 | 5/2005 | Shin et al. |
| 6,925,393 B1 | 8/2005 | Kalatz et al. |
| 6,931,327 B2 | 8/2005 | Goode et al. |
| 6,952,604 B2 | 10/2005 | DeNuzzio et al. |
| 6,996,427 B2 | 2/2006 | Ali et al. |
| 6,998,247 B2 | 2/2006 | Monfre et al. |
| 7,011,630 B2 | 3/2006 | Desai et al. |
| 7,022,072 B2 | 4/2006 | Fox et al. |
| 7,025,743 B2 | 4/2006 | Mann et al. |
| 7,029,444 B2 | 4/2006 | Shin et al. |
| 7,060,059 B2 | 6/2006 | Keith et al. |
| 7,074,307 B2 | 7/2006 | Simpson et al. |
| 7,098,803 B2 | 8/2006 | Mann et al. |
| 7,108,778 B2 | 9/2006 | Simpson et al. |
| 7,134,999 B2 | 11/2006 | Brauker et al. |
| 7,169,289 B2 | 1/2007 | Schulein et al. |
| 7,192,450 B2 | 3/2007 | Brauker et al. |
| 7,229,288 B2 | 6/2007 | Stuart et al. |
| 7,248,912 B2 | 7/2007 | Gough et al. |
| 7,261,690 B2 | 8/2007 | Teller et al. |
| 7,267,665 B2 | 9/2007 | Steil et al. |
| 7,276,029 B2 | 10/2007 | Goode et al. |
| 7,278,983 B2 | 10/2007 | Ireland et al. |
| 7,295,867 B2 | 11/2007 | Berner et al. |
| 7,354,420 B2 | 4/2008 | Steil et al. |
| 7,359,723 B2 | 4/2008 | Jones |
| 7,402,153 B2 | 7/2008 | Steil et al. |
| 7,417,164 B2 | 8/2008 | Suri |
| 7,426,408 B2 | 9/2008 | DeNuzzio et al. |
| 7,519,408 B2 | 4/2009 | Rasdal et al. |
| 7,519,478 B2 | 4/2009 | Bartkowiak et al. |
| 7,523,004 B2 | 4/2009 | Bartkowiak et al. |
| 7,583,990 B2 | 9/2009 | Goode, Jr. et al. |
| 7,587,287 B2 | 9/2009 | Connolly et al. |
| 7,591,801 B2 | 9/2009 | Brauker et al. |
| 7,599,726 B2 | 10/2009 | Goode, Jr. et al. |
| 7,618,368 B2 | 11/2009 | Brown |
| 7,624,028 B1 | 11/2009 | Brown |
| 7,636,602 B2 | 12/2009 | Baru Fassio et al. |
| 7,640,048 B2 | 12/2009 | Dobbles et al. |
| 7,647,237 B2 | 1/2010 | Malave et al. |
| 7,711,402 B2 | 5/2010 | Shults et al. |
| 7,771,352 B2 | 8/2010 | Shults et al. |
| 7,774,145 B2 | 8/2010 | Brauker et al. |
| 7,792,562 B2 | 9/2010 | Shults et al. |
| 7,826,981 B2 | 11/2010 | Goode et al. |
| 7,914,450 B2 | 3/2011 | Goode et al. |
| 7,925,321 B2 | 4/2011 | Goode et al. |
| 7,933,639 B2 | 4/2011 | Goode et al. |
| 7,955,261 B2 | 6/2011 | Goode et al. |
| 7,959,569 B2 | 6/2011 | Goode et al. |
| 7,979,104 B2 | 7/2011 | Kamath et al. |
| 7,986,986 B2 | 7/2011 | Goode et al. |
| 8,206,297 B2 | 6/2012 | Kamath et al. |
| 8,290,562 B2 | 10/2012 | Goode et al. |
| 8,332,008 B2 | 12/2012 | Goode et al. |
| 8,369,919 B2 | 2/2013 | Kamath et al. |
| 8,428,679 B2 | 4/2013 | Goode, Jr. et al. |
| 8,548,553 B2 | 10/2013 | Kamath et al. |
| 2001/0016682 A1 | 8/2001 | Berner et al. |
| 2001/0041830 A1 | 11/2001 | Varalli et al. |
| 2001/0051768 A1 | 12/2001 | Schulman et al. |
| 2002/0019022 A1 | 2/2002 | Dunn et al. |
| 2002/0026111 A1 | 2/2002 | Ackerman |
| 2002/0042090 A1 | 4/2002 | Heller et al. |
| 2002/0042561 A1 | 4/2002 | Schulman et al. |
| 2002/0045808 A1 | 4/2002 | Ford et al. |
| 2002/0065453 A1 | 5/2002 | Lesho et al. |
| 2002/0068860 A1 | 6/2002 | Clark, Jr. |
| 2002/0099282 A1 | 7/2002 | Knobbe et al. |
| 2002/0106709 A1 | 8/2002 | Potts et al. |
| 2002/0111547 A1 | 8/2002 | Knobbe et al. |
| 2002/0119711 A1 | 8/2002 | Van Antwerp et al. |
| 2002/0155615 A1 | 10/2002 | Novikov et al. |
| 2002/0161288 A1* | 10/2002 | Shin et al. ............ 600/316 |
| 2002/0198513 A1 | 12/2002 | Lebel et al. |
| 2003/0004457 A1 | 1/2003 | Andersson |
| 2003/0006669 A1 | 1/2003 | Pei et al. |
| 2003/0023171 A1 | 1/2003 | Sato et al. |
| 2003/0023317 A1 | 1/2003 | Brauker et al. |
| 2003/0028089 A1 | 2/2003 | Galley et al. |
| 2003/0032874 A1 | 2/2003 | Rhodes et al. |
| 2003/0050537 A1 | 3/2003 | Wessel |
| 2003/0050546 A1 | 3/2003 | Desai et al. |
| 2003/0060692 A1 | 3/2003 | Ruchti et al. |
| 2003/0060765 A1 | 3/2003 | Campbell et al. |
| 2003/0070548 A1 | 4/2003 | Clausen |
| 2003/0076082 A1 | 4/2003 | Morgan et al. |
| 2003/0078481 A1 | 4/2003 | McIvor et al. |
| 2003/0078560 A1 | 4/2003 | Miller et al. |
| 2003/0097082 A1 | 5/2003 | Purdy et al. |
| 2003/0100821 A1 | 5/2003 | Heller et al. |
| 2003/0117296 A1 | 6/2003 | Seely |
| 2003/0125612 A1 | 7/2003 | Fox et al. |
| 2003/0125613 A1 | 7/2003 | Enegren et al. |
| 2003/0130616 A1 | 7/2003 | Steil et al. |
| 2003/0134347 A1 | 7/2003 | Heller et al. |
| 2003/0187338 A1 | 10/2003 | Say et al. |
| 2003/0188427 A1 | 10/2003 | Say et al. |
| 2003/0199744 A1 | 10/2003 | Buse et al. |
| 2003/0208113 A1 | 11/2003 | Mault et al. |
| 2003/0211625 A1 | 11/2003 | Cohan |
| 2003/0212317 A1 | 11/2003 | Kovatchev et al. |
| 2003/0212346 A1 | 11/2003 | Yuzhakov et al. |
| 2003/0212347 A1 | 11/2003 | Sohrab |
| 2003/0217966 A1 | 11/2003 | Tapsak et al. |
| 2003/0225437 A1 | 12/2003 | Ferguson |
| 2003/0235817 A1* | 12/2003 | Bartkowiak et al. ........... 435/5 |
| 2004/0010207 A1 | 1/2004 | Flaherty et al. |
| 2004/0011671 A1 | 1/2004 | Shults et al. |
| 2004/0015063 A1 | 1/2004 | DeNuzzio et al. |
| 2004/0015134 A1 | 1/2004 | Lavi et al. |
| 2004/0024327 A1 | 2/2004 | Brodnick |
| 2004/0030285 A1 | 2/2004 | Lavi et al. |
| 2004/0030294 A1 | 2/2004 | Mahurkar |
| 2004/0039298 A1 | 2/2004 | Abreu |
| 2004/0039406 A1 | 2/2004 | Jessen |
| 2004/0045879 A1 | 3/2004 | Shults et al. |
| 2004/0068230 A1 | 4/2004 | Estes et al. |
| 2004/0078219 A1 | 4/2004 | Kaylor |
| 2004/0106857 A1 | 6/2004 | Gough |
| 2004/0143173 A1 | 7/2004 | Reghabi et al. |
| 2004/0152187 A1 | 8/2004 | Haight et al. |
| 2004/0152622 A1 | 8/2004 | Keith et al. |
| 2004/0167801 A1 | 8/2004 | Say et al. |
| 2004/0186362 A1 | 9/2004 | Brauker et al. |
| 2004/0186365 A1 | 9/2004 | Jin et al. |
| 2004/0199059 A1 | 10/2004 | Brauker et al. |
| 2004/0219664 A1 | 11/2004 | Heller et al. |
| 2005/0010265 A1 | 1/2005 | Baru Fassio et al. |
| 2005/0027180 A1 | 2/2005 | Goode et al. |
| 2005/0027181 A1 | 2/2005 | Goode et al. |
| 2005/0027182 A1 | 2/2005 | Siddiqui et al. |
| 2005/0027462 A1 | 2/2005 | Goode et al. |
| 2005/0027463 A1 | 2/2005 | Goode et al. |
| 2005/0031689 A1 | 2/2005 | Shults et al. |
| 2005/0033132 A1 | 2/2005 | Shults et al. |
| 2005/0043598 A1 | 2/2005 | Goode et al. |
| 2005/0051427 A1 | 3/2005 | Brauker et al. |
| 2005/0051440 A1 | 3/2005 | Simpson et al. |
| 2005/0054909 A1 | 3/2005 | Petisce et al. |
| 2005/0056552 A1 | 3/2005 | Simpson et al. |
| 2005/0090607 A1 | 4/2005 | Tapsak et al. |

(56) References Cited

U.S. PATENT DOCUMENTS

| | | |
|---|---|---|
| 2005/0096519 A1 | 5/2005 | DeNuzzio et al. |
| 2005/0101847 A1 | 5/2005 | Routt et al. |
| 2005/0113653 A1 | 5/2005 | Fox et al. |
| 2005/0115832 A1 | 6/2005 | Simpson et al. |
| 2005/0121322 A1 | 6/2005 | Say |
| 2005/0139489 A1 | 6/2005 | Oliver et al. |
| 2005/0143635 A1 | 6/2005 | Kamath et al. |
| 2005/0143675 A1 | 6/2005 | Neel et al. |
| 2005/0154271 A1 | 7/2005 | Rasdal et al. |
| 2005/0187720 A1 | 8/2005 | Goode et al. |
| 2005/0192557 A1 | 9/2005 | Brauker et al. |
| 2005/0203360 A1 | 9/2005 | Brauker et al. |
| 2005/0211571 A1 | 9/2005 | Schulein et al. |
| 2005/0215872 A1 | 9/2005 | Berner et al. |
| 2005/0239154 A1 | 10/2005 | Feldman et al. |
| 2005/0242479 A1 | 11/2005 | Petisce et al. |
| 2005/0245795 A1 | 11/2005 | Goode et al. |
| 2005/0245799 A1 | 11/2005 | Brauker et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0040402 A1 | 2/2006 | Brauker et al. |
| 2006/0100588 A1 | 5/2006 | Brunnberg et al. |
| 2006/0183984 A1 | 8/2006 | Dobbles et al. |
| 2006/0183985 A1 | 8/2006 | Brister et al. |
| 2006/0222566 A1 | 10/2006 | Brauker et al. |
| 2006/0258929 A1 | 11/2006 | Goode et al. |
| 2006/0281985 A1 | 12/2006 | Ward et al. |
| 2007/0016381 A1 | 1/2007 | Kamath et al. |
| 2007/0032706 A1 | 2/2007 | Kamath et al. |
| 2007/0049873 A1 | 3/2007 | Hansen et al. |
| 2007/0066873 A1 | 3/2007 | Kamath et al. |
| 2007/0203410 A1 | 8/2007 | Say et al. |
| 2007/0203966 A1 | 8/2007 | Brauker et al. |
| 2007/0208244 A1 | 9/2007 | Brauker et al. |
| 2007/0208245 A1 | 9/2007 | Brauker et al. |
| 2007/0208246 A1 | 9/2007 | Brauker et al. |
| 2007/0213610 A1 | 9/2007 | Say et al. |
| 2007/0232876 A1 | 10/2007 | Otto et al. |
| 2008/0021666 A1 | 1/2008 | Goode et al. |
| 2008/0033254 A1 | 2/2008 | Kamath et al. |
| 2008/0071157 A1 | 3/2008 | Mcgarraugh et al. |
| 2008/0071158 A1 | 3/2008 | Mcgarraugh et al. |
| 2008/0072663 A1 | 3/2008 | Keenan et al. |
| 2008/0183061 A1 | 7/2008 | Goode et al. |
| 2008/0183399 A1 | 7/2008 | Goode et al. |
| 2008/0187655 A1 | 8/2008 | Markle et al. |
| 2008/0188722 A1 | 8/2008 | Markle et al. |
| 2008/0188725 A1 | 8/2008 | Markle et al. |
| 2008/0189051 A1 | 8/2008 | Goode et al. |
| 2008/0193936 A1 | 8/2008 | Goode et al. |
| 2008/0194937 A1 | 8/2008 | Goode et al. |
| 2008/0195967 A1 | 8/2008 | Goode et al. |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0305009 A1 | 12/2008 | Gamsey et al. |
| 2008/0305506 A1 | 12/2008 | Suri |
| 2008/0306368 A1 | 12/2008 | Goode et al. |
| 2008/0306433 A1 | 12/2008 | Dobbles et al. |
| 2008/0306435 A1 | 12/2008 | Kamath et al. |
| 2008/0306444 A1 | 12/2008 | Brister et al. |
| 2009/0005666 A1 | 1/2009 | Shin et al. |
| 2009/0012379 A1 | 1/2009 | Goode et al. |
| 2009/0018418 A1 | 1/2009 | Markle et al. |
| 2009/0018426 A1 | 1/2009 | Markle et al. |
| 2009/0036758 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0061528 A1 | 3/2009 | Suri |
| 2009/0062645 A1 | 3/2009 | Brauker et al. |
| 2009/0076361 A1 | 3/2009 | Kamath et al. |
| 2009/0081803 A1 | 3/2009 | Gamsey et al. |
| 2009/0124877 A1 | 5/2009 | Goode, Jr. et al. |
| 2009/0124878 A1 | 5/2009 | Goode, Jr. et al. |
| 2009/0156924 A1 | 6/2009 | Shariati et al. |
| 2009/0177058 A1 | 7/2009 | Say et al. |
| 2009/0177059 A1 | 7/2009 | Say et al. |
| 2009/0177060 A1 | 7/2009 | Say et al. |
| 2009/0177143 A1 | 7/2009 | Markle et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0203981 A1 | 8/2009 | Brauker et al. |
| 2009/0204341 A1 | 8/2009 | Brauker et al. |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247857 A1 | 10/2009 | Harper et al. |
| 2009/0264719 A1 | 10/2009 | Markle et al. |
| 2009/0264856 A1 | 10/2009 | Lebel et al. |
| 2009/0287074 A1 | 11/2009 | Shults et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0022855 A1 | 1/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036224 A1 | 2/2010 | Goode, Jr. et al. |
| 2010/0036225 A1 | 2/2010 | Goode, Jr. et al. |
| 2010/0045465 A1 | 2/2010 | Brauker et al. |
| 2010/0081908 A1 | 4/2010 | Dobbles et al. |
| 2010/0161269 A1 | 6/2010 | Kamath et al. |
| 2010/0174158 A1 | 7/2010 | Kamath et al. |
| 2010/0174167 A1 | 7/2010 | Kamath et al. |
| 2010/0174168 A1 | 7/2010 | Goode et al. |
| 2010/0179399 A1 | 7/2010 | Goode et al. |
| 2010/0179405 A1 | 7/2010 | Goode et al. |
| 2010/0179406 A1 | 7/2010 | Goode et al. |
| 2010/0185065 A1 | 7/2010 | Goode et al. |
| 2010/0185072 A1 | 7/2010 | Goode et al. |
| 2010/0185073 A1 | 7/2010 | Goode et al. |
| 2010/0185074 A1 | 7/2010 | Goode et al. |
| 2010/0204555 A1 | 8/2010 | Shults et al. |
| 2010/0214104 A1 | 8/2010 | Goode et al. |
| 2010/0217106 A1 | 8/2010 | Goode et al. |
| 2010/0217555 A1 | 8/2010 | Goode, Jr. et al. |
| 2010/0217557 A1 | 8/2010 | Goode, Jr. et al. |
| 2010/0234796 A1 | 9/2010 | Kamath et al. |
| 2011/0231141 A1 | 9/2011 | Goode, Jr. et al. |
| 2012/0209098 A1 | 8/2012 | Goode et al. |

(56) References Cited

U.S. PATENT DOCUMENTS

| | | | |
|---|---|---|---|
| 2012/0215461 A1 | 8/2012 | Goode et al. | |
| 2012/0215462 A1 | 8/2012 | Goode et al. | |
| 2012/0283541 A1 | 11/2012 | Kamath et al. | |

FOREIGN PATENT DOCUMENTS

| | | | |
|---|---|---|---|
| EP | 0 107 634 | | 5/1984 |
| EP | 0 127 958 | | 12/1984 |
| EP | 0 286 118 | | 10/1988 |
| EP | 0 288 793 | | 11/1988 |
| EP | 0 320 109 | | 6/1989 |
| EP | 0 352 610 | | 1/1990 |
| EP | 0 352 631 | | 1/1990 |
| EP | 0 353 328 | | 2/1990 |
| EP | 0 390 390 | | 10/1990 |
| EP | 0 406 473 | | 1/1991 |
| EP | 0 440 044 | | 8/1991 |
| EP | 0 441 252 | | 8/1991 |
| EP | 0 467 078 | | 1/1992 |
| EP | 0 534 074 | | 3/1993 |
| EP | 0 563 795 | | 10/1993 |
| EP | 0 323 605 | | 1/1994 |
| EP | 0 647 849 | | 4/1995 |
| EP | 0 424 633 | | 1/1996 |
| EP | 0 776 628 | | 6/1997 |
| EP | 0 817 809 | | 1/1998 |
| EP | 0 838 230 | | 4/1998 |
| EP | 0 880 936 | | 12/1998 |
| EP | 0 885 932 | | 12/1998 |
| EP | 0 995 805 | | 4/2000 |
| EP | 1 077 634 | | 2/2001 |
| EP | 1 078 258 | | 2/2001 |
| EP | 1 153 571 | | 11/2001 |
| EP | 2 226 086 | | 8/2010 |
| EP | 2 223 710 | | 9/2010 |
| FR | 2656423 | | 6/1991 |
| FR | 2760962 | | 9/1998 |
| GB | 1 442 303 | | 7/1976 |
| GB | 2149918 | | 6/1985 |
| GB | 2153535 | A * | 8/1985 |
| JP | 62083849 | | 4/1997 |
| JP | 11153575 | | 6/1999 |
| JP | 11192886 | A | 7/1999 |
| JP | 2000-060826 | | 2/2000 |
| JP | 2002513602 | | 5/2002 |
| JP | 2003-108679 | | 4/2003 |
| WO | WO 89/02720 | | 4/1989 |
| WO | WO 90/00738 | | 1/1990 |
| WO | WO 90/10861 | | 9/1990 |
| WO | WO 92/13271 | | 8/1992 |
| WO | WO 93/14693 | | 8/1993 |
| WO | WO 94/22367 | | 10/1994 |
| WO | WO 95/07109 | | 3/1995 |
| WO | WO 96/14026 | | 5/1996 |
| WO | WO 96/25089 | | 8/1996 |
| WO | WO 96/30431 | | 10/1996 |
| WO | WO 97/01986 | | 1/1997 |
| WO | WO 97/28737 | | 8/1997 |
| WO | WO 97/38625 | | 10/1997 |
| WO | WO 97/43633 | | 11/1997 |
| WO | WO 98/24358 | | 6/1998 |
| WO | WO 99/56613 | | 4/1999 |
| WO | WO 99/48419 | | 9/1999 |
| WO | WO 99/58051 | | 11/1999 |
| WO | WO 99/58973 | | 11/1999 |
| WO | WO 00/12720 | | 3/2000 |
| WO | WO 00/13002 | | 3/2000 |
| WO | WO 00/13003 | | 3/2000 |
| WO | WO 00/19887 | | 4/2000 |
| WO | WO 00/32098 | | 6/2000 |
| WO | WO 00/33065 | | 6/2000 |
| WO | WO 00/49941 | | 8/2000 |
| WO | WO 00/59373 | | 10/2000 |
| WO | WO 00/74753 | | 12/2000 |
| WO | WO 00/78210 | | 12/2000 |
| WO | WO 01/12158 | | 2/2001 |
| WO | WO 01/16579 | | 3/2001 |
| WO | WO 01/20019 | | 3/2001 |
| WO | WO 01/20334 | | 3/2001 |
| WO | WO 01/34243 | | 5/2001 |
| WO | WO 01/43660 | | 6/2001 |
| WO | WO 01/52727 | | 7/2001 |
| WO | WO 01/58348 | | 8/2001 |
| WO | WO 01/68901 | | 9/2001 |
| WO | WO 01/69222 | | 9/2001 |
| WO | WO 01/88524 | | 11/2001 |
| WO | WO 01/88534 | | 11/2001 |
| WO | WO 02/05702 | | 1/2002 |
| WO | WO 02/24065 | | 3/2002 |
| WO | WO 02/082989 | | 10/2002 |
| WO | WO 02/089666 | | 11/2002 |
| WO | WO 02/100266 | | 12/2002 |
| WO | WO 03/016882 | | 2/2003 |
| WO | WO 03/101862 | | 12/2003 |
| WO | WO 2004/110256 | | 12/2004 |
| WO | WO 2005/011489 | | 2/2005 |
| WO | WO 2005/012873 | | 2/2005 |
| WO | WO 2005/032400 | | 4/2005 |
| WO | WO 2005/057168 | | 6/2005 |
| WO | WO 2005/057175 | | 6/2005 |
| WO | WO 2005/026689 | | 10/2005 |
| WO | WO 2006/050405 | | 5/2006 |
| WO | WO 2006/105146 | | 10/2006 |
| WO | WO 2006/118713 | | 11/2006 |
| WO | WO 2006/131288 | | 12/2006 |
| WO | WO 2007/002579 | | 1/2007 |
| WO | WO 2007/065285 | | 6/2007 |
| WO | WO 2007/114943 | | 10/2007 |
| WO | WO 2007/127606 | | 11/2007 |
| WO | WO 2007/143225 | | 12/2007 |
| WO | WO 2008/076868 | | 6/2008 |

OTHER PUBLICATIONS

Clarke et al. Sep.-Oct. 1987. Evaluating Clinical Accuracy of Systems for Self-Monitoring of Blood Glucose. Diabetes Care 10(5):622-628.

Currie et al., Novel non-intrusive trans-dermal remote wireless micro-fluidic monitoring systme applied to continuous glucose and lactate assays for casualty care and combat readiness assessment, RTO HFM Symposium, St. Pete Beach, RTO-MP-HFM-109, Aug. 16-18, 2004, 18 pp.

Davies, et al. 1992. Polymer membranes in clinical sensor applications. I. An overview of membrane function, Biomaterials, 13(14):971-978.

Diabetes Educational Video Game Recognized by Software Publishers Association, Press Release, Novo Nordisk, Mar. 14, 1994.

Freiberger, Paul, Video Game Takes on Diabetes Superhero 'Captain Novolin' Offers Treatment Tips, San Francisco Examiner, Jun. 26, 1992, Fourth Edition, Business Sec. B1.

Guerci et al., 2003. Clinical performance of CGMS in type 1 diabetic patents treated by continuous subcutaneous insulin infusion using insulin analogs, Diabetes Care, 26:582-589.

Jaffari et al. 1995. Recent advances in amperometric glucose biosensors for in vivo monitoring, Physiol. Meas. 16: 1-15.

Jeutter et al. 1993. Design of a radio-linked implantable cochlear prosthesis using surface acoustic wave devices. IEEE Transactions on ultrasonics, ferroelectrics and frequency control 40(5):469-477.

Jobst et al., (1996) Thin-Film Microbiosensors for Glucose-Lactate Monitoring, Anal Chem. 8(18): 3173-3179.

Kovatchev et al. Aug. 2004. Evaluating the accuracy of continuous glucose-monitoring sensors: continuous glucose-error grid analysis illustrated by TheraSense Freestyle Navigator data. Diabetes Care 27(8):1922-1928.

Matsuki. 1994. Energy transfer system utilizing amorphous wires for implantable medical devices. IEEE Transactions on Magnetics 31(2):1276-1282.

Mazzola et al., Video Diabetes: A Teaching Tool for Children with Insulin-Dependent Diabetes, Proceedings—7th Annual Symposium

(56) References Cited

OTHER PUBLICATIONS on Computer Applications in Medical Care; Washington, D.C.; Dialog:, (Oct. 1983), File 8, Acc# 01624462.
Miller et al. 1993. Development of an autotuned transcutaneous energy transfer system ASAIO Journal 39:M706-M710.
Moussy et al. 1993. Performance of subcutaneously implanted needle-type glucose sensors employing a novel trilayer coating, Anal Chem. 85: 2072-2077.
Moussy, Francis (Nov. 2002) Implantable Glucose Sensor: Progress and Problems, Sensors, 1:270-273.
Murphy, et al. 1992. Polymer membranes in clinical sensor applications. II. The design and fabrication of permselective hydrogels for electrochemical devices, Biomaterials, 13(14):979-990.
Nintendo Healthcare, Wired, Dec. 1993.
Raya Systems Pioneers Healthy Video Games, PlayRight, Nov. 1993 (pp. 14-15).
Samuels, M.P. 2004. The effects of flight and altitude. Arch Dis Child. 89: 448-455.
Smith et al. 1998. An externally powered, multichannel, implantable stimulator-telemeter for control of paralyzed muscle. IEEE Transactions on Biomedical Engineering 45(4):463-475.
Thijssen et al. 1984. A Kalman Filter for Calibration, Evaluation of Unknown Samples and Quality Control in Drifting Systems, Part 1. Theory and Simulations, Anal Chim Acta 156: 87-101.
Thijssen et al. 1985. A Kalman Filter for Calibration, Evaluation of Unknown Samples and Quality Control in Drifting Systems, Part 3. Variance Reduction, Anal Chim Acta. 173: 265-272.
Thijssen et al. 1985. A Kalman Filter for Calibration, Evaluation of Unknown Samples and Quality Control in Drifting Systems, Part 4. Flow Injection Analysis, Anal Chim Acta. 174: 27-40.
Thijssen, P.C. 1984. A Kalman Filder for Calibration, Evaluation of Unknown Samples and Quality Control in Drifting Systems, Part 2. Optimal Designs, Anal Chim Acta. 162: 253-262.
U.S. Appl. No. 09/447,227, filed Nov. 22, 1999.
Ward et al. 2004. A wire-based dual-analyte sensor for Glucose and Lactate: In Vitro and In Vivo Evaluation, Diab Tech Therapeut. 6(3): 389-401.
Electronic File History of Inter Partes Reexamination Control No. 95/001,039, filed Apr. 17, 2008 containing Office Action(s) dated May 29, 2008, Aug. 14, 2009, and Dec. 24, 2009 and May 3, 2011, 3rd Party/Requester Submissions dated Aug. 27, 2008, Nov. 13, 2009, Feb. 4, 2010, and May 3, 2010 and Applicant Respons(es) filed Jul. 29, 2008, Oct. 14, 2009, Jan. 21, 2010, Apr. 2, 2010 and May 5, 2010 as of May 3, 2011.
Electronic File History of Inter Partes Reexamination Control No. 95/001,038, filed Apr. 17, 2008 containing Office Action(s) dated Apr. 25, 2008, Jun. 17, 2008, Feb. 14, 2009, Jun. 19, 2009, Mar. 18, 2010, May 28, 2010, Aug. 13, 2010, Sep. 3, 2010, Sep. 17, 2010 and May 4, 2011, and Applicant(s) Responses filed Aug. 18, 2008, Oct. 19, 2009, Apr. 16, 2010, Jul. 28, 2010 and Third Party/Appellant Submissions of Sep. 16, 2008, Jul. 17, 2009, Sep. 17, 2009, Jun. 28, 2010, Oct. 8, 2010 as of May 5, 2011.
Aalders et al. 1991. Development of a wearable glucose sensor; studies in healthy volunteers and in diabetic patients. The International Journal of Artificial Organs 14(2):102-108.
Abe et al. 1992. Characterization of glucose microsensors for intracellular measurements. Anal. Chem. 64(18):2160-2163.
Abel et al. 1984. Experience with an implantable glucose sensor as a prerequisite of an artificial beta cell, Biomed. Biochim. Acta 43(5):577-584.
Abel et al. 2002. Biosensors for in vivo glucose measurement: can we cross the experimental stage. Biosens Bioelectron 17:1059-1070.
Alcock & Turner. 1994. Continuous Analyte Monitoring to Aid Clinical Practice. IEEE Engineering in Med. & Biol. Mag. 13:319-325.
American Heritage Dictionary, 4th Edition. 2000. Houghton Mifflin Company, p. 82.
Amin et al. 2003. Hypoglycemia prevalence in prepubertal children with type 1 diabetes on standard insulin regimen: Use of continuous glucose monitoring system. Diabetes Care 26(3):662-667.

Answers.com. "xenogenic." The American Heritage Stedman's Medical Dictionary. Houghton Mifflin Company, 2002. Answers. com Nov. 7, 2006 http://www. Answers.com/topic/xenogenic.
Armour et al. Dec. 1990. Application of Chronic Intravascular Blood Glucose Sensor in Dogs. Diabetes 39:1519-1526.
Atanasov et al. 1994. Biosensor for continuous glucose monitoring. Biotechnology and Bioengineering 43:262-266.
Atanasov et al. 1997. Implantation of a refillable glucose monitoring-telemetry device. Biosens Bioelectron 12:669-680.
Aussedat et al. 1997. A user-friendly method for calibrating a subcutaneous glucose sensor-based hypoglycaemic alarm. Biosensors & Bioelectronics 12(11):1061-1071.
Bailey et al. 2007. Reduction in hemoglobin A1c with real-time continuous glucose monitoring: results from a 12-week observational study. Diabetes Technology & Therapeutics 9(3):203-210.
Baker et al. 1993. Dynamic concentration challenges for biosensor characterization. Biosensors & Bioelectronics 8:433-441.
Baker et al. 1996. Dynamic delay and maximal dynamic error in continuous biosensors. Anal Chem 68(8):1292-1297.
Bani Amer, M. M. 2002. An accurate amperometric glucose sensor based glucometer with eliminated cross-sensitivity. J Med Eng Technol 26(5):208-213.
Bard et al. 1980. Electrochemical Methods. John Wiley & Sons, pp. 173-175.
Beach et al. 1999. Subminiature implantable potentiostat and modified commercial telemetry device for remote glucose monitoring. IEEE Transactions on Instrumentation and Measurement 48(6):1239-1245.
Bellucci et al. Jan. 1986. Electrochemical behaviour of graphite-epoxy composite materials (GECM) in aqueous salt solutions, Journal of Applied Electrochemistry, 16(1):15-22.
Bessman et al., Progress toward a glucose sensor for the artificial pancreas, Proceedings of a Workshop on Ion-Selective Microelectrodes, Jun. 4-5, 1973, Boston, MA, 189-197.
Biermann et al. 2008. How would patients behave if they were continually informed of their blood glucose levels? A simulation study using a "virtual" patient. Diab. Thechnol. & Therapeut., 10:178-187.
Bindra et al. 1989. Pulsed amperometric detection of glucose in biological fluids at a surface-modified gold electrode. Anal Chem 61:2566-2570.
Bindra et al. 1991. Design and In Vitro Studies of a Needle-Type Glucose Senso for Subcutaneous Monitoring. Anal. Chem 63:1692-96.
Bisenberger et al. 1995. A triple-step potential waveform at enzyme multisensors with thick-film gold electrodes for detection of glucose and sucrose. Sensors and Actuators, B 28:181-189.
Bland et al. 1986. Statistical methods for assessing agreement between two methods of clinical measurement. Lancet 1:307-310.
Bland et al. 1990. A note on the use of the intraclass correlation coefficient in the evaluation of agreement between two methods of measurement. Comput. Biol. Med. 20(5):337-340.
Bobbioni-Harsch et al. 1993. Lifespan of subcutaneous glucose sensors and their performances during dynamic glycaemia changes in rats, J. Biomed. Eng. 15:457-463.
Bode et al. 1999. Continuous glucose monitoring used to adjust diabetes therapy improves glycosylated hemoglobin: A pilot study. Diabetes Research and Clinical Practice 46:183-190.
Bode et al. 2000. Using the continuous glucose monitoring system to improve the management of type 1 diabetes. Diabetes Technology & Therapeutics, 2(Suppl 1):S43-48.
Bode, B. W. 2000. Clinical utility of the continuous glucose monitoring system. Diabetes Technol Ther, 2(Suppl 1):S35-41.
Boedeker Plastics, Inc. 2009. Polyethylene Specifications Data Sheet, http://www.boedeker.com/polye_p.htm [Aug. 19, 2009 3:36:33 PM].
Boland et al. 2001. Limitations of conventional methods of self-monitoring of blood glucose. Diabetes Care 24(11):1858-1862.
Bolinder et al. 1992. Microdialysis measurement of the absolute glucose concentration in subcutaneous adipose tissue allowing glucose monitoring in diabetic patients. Diabetologia 35:1177-1180.
Bolinder et al. 1997. Self-monitoring of blood glucose in type 1 diabetic patients: Comparison with continuous microdialysis mea-

(56) References Cited

OTHER PUBLICATIONS surements of glucose in subcutaneous adipose tissue during ordinary life conditions. Diabetes Care 20(1):64-70.
Bott, A. W. 1997. A Comparison of Cyclic Voltammetry and Cyclic Staircase Voltammetry Current Separations 16:1, 23-26.
Bott, A. 1998. Electrochemical methods for the determination of glucose. Current Separations 17(1):25-31.
Bowman, L.; Meindl, J. D. 1986. The packaging of implantable integrated sensors. IEEE Trans Biomed Eng BME33(2):248-255.
Brauker et al. Jun. 27, 1996. Local Inflammatory Response Around Diffusion Chambers Containing Xenografts Transplantation 61(12):1671-1677.
Braunwald, 2008. Biomarkers in heart failure. *N. Engl. J. Med.*, 358: 2148-2159.
Bremer et al. 1999. Is blood glucose predictable from previous values? A solicitation for data. Diabetes 48:445-451.
Bremer et al. 2001. Benchmark data from the literature for evaluation of new glucose sensing technologies. Diabetes Technology & Therapeutics 3(3):409-418.
Brooks et al. "Development of an on-line glucose sensor for fermentation monitoring," Biosensors, 3:45-56 (1987/88).
Bruckel et al. 1989. In vivo measurement of subcutaneous glucose concentrations with an enzymatic glucose sensor and a wick method. Klin Wochenschr 67:491-495.
Brunstein et al. 1989. Preparation and validation of implantable electrodes for the measurement of oxygen and glucose. Biomed Biochim. Acta 48(11/12):911-917.
Cai et al. 2004. A wireless, remote query glucose biosensor based on a pH-sensitive polymer. Anal Chem 76(4):4038-4043.
Cameron et al. 1997. Micromodular Implants to provide electrical stimulation of paralyzed muscles and limbs. IEEE Transactions on Biomedical Engineering 44(9):781-790.
Campanella et al. 1993. Biosensor for direct determination of glucose and lactate in undiluted biological fluids. Biosensors & Bioelectronics 8:307-314.
Candas et al (1994). "An adaptive plasma glucose controller basedon on a nonlinear insulin/glucose model." *IEEE Transactions on Biomedical Engineering*, 41(2): 116-124.
Cass et al. "Ferrocene-mediated enzyme electrodes for amperometric determination of glucose," Anal. Chem., 36:667-71 (1984).
Cassidy et al., Apr. 1993. Novel electrochemical device for the detection of cholesterol or glucose, Analyst, 118:415-418.
Chase et al. 2001. Continuous subcutaneous glucose monitoring in children with type 1 diabetes. Pediatrics 107:222-226.
Chen et al. 2002. Defining the period of recovery of the glucose concentration after its local perturbation by the implantation of a miniature sensor. Clin. Chem. Lab. Med. 40:786-789.
Chia et al. 2004. Glucose sensors: toward closed loop insulin delivery. Endocrinol Metab Clin North Am 33:175-95.
Choleau et al. 2002. Calibration of a subcutaneous amperometric glucose sensor implanted for 7 days in diabetic patients. Part 2. Superiority of the one-point calibration method. Biosensors and Bioelectronics 17:647-654.
Ciba® Irgacure 2959 Photoinitiator Product Description, Ciba Specialty Chemicals Inc., Basel, Switzerland.
Claremont et al. 1986. Subcutaneous implantation of a ferrocene-mediated glucose sensor in pigs. Diabetologia 29:817-821.
Claremont et al. Jul. 1986. Potentially-implntable, ferrocene-mediated glucose sensor. J. Biomed. Eng. 8:272-274.
Clark et al., 1981. One-minute electrochemical enzymic assay for cholesterol in biological materials, Clin. Chem. 27(12):1978-1982.
Clark et al. 1987. Configurational cyclic voltammetry: increasing the specificity and reliablity of implanted electrodes, IEEE/Ninth Annual Conference of the Engineering in Medicine and Biology Society, pp. 0782-0783.
Clark et al. 1988. Long-term stability of electroenzymatic glucose sensors implanted in mice. Trans Am Soc Artif Intern Organs 34:259-265.
CLSI. Performance metrics for continuous interstitial glucose monitoring; approved guideline, CLSI document POCT05-A. Wayne, PA: Clinical and Laboratory Standards Institute: 2008 28(33), 72 pp.
Colangelo et al. 1967. Corrosion rate measurements in vivo, Journal of Biomedical Materials Research, 1:405-414.
Colowick et al. 1976. Methods in Enzymlology, vol. XLIV, Immobilized Enzymes. New York: Academic Press.
Cox et al. 1985. Accuracy of perceiving blood glucose in IDDM. Diabetes Care 8(6):529-536.
Csöregi et al. 1994. Amperometric microbiosensors for detection of hydrogen peroxide and glucose based on peroxidase-modified carbon fibers. Electroanalysis 6:925-933.
Csoregi et al., 1994. Design, characterization, and one-point in vivo calibration of a subcutaneously implanted glucose electrode. Anal Chem. 66(19):3131-3138.
Currie et al., Novel non-intrusive trans-dermal remote wireless micro-fluidic monitoring systme applied to continuous glucose and lactate assays for casualty care and combat readiness assessment, RTO HFM Symposium, St. Pete Beach, RTO-MP-HFM-109, Aug. 1.
Danielsson et al. 1988. Enzyme thermistors, Methods in Enzymology, 137:181-197.
Dassau et al., In silico evaluation platform for artifical pancreatic β-cell development—a dynamic simulator for closed loop control with hardware-in-the-loop, Diabetes Technology & Therapeutics, 11(3):1-8, 2009.
Davis et al. 1983. Bioelectrochemical fuel cell and sensor based on a quinoprotein, alcohol dehydrogenase. *Enzyme Microb. Technol.*, vol. 5, September, 383-388.
Deutsch et al., "Time series analysis and control of blood glucose levels in diabetic patients". Computer Methods and Programs in Biomedicine 41 (1994) 167-182.
Direct 30/30® meter (Markwell Medical) (Catalog).
Dixon et al. 2002. Characterization in vitro and in vivo of the oxygen dependence of an enzyme/polymer biosensor for monitoring brain glucose. Journal of Neuroscience Methods 119:135-142.
DuPont[1] Dimension AR® (Catalog), 1998.
Durliat et al. 1976. Spectrophotometric and electrochemical determinations of L(+)-lactate in blood by use of lactate dehydrogenase from yeast, Clin. Chem. 22(11):1802-1805.
Edwards Lifesciences. Accuracy for your and your patients. Marketing materials, 4 pp. 2002.
El Degheidy et al. 1986. Optimization of an implantable coated wire glucose sensor. J. Biomed Eng. 8: 121-129.
El-Khatib et al. 2007. Adaptive closed-loop control provides blood-glucose regulation using dual subcutaneous insulin and glucagon infusion in diabetic swine, Journal of Diabetes Science and Technology, 1(2):181-192.
El-Sa'ad et al. 1990. Moisture Absorption by Epoxy Resins: the Reverse Thermal Effect. Journal of Materials Science 25:3577-3582.
Ernst et al. 2002. Reliable glucose monitoring through the use of microsystem technology. Anal. Bioanal. Chem. 373:758-761.
Fabietti et al. 2007. Clinical validation of a new control-oriented model of insulin and glucose dynamcs in subjects with type 1 diabetes, Diabetes Technology & Therapeutics, 9(4):327-338.
Fahy et al., An analysis: hyperglycemic intensive care patients need continuous glocuse monitoring—easier said than done, Journal of Diabetese Science and Technology, 2(2):201-204, Mar. 2008.
Fare et al. 1998. Functional characterization of a conducting polymer-based immunoassay system. Biosensors & Bioelectronics 13(3-4):459-470.
Feldman et al. 2003. A continuous glucose sensor based on wired enzyme technology—results from a 3-day trial in patients with type 1 diabetes. Diabetes Technol Ther 5(5):769-779.
Fischer et al. 1987. Assessment of subcutaneous glucose concentration: validation of the wick technique as a reference for implanted electrochemical sensors in normal and diabetic dogs, Diabetologia 30:940-945.
Fischer et al. 1989. Oxygen Tension at the Subcutaneous Implantation Site of Glucose Sensors. Biomed. Biochim 11/12:965-972.
Fischer et al. 1995. Hypoglycaemia-warning by means of subcutaneous electrochemical glucose sensors: an animal study, Horm. Metab. Rese. 27:53.

(56) References Cited

OTHER PUBLICATIONS

Freedman et al. 1991. Statistics, Second Edition, W.W. Norton & Company, p. 74.
Frohnauer et al. 2001. Graphical human insulin time-activity profiles using standardized definitions. Diabetes Technology & Therapeutics 3(3):419-429.
Frost et al. 2002. Implantable chemical sensors for real-time clinical monitoring: Progress and challenges. Current Opinion in Chemical Biology 6:633-641.
Gabbay et al. 2008. Optical coherence tomography-based continuous noninvasive glucose monitoring in patients with diabetes. Diab. Thechnol. & Therapeut., 10:188-193.
Ganesan et al., Gold layer-based dual crosslinking procedure of glucose oxidase with ferrocene monocarboxylic acid provides a stable biosensor, Analytical Biochemistry 343:188-191, 2005.
Ganesh et al., Evaluation of the VIA® blood chemistry monitor for glucose in healthy and diabetic volunteers, Journal of Diabetese Science and Technology, 2(2):182-193, Mar. 2008.
Garg et al. 1999. Correlation of fingerstick blood glucose measurements with GlucoWatch biographer glucose results in young subjects with type 1 diabetes. Diabetes Care 22(10):1708-1714.
Garg et al. 2004. Improved Glucose Excursions Using an Implantable Real-Time continuous Glucose Sensor in Adults with Type I Diabetes. Diabetes Care 27:734-738.
Gerritsen et al. 1999. Performance of subcutaneously implanted glucose sensors for continuous monitoring. The Netherlands Journal of Medicine 54:167-179.
Gerritsen, M. 2000. Problems associated with subcutaneously implanted glucose sensors. Diabetes Care 23(2):143-145.
Gilligan et al. 1994. Evaluation of a subcutaneous glucose sensor out to 3 months in a dog model. Diabetes Care 17(8):882-887.
Gilligan et al. 2004, Feasibility of continuous long-term glucose monitoring from a subcutaneous glucose sensor in humans. Diabetes Technol Ther 6:378-386.
Godsland et al. 2001. Maximizing the Success Rate of Minimal Model Insulin Sensitivity Measurement in Humans: The Importance of Basal Glucose Levels. The Biochemical Society and the Medical Research Society, 1-9.
Gouda et al., Jul. 4, 2003. Thermal inactiviation of glucose oxidase, The Journal of Biological Chemistry, 278(27):24324-24333.
Gough et al. 2000. Immobilized glucose oxidase in implantable glucose sensor technology. Diabetes Technology & Therapeutics 2(3):377-380.
Gough et al. 2003. Frequency characterization of blood glucose dynamics. Annals of Biomedical Engineering 31:91-97.
Gross et al. 2000. Efficacy and reliability of the continuous glucose monitoring system. Diabetes Technology & Therapeutics, 2(Suppl 1):S19-26.
Gross et al. 2000. Performance evaluation of the MiniMed® continuous glucose monitoring system during patient home use. Diabetes Technology & Therapeutics 2(1):49-56.
Guerci et al., Clinical performance of CGMS in type 1 diabetic patents treated by continuous subcutaneous insulin infusion using insulin analogs, Diabetes Care, 26:582-589, 2003.
Hall et al. 1998. Electrochemical oxidation of hydrogen peroxide at platinum electrodes. Part I: An adsorption-controlled mechanism. Electrochimica Acta, 43(5-6):579-588.
Hall et al. 1998. Electrochemical oxidation of hydrogen peroxide at platinum electrodes. Part II: Effect of potential. Electrochimica Acta 43(14-15):2015-2024.
Hall et al. 1999. Electrochemical oxidation of hydrogen peroxide at platinum electrodes. Part III: Effect of temperature. Electrochimica Acta, 44:2455-2462.
Hall et al. 1999. Electrochemical oxidation of hydrogen peroxide at platinum electrodes. Part IV: Phosphate buffer dependence. Electrochimica Acta, 44:4573-4582.
Hall et al. 2000. Electrochemical oxidation of hydrogen peroxide at platinum electrodes. Part V: Inhibition by chloride. Electrochimica Acta, 45:3573-3579.
Hamilton Syringe Selection Guide. 2006. Syringe Selection. www.hamiltoncompany.com.
Heise et al. 2003. Hypoglycemia warning signal and glucose sensors: Requirements and concepts. Diabetes Technology & Therapeutics 5:563-571.
Heller, "Electrical wiring of redox enzymes," *Acc. Chem. Res.*, 23:128-134 (1990).
Heller, A. 1992. Electrical Connection of Enzyme Redox Centers to Electrodes. J. Phys. Chem. 96:3579-3587.
Heller, A. 1999. Implanted electrochemical glucose sensors for the management of diabetes. Annu Rev Biomed Eng 1:153-175.
Heller, A. 2003. Plugging metal connectors into enzymes. Nat Biotechnol 21:631-2.
Hicks, 1985. In Situ Monitoring, Clinical Chemistry, 31(12):1931-1935.
Hitchman, M. L. 1978. Measurement of Dissolved Oxygen. In Elving et al. (Eds.). Chemical Analysis, vol. 49, Chap. 3, pp. 34-49, 59-123. New York: John Wiley & Sons.
Hoel, Paul G. 1976. Elementary Statistics, Fourth Edition. John Wiley & Sons, Inc.. pp. 113-114.
Hrapovic et al. 2003. Picoamperometric detection of glucose at ultrasmall platinum-based biosensors: preparation and characterization. Anal Chem 75:3308-3315.
http://www.merriam-webster.com/dictionary, *definition for "aberrant,"* Aug. 19, 2008, p. 1.
Hu, et al. 1993. A needle-type enzyme-based lactate sensor for in vivo monitoring, Analytica Chimica Acta, 281:503-511.
Huang et al. A 0.5mV passive telemetry IC for biomedical applications. Swiss Federal Institute of Technology. 4 pp.
Hunter et al. 2000. Minimally Invasive Glucose Sensor and Insulin Delivery System. MIT Home Automation and Healthcare Consortium. Progress Report No. 25.
Jablecki et al. 2000. Simulations of the frequency response of implantable glucose sensors. Analytical Chemistry 72:1853-1859.
Jaremko et al. 1998. Advances toward the implantable artificial pancreas for treatment of diabetes. Diabetes Care 21(3):444-450.
Jensen et al. 1997. Fast wave forms for pulsed electrochemical detection of glucose by incorporation of reductive desorption of oxidation products. Analytical Chemistry 69(9):1776-1781.
Jeong et al. 2003. In vivo calibration of the subcutaneous amperometric glucose sensors using a non-enzyme electrode. Biosensors and Bioelectronics 19:313-319.
Jeutter, D. C. 1982. A transcutaneous implanted battery recharging and biotelemeter power switching system. IEEE Trans Biomed Eng 29:314-321.
Johnson (1991). "Reproducible electrodeposition of biomolecules for the fabrication of miniature electroenzymatic biosensors," *Sensors and Actuators B*, 5:85-89.
Johnson et al. 1992. In vivo evaluation of an electroenzymatic glucose sensor implanted in subcutaneous tissue. Biosensors & Bioelectronics, 7:709-714.
Joung et al. 1998. An energy transmission system for an artificial heart using leakage inductance compensation of transcutaneous transformer. IEEE Transactions on Power Electronics 13(6):1013-1022.
Jovanovic, L. 2000. The role of continuous glucose monitoring in gestational diabetes mellitus. Diabetes Technology & Therapeutics, 2 Suppl 1, S67-71.
Kacaniklic May-Jun. 1994. Electroanalysis, 6(5-6):381-390.
Kamath et al. Calibration of a continuous glucose monitor: effect of glucose rate of change, Eighth Annual Diabetes Technology Meeting, Nov. 13-15, 2008, p. A88.
Kang et al. 2003. In vitro and short-term in vivo characteristics of a Kel-F thin film modified glucose sensor. Anal Sci 19:1481-1486.
Kaufman. 2000. Role of the continuous glucose monitoring system in pediatric patients. Diabetes Technology & Therapeutics 2(1):S-49-S-52.
Kaufman et al. 2001. A pilot study of the continuous glucose monitoring system. Diabetes Care 24(12):2030-2034.
Kawagoe et al. 1991. Enzyme-modified organic conducting salt microelectrode, Anal. Chem. 63:2961-2965.
Keedy et al. 1991. Determination of urate in undiluted whole blood by enzyme electrode. *Biosensors & Bioelectronics*, 6: 491-499.

(56) References Cited

OTHER PUBLICATIONS

Kerner et al. 1988. A potentially implantable enzyme electrode for amperometric measurement of glucose, Horm Metab Res Suppl. 20:8-13.
Kerner et al. "The function of a hydrogen peroxide-detecting electroenzymatic glucose electrode is markedly impaired in human sub-cutaneous tissue and plasma," Biosensors & Bioelectronics, 8:473-482 (1993).
Kerner, W. 2001. Implantable glucose sensors: Present status and future developments. Exp. Clin. Endocrinol. Diabetes 109(Suppl 2):S341-346.
Klueh et al. 2003. Use of Vascular Endothelia Cell Growth Factor Gene Transfer To Enhance Implantable Sensor Function in Vivo, Biosensor Function and Vegf-Gene Transfer, pp. 1072-1086.
Ko, Wen H. 1985. Implantable Sensors for Closed-Loop Prosthetic Systems, Futura Pub. Co., Inc., Mt. Kisco, NY, Chapter 15:197-210.
Kondo et al. 1982. A miniature glucose sensor, implantable in the blood stream. Diabetes Care. 5(3):218-221.
Koschinsky et al. 1988. New approach to technical and clinical evaluation of devices for self-monitoring of blood glucose. Diabetes Care 11(8): 619-619.
Koschinsky et al. 2001. Sensors for glucose monitoring: Technical and clinical aspects. Diabetes Metab. Res. Rev. 17:113-123.
Kost et al. 1985. Glucose-sensitive membranes containing glucose oxidase: activitiy, swelling, and permeability studies, Journal of Biomedical Materials Research 19:1117-1133.
Koudelka et al. 1989. In vivo response of microfabricated glucose sensors to glycemia changes in normal rats. Biomed Biochim Acta 48(11-12):953-956.
Koudelka et al. 1991. In-vivo behaviour of hypodermically implanted microfabricated glucose sensors. Biosensors & Bioelectronics 6:31-36.
Kraver et al. 2001. A mixed-signal sensor interface microinstrument. Sensors and Actuators A 91:266-277.
Krouwer, J. S. 2002. Setting performance goals and evaluating total analytical error for diagnostic assays. Clinical Chemistry 48(6):919-927.
Kruger et al. 2000. Psychological motivation and patient education: A role for continuous glucose monitoring. Diabetes Technology & Therapeutics, 2(Suppl 1):S93-97.
Kulys et al., 1994. Carbon-paste biosensors array for long-term glucose measurement, Biosensors& Beioelectronics, 9:491-500.
Kunjan et al., Automated blood sampling and glocuse sensing in critical care settings, Journal of Diabetes Science and Technology 2(3):194-200, Mar. 2008.
Kurnik et al. 1999. Application of the mixtures of experts algorithm for signal processing in a noninvasive glucose monitoring system. Sensors and Actuators B, 60:19-26.
LaCourse et al. 1993. Optimization of waveforms for pulsed amperometric detection of carbohydrates based on pulsed voltammetry. Analytical Chemistry 65:50-52.
Ladd et al., Structure Determination by X-ray Crystallography, 3rd ed. Plenum, 1996, Ch. 1, pp. xxi-xxiv and 1-58.
Lehmann et al. May 1994. Retrospective valication of a physiological model of glucose-iunsulin interaaction in tyhpe 1 diabetes mellitus, Med. Eng. Phys. 16:193-202.
Lerner et al. 1984. An implantable electrochemical glucose sensor. Ann. N.Y. Acad. Sci. 428:263-278.
Lewandowski et al. 1988. Evaluation of a miniature blood glucose sensor. Trans Am Soc Artif Intern Organs 34:255-258.
Leypoldt et al. 1984. Model of a two-substrate enzyme electrode for glucose. Anal. Chem. 56:2896-2904.
Linke et al. 1994. Amperometric biosensor for in vivo glucose sensing based on glucose oxidase immobilized in a redox hydrogel. Biosensors & Bioelectronics 9:151-158.
Lohn et al., A knowledge-based system for real-time validation of calibrations and measurements, Chemometrics and Intelligent Laboratory Systems, 1999 46, 57-66.
Lowe, 1984. Biosensors, Trends in Biotechnology, 2(3):59-65.

Luong et al. 2004. Solubilization of Multiwall Carbon Nanotubes by 3-Aminopropyltriethoxysilane Towards the Fabrication of Electrochemical Biosensors with Promoted Electron Transfer. Electronanalysis 16(1-2):132-139.
Lyandres et al. (2008). Progress toward an in vivo surface-enhanced raman spectroscopy glucose sensor. *Diabetes Technology & Therapeutics*, 10(4): 257-265.
Lynch et al. 2001. Estimation-based model predictive control of blood glucose in type I diabetics: A simulation study. Proceedings of the IEEE 27th Annual Northeast Bioengineering Conference, pp. 79-80.
Lynn, P. A. 1971. Recursive digital filters for biological signals. Med. & Biol. Engng. 9:37-43.
Maidan et al. 1992. Elimination of Electrooxidizable Interferent-Produced Currents in Amperometric Biosensors, Analytical Chemistry, 64:2889-2896.
Makale et al. 2003. Tissue window chamber system for validation of implanted oxygen sensors. Am. J. Physiol. Heart Circ. Physiol. 284:H2288-2294.
Malin et al. 1999. Noninvasive Prediction of Glucose by Near-Infrared Diffuse Reflectance Spectroscopy. Clinical Chemistry 45:9, 1651-1658.
Mancy et al. 1962. A galvanic cell oxygen analyzer. Journal of Electroanalytical Chemistry 4:65-92.
Maran et al. 2002. Continuous subcutaneous glucose monitoring in diabetic patients: A multicenter analysis. Diabetes Care 25(2):347-352.
March, W. F. 2002. Dealing with the delay. Diabetes Technol Ther 4(1):49-50.
Marena et al. 1993. The artifical endocrine pancreas in clinical practice and research. Panminerva Medica 35(2):67-74.
Martin, R. F. 2000. General Deming regression for estimating systematic bias and its confidence interval in method-comparison studies. *Clinical Chemistry*, 46(1):100-104.
Mascini et al. 1989. Glucose electrochemical probe with extended linearity for whole blood. *J Pharm Biomed Anal* 7(12): 1507-1512.
Mastrototaro et al. "An electroenzymatic glucose sensor fabricated on a flexible substrate," Sensors and Actuators B, 5:139-44 (1991).
Mastrototaro, J. J. 2000. The MiniMed continuous glucose monitoring system. Diabetes Technol Ther 2(Suppl 1):S13-8.
Mastrototaro et al. 2003. Reproducibility of the continuous glucose monitoring system matches previous reports and the intended use of the product. Diabetes Care 26:256; author reply p. 257.
Matsumoto et al. 1998. A micro-planar amperometric glucose sensor unsusceptible to interference species. Sensors and Actuators B 49:68-72.
Matthews et al. 1988. An amperometric needle-type glucose sensor testing in rats and man. Diabetic Medicine 5:248-252.
Mazze et al. 2008. Characterizing glucose exposure for individuals with normal glucose tolerance using continuous glucose monitoring and ambulatory glucose profile analysis. Diab. Thechnol. & Therapeut., 10:149-159.
McCartney et al. 2001. Near-infrared fluorescence lifetime assay for serum glucose based on allophycocyanin-labeled concanavalin A. Anal Biochem 292:216-221.
McGrath et al. 1995. The use of differential measurements with a glucose biosensor for interference compensation during glucose determinations by flow injection analysis. Biosens Bioelectron 10:937-943.
McKean, et al. Jul. 7, 1988. A Telemetry Instrumentation System for Chronically Implanted Glucose and Oxygen Sensors. Transactions on Biomedical Engineering 35:526-532.
Memoli et al. 2002. A comparison between different immobilised glucoseoxidase-based electrodes. J Pharm Biomed Anal 29:1045-1052.
Merriam-Webster Online Dictionary. Definition of "acceleration". http://www.merriam-webster.com/dictionary/Acceleration Jan. 11, 2010.
Merriam-Webster Online Dictionary. Definition of "system". http://www.merriam-webster.com/dictionary/System Jan. 11, 2010.
Merriam-Webster Online Dictionary. The term "nominal." http://www.m-w.com/dictionary/nominal.

(56) References Cited

OTHER PUBLICATIONS

Metzger et al. Jul. 2002. Reproducibility of glucose measurements using the glucose sensor. Diabetes Care 25(6):1185-1191.
Meyerhoff et al. 1992. On line continuous monitoring of subcutaneous tissue glucose in men by combining portable glucosensor with microdialysis. Diabetologia 35:1087-1092.
Moatti-Sirat et al. 1992. Evaluating in vitro and in vivo the interference of ascorbate and acetaminophen on glucose detection by a needle-type glucose sensor, Biosensors & Bioelectronics 7:345-352.
Moatti-Sirat et al. 1992. Towards continuous glucose monitoring: in vivo evaluation of a miniaturized glucose sensor implanted for several days in rat subcutaneous tissue. Diabetologia 35:224-230.
Moatti-Sirat et al., Reduction of acetaminophen interference in glucose sensors by a composite Nafion membrane: demonstration in rats and man, Diabetologia 37(6):610-616, Jun. 1994.
Monsod et al. 2002. Do sensor glucose levels accurately predict plasma glucose concentrations during hypoglycemia and hyperinsulinemia? Diabetes Care 25(5):889-893.
Morff et al. 1990. Microfabrication of reproducible, economical, electroenzymatic glucose sensors, Annual International Conference of the IEEE Engineering in Medicine and Biology Society, 12(2):0483-0484.
Mosbach et al. 1975. Determination of heat changes in the proximity of immobilized enzymes with an enzyme termistor and its use for the assay of metobolites, Biochim. Biophys. Acta. (Enzymology), 403:256-265.
Motonaka et al. 1993. Determination of cholesteral and cholesteral ester with novel enzyme microsensors, Anal. Chem. 65:3258-3261.
Moussy et al. 1994. A miniaturized Nafion-based glucose sensor: In vitro and in vivo evaluation in dogs. Int. J. Artif. Organs 17(2):88-94.
Muslu. 1991. Trickling filter performance. Apllied Biochemistry and Biotechnology 37:211-224.
Nafion® 117 Solution Product Description, Product No. 70160, Sigma-Aldrich Corp., St. Louis, MO.
Neuburger et al. 1987. Pulsed amperometric detection of carbohydrates at gold electrodes with a two-step potential waveform. Anal. Chem. 59:150-154.
Ohara, et al. Dec. 1993. Glucose electrodes based on cross-linked bis(2,2'-bipyridine)chlorooosmium(+/2+) complexed poly(1-vinylimidazole) films, Analytical Chemistry, 65:3512-3517.
Ohara et al. 1994. "Wired" enzyme electrodes for amperometric determination of glucose or lactate in the presence of interfering substances. Anal Chem 66:2451-2457.
Okuda et al. 1971. Mutarotase effect on micro determinations of D-glucose and its anomers with β-D-glucose oxidase. Anal Biochem 43:312-315.
Oxford English Dictionary Online. Definition of "impending". http://www.askoxford.com/results/?view=dev dict&field-12668446 Impending&branch= Jan. 11, 2010.
Palmisano et al. 2000. Simultaneous monitoring of glucose and lactate by an interference and cross-talk free dual electrode amperometric biosensor based on electropolymerized thin films. Biosensors & Bioelectronics 15:531-539.
Panteleon et al. 2003. The role of the independent variable to glucose sensor calibration. Diabetes Technology & Therapeutics 5(3):401-410.
Parker et al. 1999. A model-based algorithm for blood glucose control in type I diabetic patients. IEEE Trans. Biomed. Eng. 46(2):148-157.
Patel et al. 2003. Amperometric glucose sensors based on ferrocene containing polymeric electron transfer systems—a preliminary report. Biosens Bioelectron 18:1073-6.
Peacock et al. 2008. Cardiac troponin and outcome in acute heart failure. N. Engl. J. Med., 358: 2117-2126.
Pfeiffer, E.F. 1990. The glucose sensor: the missing link in diabetes therapy, Horm Metab Res Suppl. 24:154-164.
Pfeiffer et al. 1992. On line continuous monitoring of subcutaneous tissue glucose is feasible by combining portable glucosensor with microdialysis. Horm. Metab. Res. 25:121-124.
Phillps. 1995. A high capacity transcutaneous energy transmission system. ASAIO Journal 41:M259-M262.
Pichert et al. 2000. Issues for the coming age of continuous glucose monitoring Diabetes Educ 26(6):969-980.
Pickup et al. "Implantable glucose sensors: choosing the appropriate sensing strategy," Biosensors, 3:335-346 (1987/88).
Pickup et al. "In vivo molecular sensing in diabetes mellitus: an implantable glucose sensor with direct electron transfer," Diabetologia, 32:213-217 (1989).
Pickup et al. 1989. Potentially-implantable, amperometric glucose sensors with mediated electron transfer: improving the operating stability. Biosensors 4:109-119.
Pickup et al. 1993. Responses and Calibration of Amperometric Glucose Sensors Implanted in the Subcutaneous Tissue of Man. ACTA Diabetol, pp. 143-148.
Pickup et al. 1993. Developing glucose sensors for in vivo use. Elsevier Science Publishers Ltd (UK), TIBTECH vol. 11: 285-291.
Pinner et al., Cross-linking of cellulose acetate by ionizing radiation, Nature, vol. 184, 1303-1304, Oct. 24, 1959.
Pishko et al. "Amperometric glucose microelectrodes prepared through immobilization of glucose oxidase in redox hydrogels," Anal. Chem., 63:2268-72 (1991).
Pitzer et al. 2001. Detection of hypoglycemia with the GlucoWatch biographer. Diabetes Care 24(5):881-885.
Poirier et al. 1998. Clinical and statistical evaluation of self-monitoring blood glucose meters. Diabetes Care 21(11):1919-1924.
Poitout, et al. 1991. In Vitro and In Vivo Evaluation in Dogs of a Miniaturized Glucose Sensor, ASAIO Transactions, 37:M298-M300.
Poitout et al. 1993. A glucose monitoring system for on line estimation in man of blood glucose concentration using a miniaturized glucose sensor implanted in the subcutaneous tissue and a wearable control unit. Diabetologia 36:658-663.
Poitout et al. 1994. Development of a glucose sensor for glucose monitoring in man: the disposable implant concept. Clinical Materials 15:241-246.
Postlethwaite et al. 1996. Interdigitated array electrode as an alternative to the rotated ring-disk electrode for determination of the reaction products of dioxygen reduction. Analytical Chemistry 68:2951-2958.
Prabhu et al. 1981. Electrochemical studies of hydrogen peroxide at a platinum disc electrode, Electrochimica Acta 26(6):725-729.
Quinn et al. 1995. Kinetics of glucose delivery to subcutaneous tissue in rats measured with 0.3-mm amperometric microsensors. The American Physiological Society E155-E161.
Quinn et al. 1997. Biocompatible, glucose-permeable hydrogel for in situ coating of implantable biosensors. Biomaterials 18:1665-1670.
Rabah et al., 1991. Electrochemical wear of graphite anodes during electrolysis of brine, Carbon, 29(2):165-171.
Reach et al. 1986. A Method for Evaluating in vivo the Functional Characteristics of Glucose Sensors. Biosensors 2:211-220.
Reach et al. 1992. Can continuous glucose monitoring be used for the treatment of diabetes? Analytical Chemistry 64(5):381-386.
Reach, G. 2001. Which threshold to detect hypoglycemia? Value of receiver-operator curve analysis to find a compromise between sensitivity and specificity. Diabetes Care 24(5):803-804.
Reach, Gerard. 2001. Letters to the Editor Re: Diabetes Technology & Therapeutics, 2000;2:49-56. Diabetes Technology & Therapeutics 3(1):129-130.
Rebrin et al. "Automated feedback control of subcutaneous glucose concentration in diabetic dogs," Diabetologia, 32:573-76 (1989).
Rebrin et al. 1992. Subcutaenous glucose monitoring by means of electrochemical sensors: fiction or reality? J. Biomed. Eng. 14:33-40.
Rebrin et al. 1999. Subcutaneous glucose predicts plasma glucose independent of insulin: Implications for continuous monitoring. Am. J. Physiol. 277:E561-71.
Reusch. 2004. Chemical Reactivity. Organometallic Compounds. Virtual Textbook of Organic Chem. pp. 1-16, http://www.cem.msu.edu/~reusch/VirtualText/orgmetal.htm.
Rhodes et al. 1994. Prediction of pocket-portable and implantable glucose enzyme electrode performance from combined species permeability and digital simulation analysis. Analytical Chemistry 66(9):1520-1529.

(56) References Cited

OTHER PUBLICATIONS

Rigla et al. 2008. Real-time continuous glucose monitoring together with telemedical assitance improves glycemic control and glucose stability in pump-treated patients. Diab. Thechnol. & Therapeut., 10:194-199.
Rinken et al. 1998. Calibration of glucose biosensors by using pre-steady state kinetic data. Biosensors & Bioelectronics, 13:801-807.
Rivers et al., Central venous oxygen saturation monitoring in the critically ill patient, Current Opinion in Critical Care, 7:204-211, 2001.
Sakakida et al. 1992. Development of Ferrocene-Mediated Needle-Type Glucose Sensor as a Measure of True Subcutaneous Tissue Glucose Concentrations. Artif. Organs Today 2(2):145-158.
Sakakida et al. 1993. Ferrocene-Mediated Needle Type Glucose Sensor Covered with Newly Designed Biocompatible Membran, Sensors and Actuators B 13-14:319-322.
Salardi et al. 2002. The glucose area under the profiles obtained with continuous glucose monitoring system relationships with HbA1c in pediatric type 1 diabetic patients. Diabetes Care 25(10):1840-1844.
San Diego Plastics, Inc. 2009. Polyethylene Data Sheet, http://www.sdplastics.com/polyeth.html.
Sansen et al. 1985. "Glucose sensor with telemetry system." In Ko, W. H. (Ed.). Implantable Sensors for Closed Loop Prosthetic Systems. Chap. 12, pp. 167-175, Mount Kisco, NY: Futura Publishing Co.
Sansen et al. 1990. A smart sensor for the voltammetric measurement of oxygen or glucose concentrations. Sensors and Actuators B 1:298-302.
Schmidt et al. 1992. Calibration of a wearable glucose sensor. The International Journal of Artificial Organs 15(1):55-61.
Schmidt et al. 1993. Glucose concentration in subcutaneous extracellular space. Diabetes Care 16(5):695-700.
Schmidtke et al. 1998. Accuracy of the one-point in vivo calibration of "wired" glucose oxidase electrodes implanted in jugular veins of rats in periods of rapid rise and decline of the glucose concentration. Anal Chem 70:2149-2155.
Schmidtke et al., Measurement and modeling of the transient difference between blood and subcutaneous glucose concentrations in the rat after injection of insulin. *Proc Natl Aced Sci U S A* 1998, 95, 294-299.
Schoemaker et al. 2003. The SCGM1 system: Subcutaneous continuous glucose monitoring based on microdialysis technique. Diabetes Technology & Therapeutics 5(4):599-608.
Schoonen et al. 1990 Development of a potentially wearable glucose sensor for patients with diabetes mellitus: design and in-vitro evaluation. Biosensors & Bioelectronics 5:37-46.
Service et al. 1970. Mean amplitude of glycemic excursions, a measure of diabetic instability. Diabetes, 19: 644-655.
Service et al. 1987. Measurements of glucose control. Diabetes Care, 10: 225-237.
Service, R. F. 2002. Can sensors make a home in the body? Science 297:962-3.
Sharkawy et al. 1996. Engineering the tissue which encapsulates subcutaneous implants. I. Diffusion properties, J Biomed Mater Res, 37:401-412.
Shaw et al. "In vitro testing of a simply constructed, highly stable glucose sensor suitable for implantation in diabetic patients," Biosensors & Bioelectronics, 6:401-406 (1991).
Shichiri et al. 1982. Wearable artificial endocrine pancrease with needle-type glucose sensor. Lancet 2:1129-1131.
Shichiri et al. 1983. Glycaemic Control in Pancreatectomized Dogs with a Wearable Artificial Endocrine Pancreas. Diabetologia 24:179-184.
Shichiri et al. 1985. Needle-type Glucose Sensor for Wearable Artificial Endocrine Pancreas in Implantable Sensors 197-210.
Shichiri et al. 1986. Telemetry Glucose Monitoring Device with Needle-Type Glucose Sensor: A Useful Tool for Blood Glucose Monitoring in Diabetic Individuals. Diabetes Care, Inc. 9(3):298-301.
Shichiri et al. 1989. Membrane Design For Extending the Long-Life of an Implantable Glucose Sensor. Diab. Nutr. Metab. 2:309-313.
Shults et al. 1994. A telemetry-instrumentation system for monitoring multiple subcutaneously implanted glucose sensors. IEEE Transactions on Biomedical Engineering 41(10):937-942.
Skyler, J. S. 2000. The economic burden of diabetes and the benefits of improved glycemic control: The potential role of a continuous glucose monitoring system. Diabetes Technology & Therapeutics 2 Suppl 1:S7-12.
Slater-Maclean et al. 2008. Accuracy of glycemic measurements in the critically ill. Diab. Thechnol. & Therapeut., 10:169-177.
Sokol et al. 1980, Immobilized-enzyme rate-determination method for glucose analysis, Clin. Chem. 26(1):89-92.
Sokolov et al. 1995. Metrological opportunities of the dynamic mode of operating an enzyme amperometric biosensor. Med. Eng. Phys. 17(6):471-476.
Sparacino et al., 2008. Continuous glucose monitoring time series and hypo/hyperglycemia prevention: requirements, methods, open problems, Current Diabetes Reviews, 4:181-192.
Sproule et al. 2002. Fuzzy pharmacology: Theory and applications. Trends in Pharmacological Sciences, 23(9):412-417.
Sriyudthsak et al. 1996. Enzyme-epoxy membrane based glucose analyzing system and medical applications. Biosens Bioelectron 11:735-742.
Steil et al. 2003. Determination of plasma glucose during rapid glucose excursions with a subcutaneous glucose sensor. Diabetes Technology & Therapeutics 5(1):27-31.
Stern et al., 1957. Electrochemical polarization: 1. A theoretical analysis of the shape of polarization curves, Journal of the Electrochemical Society, 104(1):56-63.
Sternberg et al. 1988. Study and Development of Multilayer Needle-type Enzyme-based Glucose Microsensors. Biosensors 4:27-40.
Sternberg et al. 1996. Does fall in tissue glucose precede fall in blood glucose? Diabetologia 39:609-612.
Street et al. 1988. A note on computing robust regression estimates via iteratively reweighted least squares. The American Statistician 42(2):152-154.
Sumino T. et al. 1998. Preliminary study of continuous glucose monitoring with a microdialysis technique. Proceedings of the IEEE, 20(4):1775-1778.
Takegami et al. 1992. Pervaporation of ethanol water mixtures using novel hydrophobic membranes containing polydimethylsiloxane, Journal of Membrane Science, 75(93-105).
Tamura, T. et al. 2000. Preliminary study of continuous glucose monitoring with a microdialysis technique and a null method—a numerical analysis. Frontiers Med. Biol. Engng. 10(2):147-156.
Tanenberg et al. 2000. Continuous glucose monitoring system: A new approach to the diagnosis of diabetic gastroparesis. Diabetes Technology & Therapeutics, 2 Suppl 1:S73-80.
Tatsuma et al. 1991. Oxidase/peroxidase bilayer-modified electrodes as sensors for lactate, pyruvate, cholesteral and uric acid, Analytica Chimica Acta, 242:85-89.
Thome et al. 1995.—Abstract—Can the decrease in subcutaneous glucose concentration precede the decrease in blood glucose level? Proposition for a push-pull kinetics hypothesis, Horm. Metab. Res. 27:53.
Thomé-Duret et al. 1996. Modification of the sensitivity of glucose sensor implanted into subcutaneous tissue. Diabetes Metabolism, 22:174-178.
Thome-Duret et al. 1996. Use of a subcutaneous glucose sensor to detect decreases in glucose concentration prior to observation in blood, Anal. Chem. 68:3822-3826.
Thomé-Duret et al. 1998. Continuous glucose monitoring in the free-moving rat. Metabolism, 47:799-803.
Thompson et al., In Vivo Probes: Problems and Perspectives, Department of Chemistry, University of Toronto, Canada, pp. 255-261, 1986.
Tierney et al. 2000. Effect of acetaminophen on the accuracy of glucose measurements obtained with the GlucoWatch biographer. Diabetes Technol Ther 2:199-207.
Tierney et al. 2000. The GlucoWatch® biographer: A frequent, automatic and noninvasive glucose monitor. Ann. Med. 32:632-641.

(56) References Cited

OTHER PUBLICATIONS

Tilbury et al. 2000. Receiver operating characteristic analysis for intelligent medical systems—A new approach for finding confidence intervals. IEEE Transactions on Biomedical Engineering 47(7):952-963.
Torjman et al., Glucose monitoring in acute care: technologies on the horizon, Journal of Deabetes Science and Technology, 2(2):178-181, Mar. 2008.
Trajanoski et al. 1998. Neural predictive controller for insulin delivery using the subcutaneous route. IEEE Transactions on Biomedical Engineering 45(9):1122-1134.
Trecroci, D. 2002. A Glimpse into the Future—Continuous Monitoring of Glucose with a Microfiber. Diabetes Interview 42-43.
Tse and Gough. 1987. Time-Dependent Inactivation of Immobilized Glucose Oxidase and Catalase. Biotechnol. Bioeng. 29:705-713.
Turner and Pickup, "Diabetes mellitus: biosensors for research and management," *Biosensors*, 1:85-115 (1985).
Turner et al. 1984. Carbon Monoxide: Acceptor Oxidoreductase from *Pseudomonas thermocarboxydovorans* Strain C2 and its use in a Carbon Monoxide Sensor. Analytica Chimica Acta, 163: 161-174.
Unger et al. 2004. Glucose control in the hospitalized patient. Emerg Med 36(9):12-18.
Updike et al. 1967. The enzyme electrode. Nature, 214:986-988.
Updike et al. 1979. Continuous glucose monitor based on an immobilized enzyme electrode detector. J Lab Clin Med, 93(4):518-527.
Updike et al. 1982. Implanting the glucose enzyme electrode: Problems, progress, and alternative solutions. Diabetes Care, 5(3):207-212.
Updike et al. 1988. Laboratory Evaluation of New Reusable Blood Glucose Sensor. Diabetes Care, 11:801-807.
Updike et al. 1994. Enzymatic glucose sensor: Improved long-term performance in vitro and in vivo. ASAIO Journal, 40(2):157-163.
Updike et al. 1997. Principles of long-term fully implanted sensors with emphasis on radiotelemetric monitoring of blood glucose form inside a subcutaneous foreign body capsule (FBC). In Fraser, ed., Biosensors in the Body. New York. John Wiley & Sons.
Updike et al. 2000. A subcutaneous glucose sensor with improved longevity, dynamic range, and stability of calibration. Diabetes Care 23(2):208-214.
Utah Medical Products Inc., Blood Pressure Tranducers product specifications. 6 pp. 2003-2006, 2003.
Vadgama, P. Nov. 1981. Enzyme electrodes as practical biosensors. Journal of Medical Engineering & Technology 5(6):293-298.
Vadgama. 1988. Diffusion limited enzyme electrodes. NATO ASI Series: Series C, Math and Phys. Sci. 226:359-377.
Valdes et al. 2000. In vitro and in vivo degradation of glucose oxidase enzyme used for an implantable glucose biosensor. Diabetes Technol. Ther. 2:367-376.
Van den Berghe 2004. Tight blood glucose control with insulin in "real-life" intensive care. Mayo Clin Proc 79(8):977-978.
Velho et al. 1989. In vitro and in vivo stability of electrode potentials in needle-type glucose sensors. Influence of needle material. Diabetes 38:164-171.
Velho et al. 1989. Strategies for calibrating a subcutaneous glucose sensor. Biomed Biochim Acta 48(11/12):957-964.
von Woedtke et al. 1989. In situ calibration of implanted electrochemical glucose sensors. Biomed Biochim. Acta 48(11/12):943-952.
Wagner et al. 1998. Continuous amperometric monitoring of glucose in a brittle diabetic chimpanzee with a miniature subcutaneous electrode. Proc. Natl. Acad. Sci. A, 95:6379-6382.
Wang et al. 1994. Highly Selective Membrane-Free, Mediator-Free Glucose Biosensor. Anal. Chem. 66:3600-3603.
Wang et al. 1997. Improved ruggedness for membrane-based amperometric sensors using a pulsed amperometric method. Anal Chem 69:4482-4489.
Ward et al. 1999. Assessment of chronically implanted subcutaneous glucose sensors in dogs: The effect of surrounding fluid masses. ASAIO Journal, 45:555-561.
Ward et al. 2000. Understanding Spontaneous Output Fluctuations of an Amperometric Glucose Sensor: Effect of Inhalation Anesthesia and e of a Nonenzyme Containing Electrode. ASAIO Journal 540-546.
Ward et al. 2000. Rise in background current over time in a subcutaneous glucose sensor in the rabbit: Relevance to calibration and accuracy. Biosensors & Bioelectronics, 15:53-61.
Ward et al. 2002. A new amperometric glucose microsensor: In vitro and short-term in vivo evaluation. Biosensors & Bioelectronics, 17:181-189.
Wientjes, K. J. C. 2000. Development of a glucose sensor for diabetic patients (Ph.D. Thesis).
Wikipedia 2006. "Intravenous therapy," http://en.wikipedia.org/wiki/Intravenous_therapy, Aug. 15, 2006, 6 pp.
Wiley Electrical and Electronics Engineering Dictionary. 2004. John Wiley & Sons, Inc. pp. 141, 142, 548, 549.
Wilkins et al. 1988. The coated wire electrode glucose sensor, Horm Metab Res Suppl., 20:50-55.
Wilkins et al. 1995. Glucose monitoring: state of the art and future possibilities. Med Eng Phys 18:273-288.
Wilkins et al. 1995. Integrated implantable device for long-term glucose monitoring. Biosens. Bioelectron 10:485-494.
Wilson et al. 1992. Progress toward the development of an implantable sensor for glucose. Clin. Chem. 38(9):1613-1617.
Wilson et al. 2000. Enzyme-based biosensors for in vivo measurements. Chem. Rev., 100:2693-2704.
Wood, W. et al. Mar. 1990. Hermetic Sealing with Epoxy. Mechanical Engineering 1-3.
Woodward. 1982. How Fibroblasts and Giant Cells Encapsulate Implants: Considerations in Design of Glucose Sensor. Diabetes Care 5:278-281.
Worsley et al., Measurement of glucose in blood with a phenylboronic acid optical sensor, Journal of Diabetes Science and Technology, 2(2):213-220, Mar. 2008.
Wright et al., Bioelectrochemical dehalogenations via direct electrochemistry of poly(ethylene oxide)-modified myoglobin, Electrochemistry Communications 1 (1999) 603-611.
Wu et al. 1999. In situ electrochemical oxygen generation with an immunoisolation device. Annals New York Academy of Sciences, pp. 105-125.
Yamasaki, Yoshimitsu. Sep. 1984. The development of a needle-type glucose sensor for wearable artificial endocrine pancreas. Medical Journal of Osaka University 35(1-2):25-34.
Yamasaki et al. 1989. Direct measurement of whole blood glucose by a needle-type sensor. Clinica Chimica Acta. 93:93-98.
Yang et al (1996). "A glucose biosensor based on an oxygen electrode: In-vitro performances in a model buffer solution and in blood plasma," Biomedical Instrumentation & Technology, 30:55-61.
Yang et al. 1998. Development of needle-type glucose sensor with high selectivity. Science and Actuators B 46:249-256.
Yang, et al. 2004. A Comparison of Physical Properties and Fuel Cell Performance of Nafion and Zirconium Phosphate/Nafion Composite Membranes. Journal Of Membrane Science 237:145-161.
Ye et al. 1993. High Current Density 'Wired' Quinoprotein Glucose Dehydrogenase Electrode. Anal. Chem. 65:238-241.
Zamzow et al. 1990. Development and evaluation of a wearable blood glucose monitor, ASAIO Transactions; 36(3): pp. M588-M591.
Zavalkoff et al. 2002. Evaluation of conventional blood glucose monitoring as an indicator of integrated glucose values using a continuous subcutaneous sensor. Diabetes Care 25(9):1603-1606.
Zethelius et al. 2008. Use of multiple biomarkers to improve the prediction of death from cardiovascular causes. N. Engl. J. Med., 358: 2107-2116.
Zhang et al (1993). Electrochemical oxidation of $H_2O_2$ on Pt and Pt + Ir electrodes in physiological buffer and its applicability to $H_2O_2$-based biosensors. *J. Electroanal. Chem.*, 345:253-271.
Zhang et al. 1993. In vitro and in vivo evaluation of oxygen effects on a glucose oxidase based implantable glucose sensor. Analytica Chimica Acta, 281:513-520.
Zhang et al. 1994. Elimination of the acetaminophen interference in an implantable glucose sensor. Analytical Chemistry 66(7):1183-1188.

(56) References Cited

OTHER PUBLICATIONS

Zhu et al. (1994). "Fabrication and characterization of glucose sensors based on a microarray $H_2O_2$ electrode." *Biosensors & Bioelectronics*, 9: 295-300.
Zhu et al. 2002. Planar amperometric glucose sensor based on glucose oxidase immobilized by chitosan film on prussian blue layer. Sensors, 2:127-136.
Ziaie et al. 1997. A single-channel implantable microstimulator for functional neuromuscular stimulation. IEEE Transactions on Biomedical Engineering 44(10):909-920.
Office Action dated Sep. 30, 2002 in U.S. Appl. No. 09/636,369.
Office Action dated Jul. 15, 2008 in U.S. Appl. No. 10/633,367.
Office Action dated Jun. 11, 2009 in U.S. Appl. No. 10/633,367.
Office Action dated Jul. 30, 2009 in U.S. Appl. No. 12/102,654.
Office Action dated Mar. 10, 2010 in U.S. Appl. No. 12/102,654.
Office Action dated Dec. 23, 2008 in U.S. Appl. No. 12/102,745.
Office Action dated Oct. 20, 2004 in U.S. Appl. No. 10/632,537.
Office Action dated Dec. 21, 2004 in U.S. Appl. No. 10/632,537
Office Action dated May 29, 2008 in U.S. Reexam. No. 95/001,039.
Office Action dated May 19, 2009 in U.S. Appl. No. 11/038,340.
Office Action dated Nov. 9, 2009 in U.S. Appl. No. 11/038,340.
Office Action dated Jun. 17, 2008 in U.S. Appl. No. 11/038,340.
Office Action dated Jan. 5, 2009 in U.S. Appl. No. 11/038,340.
Office Action dated Feb. 12, 2007 in U.S. Appl. No. 10/633,404.
Office Action dated Jun. 17, 2008 in U.S. Reexam. No. 95/001,038.
Office Action dated Dec. 18, 2008 in U.S. Appl. No. 10/633,329.
Office Action dated Apr. 27, 2010 in U.S. Appl. No. 10/633,329.
Office Action dated Jun. 23, 2009 in U.S. Appl. No. 10/648,849.
Office Action dated Jun. 24, 2008 n U.S. Appl. No. 11/007,920.
Office Action dated Nov. 28, 2007 in U.S. Appl. No. 10/991,966.
Office Action dated Jul. 22, 2008 in U.S. Appl. No. 10/991,966.
Office Action dated Nov. 27, 2006 in U.S. Appl. No. 10/789,359.
Office Action dated Mar. 20, 2008 in U.S. Appl. No. 10/789,359.
Office Action dated Oct. 3, 2008 in U.S. Appl. No. 10/789,359.
Office Action mailed Jun. 5, 2008 in U.S. Appl. No. 10/838,909.
Office Action mailed Mar. 16, 2009 in U.S. Appl. No. 10/838,909.
Office Action dated Mar. 31, 2008 in U.S. Appl. No. 11/077,759.
Office Action dated Jul. 10, 2008 in U.S. Appl. No. 11/077,759.
Office Action dated May 26, 2009 in U.S. Appl. No. 11/077,759.
Office Action dated Jul. 21, 2009 in U.S. Appl. No. 11/077,739.
Office Action dated Dec. 29, 2009 in U.S. Appl. No. 11/077,739.
Office Action dated Mar. 1, 2010 in U.S. Appl. No. 11/077,739.
Office Action dated Jun. 1, 2007 in U.S. Appl. No. 11/077,740.
Office Action dated Nov. 1, 2007 in U.S. Appl. No. 11/077,740.
Office Action dated Feb. 7, 2008 in U.S. Appl. No. 11/077,740.
Office Action dated Jul. 25, 2008 in U.S. Appl. No. 11/077,740.
Office Action dated Apr. 28, 2009 in U.S. Appl. No. 11/077,740.
Office Action dated Dec. 31, 2007 in U.S. Appl. No. 11/077,765.
Office Action dated May 16, 2008 in U.S. Appl. No. 11/077,765.
Office Action dated Sep. 19, 2008 in U.S. Appl. No. 11/077,765.
Office Action dated Jan. 23, 2009 in U.S. Appl. No. 11/077,765.
Office Action dated Feb. 3, 2010 in U.S. Appl. No. 11/077,765.
Office Action dated Jun. 26, 2008 in U.S. Appl. No. 11/157,365.
Office Action dated Jan. 7, 2009 in U.S. Appl. No. 11/157,365.
Office Action dated Jul. 21, 2009 in U.S. Appl. No. 11/157,365.
Office Action dated Jan. 21, 2010 in U.S. Appl. No. 11/157,365.
Office Action dated Oct. 4, 2006 in U.S. Appl. No. 11/334,876.
Office Action dated Sep. 25, 2007 in U.S. Appl. No. 11/334,876.
Office Action dated May 2, 2008 in U.S. Appl. No. 11/334,876.
Office Action dated Aug. 26, 2008 in U.S. Appl. No. 11/334,876.
Office Action dated Aug. 25, 2009 in U.S. Appl. No. 11/334,876.
Office Action dated Jun. 30, 2008 in U.S. Appl. No. 11/360,252.
Office Action dated Jan. 29, 2009, in U.S. Appl. No. 11/360,252.
Office Action dated Jul. 23, 2009, in U.S. Appl. No. 11/360,252.
Office Action dated Aug. 11, 2008 in U.S. Appl. No. 11/360,819.
Office Action dated Dec. 26, 2008 in U.S. Appl. No. 11/360,819.
Office Action dated Oct. 29, 2009 in U.S. Appl. No. 11/360,819.
Office Action dated Apr. 7, 2010 in U.S. Appl. No. 11/360,819.
Gough. (May 2001) The implantable glucose sensor: An example of bioengineering design. Introduction to Bioengineering, Chapter 3, pp. 57-66.
Smith, Steven W. The Scientist and Engineer's Guide to Digital Signal Processing. California Technical Publishing 1997-2007 [retrieved Jan. 1, 2009] http://www.dspguide.com/ch19.htm. 2 pages.
Vig et al. A Review of Sensor Sensitivity and Stability. IEEE/EIA International Frequency Control Symposium and Exhibition. 2000. pp. 30-33.
Office Action dated Jul. 6, 2012 for U.S. Appl. No. 12/195,773, filed Aug. 21, 2008.
Electronic File History of U.S. Appl. No. 12/098,353, filed Apr. 4, 2008 containing Office Action(s) dated Aug. 26, 2010, Oct. 25, 2010, Jan. 4, 2011, Feb. 17, 2011, Mar. 9, 2011, May 4, 2011 and May 24, 2011 and Applicant(s) Response(s) dated Nov. 24, 2010, Mar. 4, 2011, Apr. 18, 2011 and Jun. 3, 2011 as of Dec. 18, 2012.
Electronic File History of U.S. Appl. No. 12/098,359, filed Apr. 4, 2008 containing Office Action(s) dated Jul. 7, 2010, Oct. 25, 2010, Jan. 13, 2011, Feb. 25, 2011, Mar. 9, 2011, Mar. 22, 2011, May 23, 2011, Jul. 22, 2011, Dec. 15, 2011, Jan. 23, 2012, Mar. 21, 2012, Jun. 18, 2012 and Oct. 12, 2012 and Applicant(s) Response(s) dated Nov. 1, 2010, Nov. 24, 2010, Mar. 4, 2011, Jun. 3, 2011, Nov. 22, 2011 and Aug. 21, 2012 as of Dec. 18, 2012.
Electronic File History of U.S. Appl. No. 12/098,627, filed Apr. 7, 2008 containing Office Action(s) dated Sep. 9, 2010, Oct. 25, 2010, Mar. 3, 2011, Mar. 9, 2011, May 24, 2011, Jul. 29, 2011, Nov. 2, 2011, Dec. 6, 2011, Jan. 12, 2012, Apr. 20, 2012, Jul. 16, 2012, Oct. 1, 2012, and Nov. 15, 2012 and Applicant(s) Response(s) dated Dec. 3, 2010, Jun. 3, 2011, Oct. 31, 2011, May 14, 2012 and Sep. 17, 2012 as of Dec. 18, 2012.
Electronic File History of U.S. Appl. No. 12/748,144, filed Mar. 26, 2010 containing Office Action(s) dated Jul. 20, 2012, Sep. 5, 2012 and Nov. 26, 2012 and Applicant(s) Response(s) filed Aug. 31, 2012 as of Dec. 18, 2012.
Electronic File History of U.S. Appl. No. 12/098,353, filed Apr. 4, 2008 containing Office Action(s) dated Aug. 26, 2010, Oct. 25, 2010, Jan. 4, 2011, Feb. 17, 2011, Mar. 9, 2011, May 4, 2011, May 24, 2011, Jun. 20, 2013, and Sep. 19, 2013 and Applicant(s) Response(s) dated Nov. 24, 2010, Mar. 4, 2011, Apr. 18, 2011 and Jun. 3, 2011 as of Sep. 20, 2013.
US 7,530,950, 05/2009, Brister et al. (withdrawn)

\* cited by examiner

SYSTEM AND METHODS FOR PROCESSING ANALYTE SENSOR DATA

CROSS REFERENCE TO RELATED APPLICATION

This application is a division of U.S. application Ser. No. 10/633,329 filed Aug. 1, 2003, which is incorporated by reference herein in its entirety, and is hereby made a part of this specification.

FIELD OF THE INVENTION

The present invention relates generally to systems and methods for analyte sensor data processing. Particularly, the present invention relates to retrospectively and/or prospectively initiating a calibration, converting sensor data, updating the calibration, evaluating received reference and sensor data, and evaluating the calibration for the analyte sensor.

BACKGROUND OF THE INVENTION

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which may cause an array of physiological derangements (e.g., kidney failure, skin ulcers, or bleeding into the vitreous of the eye) associated with the deterioration of small blood vessels. A hypoglycemic reaction (low blood sugar) may be induced by an inadvertent overdose of insulin, or after a normal dose of insulin or glucose-lowering agent accompanied by extraordinary exercise or insufficient food intake.

Conventionally, a diabetic person carries a self-monitoring blood glucose (SMBG) monitor, which typically comprises uncomfortable finger pricking methods. Due to the lack of comfort and convenience, a diabetic will normally only measure his or her glucose level two to four times per day. Unfortunately, these time intervals are so far spread apart that the diabetic will likely find out too late, sometimes incurring dangerous side effects, of a hyper- or hypo-glycemic condition. In fact, it is not only unlikely that a diabetic will take a timely SMBG value, but the diabetic will not know if their blood glucose value is going up (higher) or down (lower) based on conventional methods, inhibiting their ability to make educated insulin therapy decisions.

SUMMARY OF THE INVENTION

Systems and methods are needed that accurately provide estimated glucose measurements to a diabetic patient continuously and/or in real time so that they may proactively care for their condition to safely avoid hyper- and hypo-glycemic conditions. Real time and retrospective estimated glucose measurements require reliable data processing in order to provide accurate and useful output to a patient and/or doctor.

Similarly, systems and methods are needed that accurately provide substantially continuous estimated analyte measurements for a variety of known analytes (e.g., oxygen, salts, protein, and vitamins) to provide prospective and/or retrospective data analysis and output to a user.

Accordingly, systems and methods are provided for retrospectively and/or prospectively calibrating a sensor, initializing a sensor, converting sensor data into calibrated data, updating and maintaining a calibration over time, evaluating received reference and sensor data for clinical acceptability, and evaluating the calibration statistical acceptability, to ensure accurate and safe data output to a patient and/or doctor.

In a first embodiment a method is provided for initializing a substantially continuous analyte sensor, the method including: receiving a data stream from an analyte sensor, including one or more sensor data points; receiving reference data from a reference analyte monitor, including two or more reference data points; providing at least two matched data pairs by matching reference analyte data to substantially time corresponding sensor data; forming a calibration set including the at least two matching data pairs; and determining a stability of the continuous analyte sensor.

In an aspect of the first embodiment, the step of determining the stability of the substantially continuous analyte sensor includes waiting a predetermined time period between about one minute and about six weeks.

In an aspect of the first embodiment, the step of determining the stability of the substantially continuous analyte sensor includes evaluating at least two matched data pairs.

In an aspect of the first embodiment, the step of determining the stability of the substantially continuous analyte sensor includes evaluating one of pH, oxygen, hypochlorite, interfering species, correlation of matched pairs, R-value, baseline drift, baseline offset, and amplitude.

In an aspect of the first embodiment, the method further includes providing one of an audible, visual, or tactile output to a user based on the stability of the sensor.

In an aspect of the first embodiment, the step of providing output based on the stability of the sensor includes indicating at least one of a numeric estimated analyte value, a directional trend of analyte concentration, and a graphical representation of an estimated analyte value.

In an aspect of the first embodiment, the step of receiving sensor data includes receiving sensor data from a substantially continuous glucose sensor.

In an aspect of the first embodiment, the step of receiving sensor data includes receiving sensor data from an implantable glucose sensor.

In an aspect of the first embodiment, the step of receiving sensor data includes receiving sensor data from subcutaneously implantable glucose sensor.

In an aspect of the first embodiment, the step of receiving reference data includes receiving reference data from a self-monitoring blood glucose test.

In an aspect of the first embodiment, the step of receiving reference data includes downloading reference data via a cabled connection.

In an aspect of the first embodiment, the step of receiving reference data includes downloading reference data via a wireless connection.

In an aspect of the first embodiment, the step of receiving reference data from a reference analyte monitor includes receiving within a receiver internal communication from a reference analyte monitor integral with the receiver.

In an aspect of the first embodiment, the step of forming a calibration set includes evaluating at least one matched data pair using inclusion criteria.

In an aspect of the first embodiment, the step of receiving sensor data includes receiving sensor data that has been algorithmically smoothed.

In an aspect of the first embodiment, the step of receiving sensor data includes algorithmically smoothing the received sensor data.

In an aspect of the first embodiment, the step of forming a calibration set includes including in the calibration set between one and six matched data pairs.

In an aspect of the first embodiment, the step of forming a calibration set includes including six matched data pairs.

In an aspect of the first embodiment, the step of forming a calibration set further includes determining a value for n, where n is greater than one and represents the number of matched data pairs in the calibration set.

In an aspect of the first embodiment, the step of determining a value for n is determined as a function of the frequency of the received reference data points and signal strength over time.

In a second embodiment, a system is provided for initializing a continuous analyte sensor, including: a sensor data module operatively connected to a continuous analyte sensor that receives a data stream including a plurality of time spaced sensor data points from the analyte sensor; a reference input module adapted to obtain reference data from a reference analyte monitor, including one or more reference data points; a processor module that forms one or more matched data pairs by matching reference data to substantially time corresponding sensor data and subsequently forms a calibration set including the one or more matched data pairs; and a start-up module associated with the processor module programmed to determine the stability of the continuous analyte sensor.

In an aspect of the second embodiment, the sensor data module is adapted to wirelessly receive sensor data points from the sensor.

In an aspect of the second embodiment, the start-up module is programmed to wait a predetermined time period between six hours and six weeks.

In an aspect of the second embodiment, the start-up module is programmed to evaluate at least two matched data pairs.

In an aspect of the second embodiment, the start-up module is programmed to evaluate one of pH, oxygen, hypochlorite, interfering species, correlation of matched pairs, R-value, baseline drift, baseline offset, and amplitude.

In an aspect of the second embodiment, the system further includes an output control module associated with the processor module and programmed to control output of sensor data.

In an aspect of the second embodiment, the output control module indicates at least one of a numeric estimated analyte value, a directional trend of analyte concentration, and a graphical representation of an estimated analyte value.

In an aspect of the second embodiment, the sensor data module is configured to receive sensor data from substantially the continuous glucose sensor.

In an aspect of the second embodiment, the sensor data module is configured to receive sensor data from an implantable glucose sensor.

In an aspect of the second embodiment, the sensor data module is configured to receive sensor data from subcutaneously implantable glucose sensor.

In an aspect of the second embodiment, the reference input module is configured to receive reference data from a self-monitoring blood glucose test.

In an aspect of the second embodiment, the reference input module is configured to download reference data via a cabled connection.

In an aspect of the second embodiment, the reference input module is configured to download reference data via a wireless connection.

In an aspect of the second embodiment, the system further includes a reference analyte monitor integral with the system and wherein the reference input module is configured to receive an internal communication from the reference analyte monitor.

In an aspect of the second embodiment, the processor module includes programming to evaluate at least one matched data pair using inclusion criteria.

In an aspect of the second embodiment, the reference input module is configured to receive sensor data that has been algorithmically smoothed.

In an aspect of the second embodiment, the reference input module is configured to algorithmically smooth the received sensor data.

In an aspect of the second embodiment, the calibration set includes between one and six matched data pairs.

In an aspect of the second embodiment, the calibration set includes six matched data pairs.

In an aspect of the second embodiment, the calibration set includes n matched data pairs, where n is greater than one.

In an aspect of the second embodiment, n is a function of the frequency of the received reference data points and signal strength over time.

In a third embodiment, a computer system is provided for initializing a continuous analyte sensor, the computer system including: a sensor data receiving module that receives sensor data from the substantially continuous analyte sensor via a receiver, including one or more sensor data points; a reference data receiving module that receives reference data from a reference analyte monitor, including one or more reference data points; a data matching module that forms one or more matched data pairs by matching reference data to substantially time corresponding sensor data; a calibration set module that forms a calibration set including at least one matched data pair; and a stability determination module that determines the stability of the continuous analyte sensor.

In an aspect of the third embodiment, the stability determination module includes a system for waiting a predetermined time period.

In an aspect of the third embodiment, the stability determination module evaluates at least two matched data pairs.

In an aspect of the third embodiment, the stability determination module evaluates one of pH, oxygen, hypochlorite, interfering species, correlation of matched pairs, R-value, baseline drift, baseline offset, and amplitude.

In an aspect of the third embodiment, the computer system further includes an interface control module that provides output to the user based on the stability of the sensor.

In an aspect of the third embodiment, the output from the interface control module includes at least one of a numeric estimated analyte value, an indication of directional trend of analyte concentration, and a graphical representation of an estimated analyte value.

In an aspect of the third embodiment, the reference data receiving module is adapted to receive sensor data from a substantially continuous glucose sensor.

In an aspect of the third embodiment, the reference data receiving module is adapted to receive sensor data from an implantable glucose sensor.

In an aspect of the third embodiment, the reference data receiving module is adapted to receive sensor data from a subcutaneously implantable glucose sensor.

In an aspect of the third embodiment, the reference data receiving module is adapted to receive sensor data from a self-monitoring blood glucose test.

In an aspect of the third embodiment, the reference data receiving module is adapted to receive sensor data from a cabled connection.

In an aspect of the third embodiment, the reference data receiving module is adapted to download reference data via a wireless connection.

In an aspect of the third embodiment, the reference data receiving module is adapted to receive reference data from an internal reference analyte monitor that is housed integrally the computer system.

In an aspect of the third embodiment, the calibration set module evaluates at least one matched data pair using inclusion criteria.

In an aspect of the third embodiment, the sensor data receiving module is adapted to receive sensor data that has been algorithmically smoothed.

In an aspect of the third embodiment, the computer system further includes a data smoothing module that smoothes the received sensor data.

In an aspect of the third embodiment, the calibration set module includes between one and six matched data pairs.

In an aspect of the third embodiment, the calibration set module includes six matched data pairs.

In an aspect of the third embodiment, the calibration set includes n number of matched data pairs, where n is greater than one.

In an aspect of the third embodiment, n is a function of the frequency of the received reference data points and signal strength over time.

In a fourth embodiment, method is provided for initializing a substantially continuous analyte sensor, the method including: receiving sensor data from a substantially continuous analyte sensor, including one or more sensor data points; receiving reference data from a reference analyte monitor, including one or more reference data points; forming one or more matched data pairs by matching reference data to substantially time corresponding sensor data; forming a calibration set including at least one matched data pair; determining stability of continuous analyte sensor; and outputting information reflective of the sensor data once a predetermined level of stability has been determined.

In a fifth embodiment, a system is provided for initializing a continuous analyte sensor, including: a sensor data module operatively linked to a continuous analyte sensor and configured to receive one or more sensor data points from the sensor; a reference input module adapted to obtain one or more reference data points; and a processor module associated with the sensor data module and the input module and programmed to match reference data points with time-matched sensor data points to form a calibration set including at least one matched data pair; and a start-up module associated with the processor module programmed to determine the stability of the continuous analyte sensor and output information reflective of the sensor data once a predetermined level of stability has been determined.

In a sixth embodiment, a computer system is provided for initializing a continuous analyte sensor, the system including: a sensor data receiving module that receives sensor data including one or more sensor data points from the substantially continuous analyte sensor via a receiver; a reference data receiving module for receiving reference data from a reference analyte monitor, including one or more reference data points; a data matching module for forming one or more matched data pairs by matching reference data to substantially time corresponding sensor data; a calibration set module for forming a calibration set including at least one matched data pair; a stability determination module for evaluating the stability of the continuous analyte sensor; and an interface control module that outputs information reflective of the sensor data once a predetermined level of stability has been determined.

In a seventh embodiment, a method for initializing a glucose sensor, the method including: receiving sensor data from the glucose sensor, including one or more sensor data points; receiving reference data from a reference glucose monitor, including one or more reference data points; forming one or more matched data pairs by matching reference data to substantially time corresponding sensor data; determining whether the glucose sensor has reached a predetermined level of stability.

In an eighth embodiment, a system is provided for initializing a continuous analyte sensor, including: a sensor data module operatively linked to a continuous analyte sensor and configured to receive one or more sensor data points from the sensor; a reference input module adapted to obtain one or more reference data points; and a processor module associated with the sensor data module and the input module and programmed to match reference data points with time-matched sensor data points to form a calibration set including at least one matched data pair; and a stability module associated with the processor module programmed to determine the stability of the continuous analyte sensor.

In a ninth embodiment, a method is provided for evaluating clinical acceptability of at least one of reference and sensor analyte data, the method including: receiving a data stream from an analyte sensor, including one or more sensor data points; receiving reference data from a reference analyte monitor, including one or more reference data points; and evaluating the clinical acceptability at least one of the reference and sensor analyte data using substantially time corresponding reference or sensor data, wherein the at least one of the reference and sensor analyte data is evaluated for deviation from its substantially time corresponding reference or sensor data and clinical risk associated with that deviation based on the glucose value indicated by at least one of the sensor and reference data.

In an aspect of the ninth embodiment, the method further includes providing an output through a user interface responsive to the clinical acceptability evaluation.

In an aspect of the ninth embodiment, the step of providing an output includes alerting the user based on the clinical acceptability evaluation.

In an aspect of the ninth embodiment, the step of providing an output includes altering the user interface based on the clinical acceptability evaluation.

In an aspect of the ninth embodiment, the step of altering the user interface includes at least one of providing color-coded information, trend information, directional information (e.g., arrows or angled lines), and/or fail-safe information.

In an aspect of the ninth embodiment, the step of evaluating the clinical acceptability includes using one of a Clarke Error Grid, a mean absolute difference calculation, a rate of change calculation, a consensus grid, and a standard clinical acceptance test.

In an aspect of the ninth embodiment, the method further includes requesting additional reference data if the clinical acceptability evaluation determines clinical unacceptability.

In an aspect of the ninth embodiment, the method further includes repeating the clinical acceptability evaluation step for the additional reference data.

In an aspect of the ninth embodiment, the method further includes a step of matching reference data to substantially time corresponding sensor data to form a matched pair after the clinical acceptability evaluation step.

In a tenth embodiment, a system is provided for evaluating clinical acceptability of at least one of reference and sensor analyte data, the method including: means for receiving a data stream from an analyte sensor, a plurality of time-spaced sensor data points; means for receiving reference data from a reference analyte monitor, including one or more reference data points; and means for evaluating the clinical acceptability of at least one of the reference and sensor analyte data using substantially time corresponding reference and sensor data, wherein the at least one of the reference and sensor analyte data is evaluated for deviation from its substantially time corresponding reference or sensor data and clinical risk associated with that deviation based on the glucose value indicated by at least one of the sensor and reference data.

In an aspect of the tenth embodiment, the system further includes means for providing an output based through a user interface responsive to the clinical acceptability evaluation.

In an aspect of the tenth embodiment, the means for providing an output includes means for alerting the user based on the clinical acceptability evaluation.

In an aspect of the tenth embodiment, the means for providing an output includes means for altering the user interface based on the clinical acceptability evaluation.

In an aspect of the tenth embodiment, the means for altering the user interface includes at least one of providing color-coded information, trend information, directional information (e.g., arrows or angled lines), and/or fail-safe information.

In an aspect of the tenth embodiment, the means for evaluating the clinical acceptability includes using one of a Clarke Error Grid, a mean absolute difference calculation, a rate of change calculation, a consensus grid, and a standard clinical acceptance test.

In an aspect of the tenth embodiment, the system further includes means for requesting additional reference data if the clinical acceptability evaluation determines clinical unacceptability.

In an aspect of the tenth embodiment, the system further includes means for repeated the clinical acceptability evaluation for the additional reference data.

In an aspect of the tenth embodiment, the system further includes means for matching reference data to substantially time corresponding sensor data to form a matched data pair after the clinical acceptability evaluation.

In an eleventh embodiment, a computer system is provided for evaluating clinical acceptability of at least one of reference and sensor analyte data, the computer system including: a sensor data receiving module that receives a data stream including a plurality of time spaced sensor data points from a substantially continuous analyte sensor; a reference data receiving module that receives reference data from a reference analyte monitor, including one or more reference data points; and a clinical acceptability evaluation module that evaluates at least one of the reference and sensor analyte data using substantially time corresponding reference and sensor data, wherein the at least one of the reference and sensor analyte data is evaluated for deviation from its substantially time corresponding reference or sensor data and clinical risk associated with that deviation based on the glucose value indicated by at least one of the sensor and reference data.

In an aspect of the eleventh embodiment, the computer system further includes an interface control module that controls the user interface based on the clinical acceptability evaluation.

In an aspect of the eleventh embodiment, the interface control module alerts the user based on the clinical acceptability evaluation.

In an aspect of the eleventh embodiment, the interface control module alters the user interface based on the clinical acceptability evaluation.

In an aspect of the eleventh embodiment, the interface control module alters the user interface by providing at least one of providing color-coded information, trend information, directional information (e.g., arrows or angled lines), and/or fail-safe information.

In an aspect of the eleventh embodiment, the clinical acceptability evaluation module uses one of a Clarke Error Grid, a mean absolute difference calculation, a rate of change calculation, a consensus grid, and a standard clinical acceptance test to evaluate clinical acceptability.

In an aspect of the eleventh embodiment, the interface control module that requests additional reference data if the clinical acceptability evaluation determines clinical unacceptability.

In an aspect of the eleventh embodiment, the interface control module evaluates the additional reference data using clinical acceptability evaluation module.

In an aspect of the eleventh embodiment, the computer system further includes a data matching module that matches clinically acceptable reference data to substantially time corresponding clinically acceptable sensor data to form a matched pair.

In a twelfth embodiment, a method is provided for evaluating clinical acceptability of at least one of reference and sensor analyte data, the method including: receiving a data stream from an analyte sensor, including one or more sensor data points; receiving reference data from a reference analyte monitor, including one or more reference data points; evaluating the clinical acceptability at least one of the reference and sensor analyte data using substantially time corresponding reference and sensor data, wherein the at least one of the reference and sensor analyte data is evaluated for deviation from its substantially time corresponding reference or sensor data and clinical risk associated with that deviation based on the glucose value indicated by at least one of the sensor and reference data; and providing an output through a user interface responsive to the clinical acceptability evaluation.

In an thirteenth embodiment, a method is provided for evaluating clinical acceptability of at least one of reference and sensor analyte data, the method including: receiving a data stream from an analyte sensor, including one or more sensor data points; receiving reference data from a reference analyte monitor, including one or more reference data points; and evaluating the clinical acceptability at least one of the reference and sensor analyte data using substantially time corresponding reference and sensor data, including using one of a Clarke Error Grid, a mean absolute difference calculation, a rate of change calculation, and a consensus grid.

In an fourteenth embodiment, a computer system is provided for evaluating clinical acceptability of at least one of reference and sensor analyte data, the computer system including: a sensor data module that receives a data stream including a plurality of time spaced sensor data points from a substantially continuous analyte sensor; a reference input module that receives reference data from a reference analyte monitor, including one or more reference data points; a clinical module that evaluates at least one of the reference and sensor analyte data using substantially time corresponding reference and sensor data, wherein the at least one of the reference and sensor analyte data is evaluated for deviation from its substantially time corresponding reference or sensor data and clinical risk associated with that deviation based on the glucose value indicated by at least one of the sensor and reference data; and an interface control module that controls the user interface based on the clinical acceptability evaluation.

In an fifteenth embodiment, a computer system is provided for evaluating clinical acceptability of at least one of reference and sensor analyte data, the computer system including:

a sensor data module that receives a data stream including a plurality of time spaced sensor data points from a substantially continuous analyte sensor; a reference input module that receives reference data from a reference analyte monitor, including one or more reference data points; and a clinical module that evaluates at least one of the reference and sensor analyte data with substantially time corresponding reference and sensor data, wherein the clinical module uses one of a Clarke Error Grid, a mean absolute difference calculation, a rate of change calculation, a consensus grid, and a standard clinical acceptance test to evaluate clinical acceptability.

In an sixteenth embodiment, a computer system is provided for evaluating clinical acceptability of at least one of reference and sensor analyte data, the computer system including: a sensor data module that receives a data stream including a plurality of time spaced sensor data points from a substantially continuous analyte sensor via a receiver; a reference input module that receives reference data from a reference analyte monitor, including one or more reference data points; and a clinical module that uses a Clarke Error Grid to evaluate the clinical acceptability at least one of the reference and sensor analyte data using substantially time corresponding reference and sensor data; and a fail-safe module that controls the user interface responsive to the clinical module evaluating clinical unacceptability.

In an seventeenth embodiment, a method is provided for evaluating clinical acceptability of at least one of reference and sensor glucose data, the method including: receiving a data stream from an analyte sensor, including one or more sensor data points; receiving reference data from a reference glucose monitor, including one or more reference data points; evaluating the clinical acceptability at least one of the reference and sensor glucose data using substantially time corresponding reference and sensor data, wherein the at least one of the reference and sensor analyte data is evaluated for deviation from its substantially time corresponding reference or sensor data and clinical risk associated with that deviation based on the glucose value indicated by at least one of the sensor and reference data; and a fail-safe module that controls the user interface responsive to the clinical module evaluating clinical unacceptability.

In an eighteenth embodiment, a method is provided for maintaining calibration of a substantially continuous analyte sensor, the method including: receiving a data stream from an analyte sensor, including one or more sensor data points; receiving reference data from a reference analyte monitor, including two or more reference data points; providing at least two matched data pairs by matching reference analyte data to substantially time corresponding sensor data; forming a calibration set including the at least two matching data pairs; creating a conversion function based on the calibration set; converting sensor data into calibrated data using the conversion function; subsequently obtaining one or more additional reference data points and creating one or more new matched data pairs; evaluating the calibration set when the new matched data pair is created, wherein evaluating the calibration set includes at least one of 1) ensuring matched data pairs in the calibration set span a predetermined time range, 2) ensuring matched data pairs in the calibration set are no older than a predetermined value, 3) ensuring the calibration set has substantially distributed high and low matched data pairs over the predetermined time range, and 4) allowing matched data pairs only within a predetermined range of analyte values; and subsequently modifying the calibration set if such modification is required by the evaluation.

In an aspect of the eighteenth embodiment, the step of evaluating the calibration set further includes at least one of evaluating a rate of change of the analyte concentration, evaluating a congruence of respective sensor and reference data in the matched data pairs, and evaluating physiological changes.

In an aspect of the eighteenth embodiment, the step of evaluating the calibration set includes evaluating only the new matched data pair.

In an aspect of the eighteenth embodiment, the step of evaluating the calibration set includes evaluating all of the matched data pairs in the calibration set and the new matched data pair.

In an aspect of the eighteenth embodiment, the step of evaluating the calibration set includes evaluating combinations of matched data pairs from the calibration set and the new matched data pair.

In an aspect of the eighteenth embodiment, the step of receiving sensor data includes receiving a data stream from a long-term implantable analyte sensor.

In an aspect of the eighteenth embodiment, the step of receiving sensor data includes receiving a data stream that has been algorithmically smoothed.

In an aspect of the eighteenth embodiment, the step of receiving sensor data stream includes algorithmically smoothing the data stream.

In an aspect of the eighteenth embodiment, the step of receiving reference data includes downloading reference data via a cabled connection.

In an aspect of the eighteenth embodiment, the step of receiving reference data includes downloading reference data via a wireless connection.

In an aspect of the eighteenth embodiment, the step of receiving reference data from a reference analyte monitor includes receiving within a receiver internal communication from a reference analyte monitor integral with the receiver.

In an aspect of the eighteenth embodiment, the reference analyte monitor includes self-monitoring of blood analyte.

In an aspect of the eighteenth embodiment, the step of creating a conversion function includes linear regression.

In an aspect of the eighteenth embodiment, the step of creating a conversion function includes non-linear regression.

In an aspect of the eighteenth embodiment, the step of forming a calibration set includes including in the calibration set between one and six matched data pairs.

In an aspect of the eighteenth embodiment, the step of forming a calibration set includes including six matched data pairs.

In an aspect of the eighteenth embodiment, the step of forming a calibration set further includes determining a value for n, where n is greater than one and represents the number of matched data pairs in the calibration set.

In an aspect of the eighteenth embodiment, the step of determining a value for n is determined as a function of the frequency of the received reference data points and signal strength over time.

In an aspect of the eighteenth embodiment, the method further includes determining a set of matching data pairs from the evaluation of the calibration set and re-forming a calibration set.

In an aspect of the eighteenth embodiment, the method further includes repeating the step of re-creating the conversion function using the re-formed calibration set.

In an aspect of the eighteenth embodiment, the method further includes converting sensor data into calibrated data using the re-created conversion function.

In a nineteenth embodiment, a system is provided for maintaining calibration of a substantially continuous analyte sensor, the system including: means for receiving a data stream from an analyte sensor, a plurality of time-spaced sensor data points; means for receiving reference data from a reference analyte monitor, including two or more reference data points; means for providing two or more matched data pairs by matching reference analyte data to substantially time corresponding sensor data; means for forming a calibration set including at least two matched data pair; means for creating a conversion function based on the calibration set; means for converting sensor data into calibrated data using the conversion function; subsequently obtaining one or more additional reference data points and creating one or more new matched data pairs; means for evaluating the calibration set when the new matched data pair is created, wherein evaluating the calibration set includes at least one of 1) ensuring matched data pairs in the calibration set span a predetermined time range, 2) ensuring matched data pairs in the calibration set are no older than a predetermined value, 3) ensuring the calibration set has substantially distributed high and low matched data pairs over the predetermined time range, and 4) allowing matched data pairs only within a predetermined range of analyte values; and means for modifying the calibration set if such modification is required by the evaluation.

In an aspect of the nineteenth embodiment, the means for evaluating the calibration set further includes at least one of means for evaluating a rate of change of the analyte concentration, means for evaluating a congruence of respective sensor and reference data in matched data pairs; and means for evaluating physiological changes.

In an aspect of the nineteenth embodiment, the means for evaluating the calibration set includes means for evaluating only the one or more new matched data pairs.

In an aspect of the nineteenth embodiment, the means for evaluating the calibration set includes means for evaluating all of the matched data pairs in the calibration set and the one or more new matched data pairs.

In an aspect of the nineteenth embodiment, the means for evaluating the calibration set includes means for evaluating combinations of matched data pairs from the calibration set and the one or more new matched data pair.

In an aspect of the nineteenth embodiment, the means for receiving sensor data includes means for receiving sensor data from a long-term implantable analyte sensor.

In an aspect of the nineteenth embodiment, the means for receiving sensor data includes means for receiving sensor data that has been algorithmically smoothed.

In an aspect of the nineteenth embodiment, the means for receiving sensor data includes means for algorithmically smoothing the receiving sensor data.

In an aspect of the nineteenth embodiment, the means for receiving reference data includes means for downloading reference data via a cabled connection.

In an aspect of the nineteenth embodiment, the means for receiving reference data includes means for downloading reference data via a wireless connection.

In an aspect of the nineteenth embodiment, the means for receiving reference data from a reference analyte monitor includes means for receiving within a receiver internal communication from a reference analyte monitor integral with the receiver.

In an aspect of the nineteenth embodiment, the means for receiving reference data includes means for receiving from a self-monitoring of blood analyte.

In an aspect of the nineteenth embodiment, the means for creating a conversion function includes means for performing linear regression.

In an aspect of the nineteenth embodiment, the means for creating a conversion function includes means for performing non-linear regression.

In an aspect of the nineteenth embodiment, the means for forming a calibration set includes including in the calibration set between one and six matched data pairs.

In an aspect of the nineteenth embodiment, the means for forming a calibration set includes including in the calibration set six matched data pairs.

In an aspect of the nineteenth embodiment, the means for forming a calibration set further includes determining a value for n, where n is greater than one and represents the number of matched data pairs in the calibration set.

In an aspect of the nineteenth embodiment, the means for determining a value for n is determined as a function of the frequency of the received reference data points and signal strength over time.

In an aspect of the nineteenth embodiment, the system further includes means for determining a set of matching data pairs from the evaluation of the calibration set and re-forming a calibration set.

In an aspect of the nineteenth embodiment, the system further includes the means for repeating the set of creating the conversion function using the re-formed calibration set.

In an aspect of the nineteenth embodiment, the system further includes means for converting sensor data into calibrated data using the re-created conversion function.

In a twentieth embodiment, a computer system is provided for maintaining calibration of a substantially continuous analyte sensor, the computer system including: a sensor data receiving module that receives a data stream including a plurality of time spaced sensor data points from a substantially continuous analyte sensor; a reference data receiving module that receives reference data from a reference analyte monitor, including two or more reference data points; a data matching module that forms two or more matched data pairs by matching reference data to substantially time corresponding sensor data; a calibration set module that forms a calibration set including at least two matched data pairs; a conversion function module that creates a conversion function using the calibration set; a sensor data transformation module that converts sensor data into calibrated data using the conversion function; and a calibration evaluation module that evaluates the calibration set when the new matched data pair is provided, wherein evaluating the calibration set includes at least one of 1) ensuring matched data pairs in the calibration set span a predetermined time period, 2) ensuring matched data pairs in the calibration set are no older than a predetermined value, 3) ensuring the calibration set has substantially distributed high and low matched data pairs over a predetermined time range, and 4) allowing matched data pairs only within a predetermined range of analyte values, wherein the conversion function module is programmed to re-create the conversion function of such modification is required by the calibration evaluation module.

In an aspect of the twentieth embodiment, the evaluation calibration module further evaluates at least one of a rate of change of the analyte concentration, a congruence of respective sensor and reference data in matched data pairs; and physiological changes.

In an aspect of the twentieth embodiment, the evaluation calibration module evaluates only the new matched data pair.

In an aspect of the twentieth embodiment, the evaluation calibration module evaluates all of the matched data pairs in the calibration set and the new matched data pair.

In an aspect of the twentieth embodiment, the evaluation calibration module evaluates combinations of matched data pairs from the calibration set and the new matched data pair.

In an aspect of the twentieth embodiment, the sensor data receiving module receives the data stream from a long-term implantable analyte sensor.

In an aspect of the twentieth embodiment, the sensor data receiving module receives an algorithmically smoothed data stream.

In an aspect of the twentieth embodiment, the sensor data receiving module includes programming to smooth the data stream.

In an aspect of the twentieth embodiment, the reference data receiving module downloads reference data via a cabled connection.

In an aspect of the twentieth embodiment, the reference data receiving module downloads reference data via a wireless connection.

In an aspect of the twentieth embodiment, the reference data receiving module receives within a receiver internal communication from a reference analyte monitor integral with the receiver.

In an aspect of the twentieth embodiment, the reference data receiving module receives reference data from a self-monitoring of blood analyte.

In an aspect of the twentieth embodiment, the conversion function module includes programming that performs linear regression.

In an aspect of the twentieth embodiment, the conversion function module includes programming that performs non-linear regression.

In an aspect of the twentieth embodiment, the calibration set module includes in the calibration set between one and six matched data pairs.

In an aspect of the twentieth embodiment, the calibration set module includes in the calibration set six matched data pairs.

In an aspect of the twentieth embodiment, the calibration set module further includes programming for determining a value for n, where n is greater than one and represents the number of matched data pairs in the calibration set.

In an aspect of the twentieth embodiment, the programming for determining a value for n determines n as a function of the frequency of the received reference data points and signal strength over time.

In an aspect of the twentieth embodiment, data matching module further includes programming to re-form the calibration set based on the calibration evaluation.

In an aspect of the twentieth embodiment, the conversion function module further includes programming to re-create the conversion function based on the re-formed calibration set.

In an aspect of the twentieth embodiment, the sensor data transformation module further including programming for converting sensor data into calibrated using the re-created conversion function.

In a twenty-first embodiment, a method is provided for maintaining calibration of a glucose sensor, the method including: receiving a data stream from an analyte sensor, including one or more sensor data points; receiving reference data from a reference analyte monitor, including two or more reference data points; providing at least two matched data pairs by matching reference analyte data to substantially time corresponding sensor data; forming a calibration set including the at least two matching data pairs; creating a conversion function based on the calibration set; subsequently obtaining one or more additional reference data points and creating one or more new matched data pairs; and evaluating the calibration set when the new matched data pair is created, wherein evaluating the calibration set includes at least one of 1) ensuring matched data pairs in the calibration set span a predetermined time range, 2) ensuring matched data pairs in the calibration set are no older than a predetermined value, 3) ensuring the calibration set has substantially distributed high and low matched data pairs over the predetermined time range, and 4) allowing matched data pairs only within a predetermined range of analyte values.

In a twenty-second embodiment, a computer system is provided for maintaining calibration of a glucose sensor, the computer system including: a sensor data module that receives a data stream including a plurality of time spaced sensor data points from a substantially continuous analyte sensor; a reference input module that receives reference data from a reference analyte monitor, including two or more reference data points; a processor module that forms two or more matched data pairs by matching reference data to substantially time corresponding sensor data and subsequently forms a calibration set including the two or more matched data pairs; and a calibration evaluation module that evaluates the calibration set when the new matched data pair is provided, wherein evaluating the calibration set includes at least one of 1) ensuring matched data pairs in the calibration set span a predetermined time period, 2) ensuring matched data pairs in the calibration set are no older than a predetermined value, 3) ensuring the calibration set has substantially distributed high and low matched data pairs over a predetermined time range, and 4) allowing matched data pairs only within a predetermined range of analyte values, wherein the conversion function module is programmed to re-create the conversion function of such modification is required by the calibration evaluation module.

In a twenty-third embodiment, a method is provided for evaluating the quality of a calibration of an analyte sensor, the method including: receiving a data stream from an analyte sensor, including one or more sensor data points; receiving reference data from a reference analyte monitor, including two or more reference data points; providing at least two matched data pairs by matching reference analyte data to substantially time corresponding sensor data; forming a calibration set including the at least two matching data pairs; creating a conversion function based on the calibration set; receiving additional sensor data from the analyte sensor; converting sensor data into calibrated data using the conversion function; and evaluating the quality of the calibration set using a data association function.

In an aspect of the twenty-third embodiment, the step of receiving sensor data includes receiving a data stream that has been algorithmically smoothed.

In an aspect of the twenty-third embodiment, the step of receiving sensor data includes algorithmically smoothing the data stream.

In an aspect of the twenty-third embodiment, the step of receiving sensor data includes receiving sensor data from a substantially continuous glucose sensor.

In an aspect of the twenty-third embodiment, the step of receiving sensor data includes receiving sensor data from an implantable glucose sensor.

In an aspect of the twenty-third embodiment, the step of receiving sensor data includes receiving sensor data from a subcutaneously implantable glucose sensor.

In an aspect of the twenty-third embodiment, the step of receiving reference data includes receiving reference data from a self-monitoring blood glucose test.

In an aspect of the twenty-third embodiment, the step of receiving reference data includes downloading reference data via a cabled connection.

In an aspect of the twenty-third embodiment, the step of receiving reference data includes downloading reference data via a wireless connection.

In an aspect of the twenty-third embodiment, the step of receiving reference data from a reference analyte monitor includes receiving within a receiver internal communication from a reference analyte monitor integral with the receiver.

In an aspect of the twenty-third embodiment, the step of evaluating the quality of the calibration set based on a data association function includes performing one of linear regression, non-linear regression, rank correlation, least mean square fit, mean absolute deviation, and mean absolute relative difference.

In an aspect of the twenty-third embodiment, the step of evaluating the quality of the calibration set based on a data association function includes performing linear least squares regression.

In an aspect of the twenty-third embodiment, the step of evaluating the quality of the calibration set based on a data association function includes setting a threshold of data association.

In an aspect of the twenty-third embodiment, the step of evaluating the quality of the calibration set based on data association includes performing linear least squares regression and wherein the step of setting a threshold hold includes an R-value threshold of 0.79.

In an aspect of the twenty-third embodiment, the method further includes providing an output to a user interface responsive to the quality of the calibration set.

In an aspect of the twenty-third embodiment, the step of providing an output includes displaying analyte values to a user dependent upon the quality of the calibration.

In an aspect of the twenty-third embodiment, the step of providing an output includes alerting the dependent upon the quality of the calibration.

In an aspect of the twenty-third embodiment, the step of providing an output includes altering the user interface dependent upon the quality of the calibration.

In an aspect of the twenty-third embodiment, the step of providing an output includes at least one of providing color-coded information, trend information, directional information (e.g., arrows or angled lines), and/or fail-safe information.

In a twenty-fourth embodiment, a system is provided for evaluating the quality of a calibration of an analyte sensor, the system including: means for receiving a data stream from an analyte sensor, a plurality of time-spaced sensor data points; means for receiving reference data from a reference analyte monitor, including two or more reference data points; means for providing two or more matched data pairs by matching reference analyte data to substantially time corresponding sensor data; means for forming a calibration set including at least two matched data pair; means for creating a conversion function based on the calibration set; means for converting sensor data into calibrated data using the conversion function; means for evaluating the quality of the calibration set based on a data association function.

In an aspect of the twenty-fourth embodiment, the means for receiving sensor data includes means for receiving sensor data that has been algorithmically smoothed.

In an aspect of the twenty-fourth embodiment, the means for receiving sensor data includes means for algorithmically smoothing the receiving sensor data.

In an aspect of the twenty-fourth embodiment, the means for receiving sensor data includes means for receiving sensor data from substantially continuous glucose sensor.

In an aspect of the twenty-fourth embodiment, the means for receiving sensor data includes means for receiving sensor data from an implantable glucose sensor.

In an aspect of the twenty-fourth embodiment, the means for receiving sensor data includes means for receiving sensor data from subcutaneously implantable glucose sensor.

In an aspect of the twenty-fourth embodiment, the means for receiving reference data includes means for receiving reference data from a self-monitoring blood glucose test.

In an aspect of the twenty-fourth embodiment, the means for receiving reference data includes means for downloading reference data via a cabled connection.

In an aspect of the twenty-fourth embodiment, the means for receiving reference data includes means for downloading reference data via a wireless connection.

In an aspect of the twenty-fourth embodiment, the means for receiving reference data from a reference analyte monitor includes means for receiving within a receiver internal communication from a reference analyte monitor integral with the receiver.

In an aspect of the twenty-fourth embodiment, the means for evaluating the quality of the calibration set includes means for performing one of linear regression, non-linear regression, rank correlation, least mean square fit, mean absolute deviation, and mean absolute relative difference.

In an aspect of the twenty-fourth embodiment, the means for evaluating the quality of the calibration set includes means for performing linear least squares regression.

In an aspect of the twenty-fourth embodiment, the means for evaluating the quality of the calibration set includes means for setting a threshold of data association.

In an aspect of the twenty-fourth embodiment, the means for evaluating the quality of the calibration set includes means for performing linear least squares regression and wherein the means for setting a threshold hold includes an R-value threshold of 0.71.

In an aspect of the twenty-fourth embodiment, the system further includes means for providing an output to a user interface responsive to the quality of the calibration set.

In an aspect of the twenty-fourth embodiment, the means for providing an output includes means for displaying analyte values to a user dependent upon the quality of the calibration.

In an aspect of the twenty-fourth embodiment, the means for providing an output includes means for alerting the dependent upon the quality of the calibration.

In an aspect of the twenty-fourth embodiment, the means for providing an output includes means for altering the user interface dependent upon the quality of the calibration.

In an aspect of the twenty-fourth embodiment, the means for providing an output includes at least one of providing color-coded information, trend information, directional information (e.g., arrows or angled lines), and/or fail-safe information.

In a twenty-fifth embodiment, a computer system is provided for evaluating the quality of a calibration of an analyte sensor, the computer system including: a sensor data receiving module that receives a data stream including a plurality of time spaced sensor data points from a substantially continuous analyte sensor; a reference data receiving module that receives reference data from a reference analyte monitor, including two or more reference data points; a data matching module that forms two or more matched data pairs by matching reference data to substantially time corresponding sensor data; a calibration set module that forms a calibration set including at least two matched data pairs; a conversion function module that creates a conversion function using the calibration set; a sensor data transformation module that converts sensor data into calibrated data using the conversion function; and a quality evaluation module that evaluates the quality of the calibration set based on a data association function.

In an aspect of the twenty-fifth embodiment, the sensor data receiving module receives sensor data that has been algorithmically smoothed.

In an aspect of the twenty-fifth embodiment, the computer system further includes a data smoothing module that algorithmically smoothes sensor data received from the sensor data receiving module.

In an aspect of the twenty-fifth embodiment, the sensor data receiving module is adapted to receive sensor data from substantially continuous glucose sensor.

In an aspect of the twenty-fifth embodiment, the sensor data receiving module is adapted to receive sensor data from an implantable glucose sensor.

In an aspect of the twenty-fifth embodiment, the sensor data receiving module is adapted to receive sensor data from subcutaneously implantable glucose sensor.

In an aspect of the twenty-fifth embodiment, the reference data receiving module is adapted to receive reference data from a self-monitoring blood glucose test.

In an aspect of the twenty-fifth embodiment, the reference data receiving module is adapted to download reference data via a cabled connection.

In an aspect of the twenty-fifth embodiment, the reference data receiving module is adapted to download reference data via a wireless connection.

In an aspect of the twenty-fifth embodiment, the reference data receiving module is adapted to receive reference data from a reference analyte monitor integral with the receiver.

In an aspect of the twenty-fifth embodiment, the quality evaluation module performs one of linear regression, non-linear regression, rank correlation, least mean square fit, mean absolute deviation, and mean absolute relative difference to evaluate calibration set quality.

In an aspect of the twenty-fifth embodiment, the quality evaluation module performs linear least squares regression.

In an aspect of the twenty-fifth embodiment, the quality evaluation module sets a threshold for the data association function.

In an aspect of the twenty-fifth embodiment, the quality evaluation module performs linear least squares regression and wherein the threshold of the data association function includes an R-value threshold of at least 0.79.

In an aspect of the twenty-fifth embodiment, the computer system further includes an interface control module that controls the user interface based on the quality of the calibration set.

In an aspect of the twenty-fifth embodiment, the interface control module displays analyte values to a user dependent upon the quality of the calibration set.

In an aspect of the twenty-fifth embodiment, the interface control module alerts the user based upon the quality of the calibration set.

In an aspect of the twenty-fifth embodiment, the interface control module alters the user interface based upon the quality of the calibration set.

In an aspect of the twenty-fifth embodiment, the interface control module provides at least one of color-coded information, trend information, directional information (e.g., arrows or angled lines), and/or fail-safe information.

In a twenty-sixth embodiment, a method is provided for evaluating the quality of a calibration of an analyte sensor, the method including: receiving a data stream from an analyte sensor, including one or more sensor data points; receiving reference data from a reference analyte monitor, including two or more reference data points; providing at least two matched data pairs by matching reference analyte data to substantially time corresponding sensor data; forming a calibration set including the at least two matching data pairs; creating a conversion function based on the calibration set; receiving additional sensor data from the analyte sensor; converting sensor data into calibrated data using the conversion function; and evaluating the quality of the calibration set based on a data association function selected from the group consisting of linear regression, non-linear regression, rank correlation, least mean square fit, mean absolute deviation, and mean absolute relative difference.

In a twenty-seventh embodiment, a method is provided for evaluating the quality of a calibration of an analyte sensor, the method including: receiving a data stream from an analyte sensor, including one or more sensor data points; receiving reference data from a reference analyte monitor, including two or more reference data points; providing at least two matched data pairs by matching reference analyte data to substantially time corresponding sensor data; forming a calibration set including the at least two matching data pairs; creating a conversion function based on the calibration set; receiving additional sensor data from the analyte sensor; converting sensor data into calibrated data using the conversion function; evaluating the quality of the calibration set using a data association function; and providing an output to a user interface responsive to the quality of the calibration set.

In a twenty-eighth embodiment, a computer system is provided for evaluating the quality of a calibration of an analyte sensor, the computer system including: a sensor data module that receives a data stream including a plurality of time spaced sensor data points from a substantially continuous analyte sensor; a reference input module that receives reference data from a reference analyte monitor, including two or more reference data points; a processor module that forms two or more matched data pairs by matching reference data to substantially time corresponding sensor data and subsequently forms a calibration set including the two or more matched data pairs; and a conversion function module that creates a conversion function using the calibration set; a sensor data transformation module that converts sensor data into calibrated data using the conversion function; a quality evaluation module that evaluates the quality of the calibration set based on a data association selected from the group consisting of linear regression, non-linear regression, rank correlation, least mean square fit, mean absolute deviation, and mean absolute relative difference.

In a twenty-ninth embodiment, a computer system is provided for evaluating the quality of a calibration of an analyte sensor, the computer system including: a sensor data module that receives a data stream including a plurality of time spaced sensor data points from a substantially continuous analyte sensor; a reference input module that receives reference data from a reference analyte monitor, including two or more reference data points; a processor module that forms two or more matched data pairs by matching reference data to substantially time corresponding sensor data and subsequently forms a calibration set including the two or more matched data pairs; and a conversion function module that creates a conversion function using the calibration set; a sensor data transformation module that converts sensor data into calibrated data using the conversion function; a quality evaluation module that evaluates the quality of the calibration set based on data association; and a fail-safe module that controls the user interface based on the quality of the calibration set.

In a thirtieth embodiment, a method is provided for evaluating the quality of a calibration of a glucose sensor, the method including: receiving sensor data from a glucose sensor, including one or more sensor data points; receiving reference data from a reference glucose monitor, including one or more reference data points; providing one or more matched data pairs by matched reference glucose data to substantially time corresponding sensor data; forming a calibration set including at least one matched data pair; and evaluating the quality of the calibration set based on data association.

DETAILED DESCRIPTION OF THE PREFERRED EMBODIMENT

Figure 1:
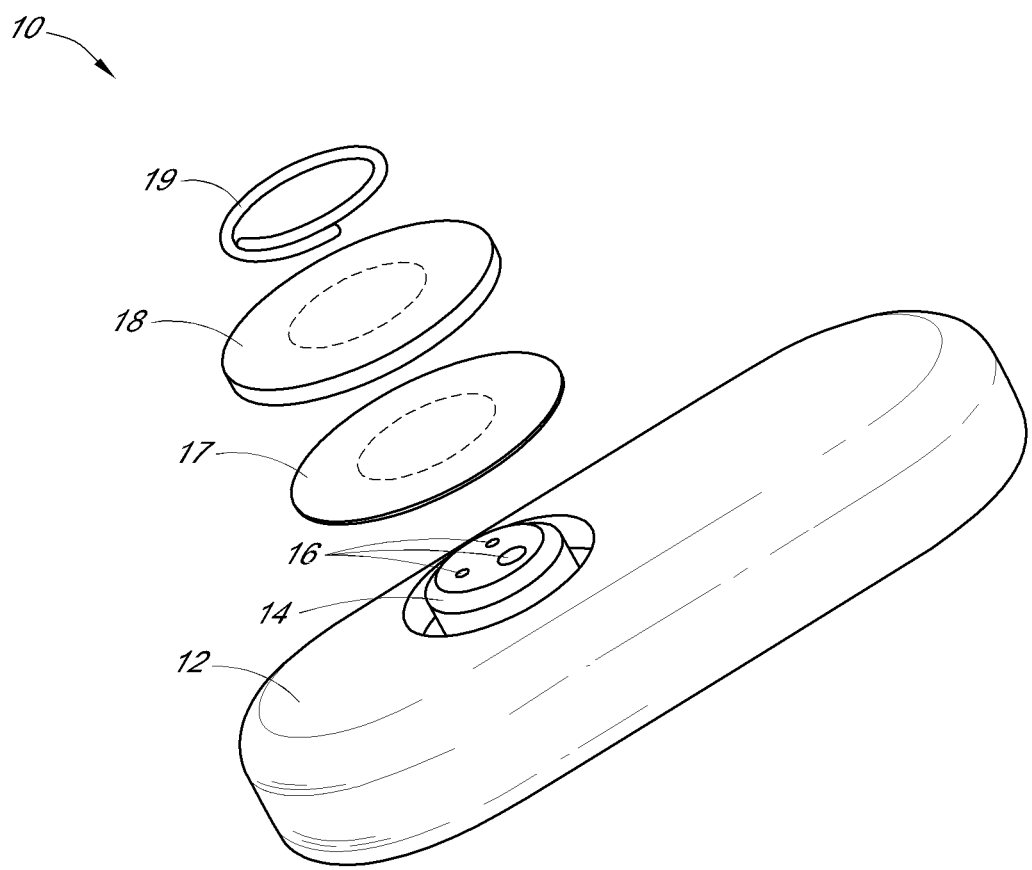
FIG. 1 is an exploded perspective view of a glucose sensor in one embodiment.

The following description and examples illustrate some exemplary embodiments of the disclosed invention in detail. Those of skill in the art will recognize that there are numerous variations and modifications of this invention that are encompassed by its scope. Accordingly, the description of a certain exemplary embodiment should not be deemed to limit the scope of the present invention.

DEFINITIONS

In order to facilitate an understanding of the disclosed invention, a number of terms are defined below.

The term "analyte," as used herein, is a broad term and is used in its ordinary sense, including, without limitation, to refer to a substance or chemical constituent in a biological fluid (for example, blood, interstitial fluid, cerebral spinal fluid, lymph fluid or urine) that can be analyzed. Analytes may include naturally occurring substances, artificial substances, metabolites, and/or reaction products. In some embodiments, the analyte for measurement by the sensor heads, devices, and methods is analyte. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobinopathies, A,S,C,E, D-Punjab, beta-thalassemia, hepatitis B virus, HCMV, HIV-1, HTLV-1, Leber hereditary optic neuropathy, MCAD, RNA, PKU, Plasmodium vivax, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17 alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, Dracunculus medinensis, Echinococcus granulosus, Entamoeba histolytica, enterovirus, Giardia duodenalisa, Helicobacter pylori, hepatitis B virus, herpes virus, HIV-1, IgE (atopic disease), influenza virus, Leishmania donovani, leptospira, measles/mumps/rubella, Mycobacterium leprae, Mycoplasma pneumoniae, Myoglobin, Onchocerca volvulus, parainfluenza virus, Plasmodium falciparum, poliovirus, Pseudomonas aeruginosa, respiratory syncytial virus, rickettsia (scrub typhus), Schistosoma mansoni, Toxoplasma gondii, Trepenoma pallidium, Trypanosoma cruzi/rangeli, vesicular stomatis virus, Wuchereria bancrofti, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins and hormones naturally occurring in blood or interstitial fluids may also constitute analytes in certain embodiments. The analyte may be naturally present in the biological fluid, for example, a metabolic product, a hormone, an antigen, an antibody, and the like. Alternatively, the analyte may be introduced into the body, for example, a contrast agent for imaging, a radioisotope, a chemical agent, a fluorocarbon-based synthetic blood, or a drug or pharmaceutical composition, including but not limited to insulin; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbituates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body may also be analyzed, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA).

The terms "operably connected" and "operably linked," as used herein, are broad terms and are used in their ordinary sense, including, without limitation, one or more components being linked to another component(s) in a manner that allows transmission of signals between the components, e.g., wired or wirelessly. For example, one or more electrodes may be used to detect the amount of analyte in a sample and convert that information into a signal; the signal may then be transmitted to an electronic circuit means. In this case, the electrode is "operably linked" to the electronic circuitry.

The term "EEPROM," as used herein, is a broad term and is used in its ordinary sense, including, without limitation, electrically erasable programmable read-only memory, which is user-modifiable read-only memory (ROM) that can be erased and reprogrammed (e.g., written to) repeatedly through the application of higher than normal electrical voltage.

The term "SRAM," as used herein, is a broad term and is used in its ordinary sense, including, without limitation, static random access memory (RAM) that retains data bits in its memory as long as power is being supplied.

The term "A/D Converter," as used herein, is a broad term and is used in its ordinary sense, including, without limitation, hardware that converts analog signals into digital signals.

The term "microprocessor," as used herein, is a broad term and is used in its ordinary sense, including, without limitation a computer system or processor designed to perform arithmetic and logic operations using logic circuitry that responds to and processes the basic instructions that drive a computer.

The term "RF transceiver," as used herein, is a broad term and is used in its ordinary sense, including, without limitation, a radio frequency transmitter and/or receiver for transmitting and/or receiving signals.

The term "jitter" as used herein, is a broad term and is used in its ordinary sense, including, without limitation, uncertainty or variability of waveform timing, which may be cause by ubiquitous noise caused by a circuit and/or environmental effects; jitter can be seen in amplitude, phase timing, or the width of the signal pulse.

The term "raw data signal," as used herein, is a broad term and is used in its ordinary sense, including, without limitation, an analog or digital signal directly related to the measured analyte from the analyte sensor. In one example, the raw data signal is digital data in "counts" converted by an A/D converter from an analog signal (e.g., voltage or amps) representative of an analyte concentration.

The term "counts," as used herein, is a broad term and is used in its ordinary sense, including, without limitation, a unit of measurement of a digital signal. In one example, a raw data signal measured in counts is directly related to a voltage (converted by an A/D converter), which is directly related to current.

The term "analyte sensor," as used herein, is a broad term and is used in its ordinary sense, including, without limitation, any mechanism (e.g. enzymatic or non-enzymatic) by which analyte can be quantified. For example, some embodiments utilize a membrane that contains glucose oxidase that catalyzes the conversion of oxygen and glucose to hydrogen peroxide and gluconate:

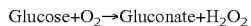

$$Glucose + O_2 \rightarrow Gluconate + H_2O_2$$

Because for each glucose molecule metabolized, there is a proportional change in the co-reactant $O_2$ and the product $H_2O_2$, one can use an electrode to monitor the current change in either the co-reactant or the product to determine glucose concentration.

The term "host," as used herein, is a broad term and is used in its ordinary sense, including, without limitation, mammals, particularly humans.

The term "matched data pairs", as used herein, is a broad term and is used in its ordinary sense, including, without limitation, reference data (e.g., one or more reference analyte data points) matched with substantially time corresponding sensor data (e.g., one or more sensor data points).

The term "Clarke Error Grid", as used herein, is a broad term and is used in its ordinary sense, including, without limitation, an error grid analysis, which evaluates the clinical significance of the difference between a reference glucose value and a sensor generated glucose value, taking into account 1) the value of the reference glucose measurement, 2) the value of the sensor glucose measurement, 3) the relative difference between the two values, and 4) the clinical significance of this difference. See Clarke et al., "Evaluating Clinical Accuracy of Systems for Self-Monitoring of Blood Glucose", Diabetes Care, Volume 10, Number 5, September-October 1987, which is incorporated by reference herein in its entirety.

The term "Consensus Error Grid", as used herein, is a broad term and is used in its ordinary sense, including, without limitation, an error grid analysis that assigns a specific level of clinical risk to any possible error between two time corresponding glucose measurements. The Consensus Error Grid is divided into zones signifying the degree of risk posed by the deviation. See Parkes et al., "A New Consensus Error Grid to Evaluate the Clinical Significance of Inaccuracies in the Measurement of Blood Glucose", Diabetes Care, Volume 23, Number 8, August 2000, which is incorporated by reference herein in its entirety.

The term "clinical acceptability", as used herein, is a broad term and is used in its ordinary sense, including, without limitation, determination of the risk of inaccuracies to a patient. Clinical acceptability considers a deviation between time corresponding glucose measurements (e.g., data from a glucose sensor and data from a reference glucose monitor) and the risk (e.g., to the decision making of a diabetic patient) associated with that deviation based on the glucose value indicated by the sensor and/or reference data. One example of clinical acceptability may be 85% of a given set of measured analyte values within the "A" and "B" region of a standard Clarke Error Grid when the sensor measurements are compared to a standard reference measurement.

The term "R-value," as used herein, is a broad term and is used in its ordinary sense, including, without limitation, one conventional way of summarizing the correlation of data; that is, a statement of what residuals (e.g., root mean square deviations) are to be expected if the data are fitted to a straight line by the a regression.

The term "data association" and "data association function," as used herein, are a broad terms and are used in their ordinary sense, including, without limitation, a statistical analysis of data and particularly its correlation to, or deviation from, from a particular curve. A data association function is used to show data association. For example, the data that forms that calibration set as described herein may be analyzed mathematically to determine its correlation to, or deviation from, a curve (e.g., line or set of lines) that defines the conversion function; this correlation or deviation is the data association. A data association function is used to determine data association. Examples of data association functions include, but are not limited to, linear regression, non-linear mapping/regression, rank (e.g., non-parametric) correlation, least mean square fit, mean absolute deviation (MAD), mean absolute relative difference. In one such example, the correlation coefficient of linear regression is indicative of the amount of data association of the calibration set that forms the conversion function, and thus the quality of the calibration.

The term "quality of calibration" as used herein, is a broad term and is used in its ordinary sense, including, without limitation, the statistical association of matched data pairs in the calibration set used to create the conversion function. For example, an R-value may be calculated for a calibration set to determine its statistical data association, wherein an R-value greater than 0.79 determines a statistically acceptable calibration quality, while an R-value less than 0.79 determines statistically unacceptable calibration quality.

The term "substantially" as used herein, is a broad term and is used in its ordinary sense, including, without limitation, being largely but not necessarily wholly that which is specified.

The term "congruence" as used herein, is a broad term and is used in its ordinary sense, including, without limitation, the quality or state of agreeing, coinciding, or being concordant. In one example, congruence may be determined using rank correlation.

The term "concordant" as used herein, is a broad term and is used in its ordinary sense, including, without limitation, being in agreement or harmony, and/or free from discord.

The phrase "continuous (or continual) analyte sensing," as used herein, is a broad term and is used in its ordinary sense, including, without limitation, the period in which monitoring of analyte concentration is continuously, continually, and or intermittently (but regularly) performed, for example, about every 5 to 10 minutes.

The term "sensor head," as used herein, is a broad term and is used in its ordinary sense, including, without limitation, the region of a monitoring device responsible for the detection of a particular analyte. In one example, a sensor head comprises a non-conductive body, a working electrode (anode), a reference electrode and a counter electrode (cathode) passing through and secured within the body forming an electrochemically reactive surface at one location on the body and an electronic connective means at another location on the body, and a sensing membrane affixed to the body and covering the electrochemically reactive surface. The counter electrode has a greater electrochemically reactive surface area than the working electrode. During general operation of the sensor a biological sample (e.g. blood or interstitial fluid) or a portion thereof contacts (directly or after passage through one or more membranes or domains) an enzyme (e.g., glucose oxidase); the reaction of the biological sample (or portion thereof) results in the formation of reaction products that allow a determination of the analyte (e.g., glucose) level in the biological sample. In some embodiments, the sensing membrane further comprises an enzyme domain (e.g., and enzyme layer), and an electrolyte phase (e.g., a free-flowing liquid phase comprising an electrolyte-containing fluid described further below).

The term "electrochemically reactive surface," as used herein, is a broad term and is used in its ordinary sense, including, without limitation, the surface of an electrode where an electrochemical reaction takes place. In the case of the working electrode, the hydrogen peroxide produced by the enzyme catalyzed reaction of the analyte being detected creates a measurable electronic current (e.g. detection of analyte utilizing analyte oxidase produces $H_2O_2$ peroxide as a by product, $H_2O_2$ reacts with the surface of the working electrode producing two protons ($2H^+$), two electrons ($2e^-$) and one molecule of oxygen ($O_2$) which produces the electronic current being detected). In the case of the counter electrode, a reducible species, e.g., $O_2$ is reduced at the electrode surface in order to balance the current being generated by the working electrode.

The term "electronic connection," as used herein, is a broad term and is used in its ordinary sense, including, without limitation, any electronic connection known to those in the art that may be utilized to interface the sensor head electrodes with the electronic circuitry of a device such as mechanical (e.g., pin and socket) or soldered.

The term "sensing membrane," as used herein, is a broad term and is used in its ordinary sense, including, without limitation, a permeable or semi-permeable membrane that may be comprised of two or more domains and constructed of materials of a few microns thickness or more, which are permeable to oxygen and may or may not be permeable to an analyte of interest. In one example, the sensing membrane comprises an immobilized glucose oxidase enzyme, which enables an electrochemical reaction to occur to measure a concentration of glucose.

The term "biointerface membrane," as used herein, is a broad term and is used in its ordinary sense, including, without limitation, a permeable membrane that may be comprised of two or more domains and constructed of materials of a few microns thickness or more, which may be placed over the sensor body to keep host cells (e.g., macrophages) from gaining proximity to, and thereby damaging, the sensing membrane or forming a barrier cell layer and interfering with the transport of analyte across the tissue-device interface.

In the disclosure which follows, the following abbreviations apply: Eq and Eqs (equivalents); mEq (milliequivalents); M (molar); mM (millimolar) μM (micromolar); N (Normal); mol (moles); mmol (millimoles); μmol (micromoles); nmol (nanomoles); g (grams); mg (milligrams); μg (micrograms); Kg (kilograms); L (liters); mL (milliliters); dL (deciliters); μL (microliters); cm (centimeters); mm (millimeters); μm (micrometers); nm (nanometers); h and hr (hours); min. (minutes); s and sec. (seconds); ° C. (degrees Centigrade).

Overview

The preferred embodiments relate to the use of an analyte sensor that measures a concentration of analyte of interest or a substance indicative of the concentration or presence of the analyte. In some embodiments, the sensor is a continuous device, for example a subcutaneous, transdermal, or intravascular device. In some embodiments, the device may analyze a plurality of intermittent blood samples. The analyte sensor may use any method of analyte-sensing, including enzymatic, chemical, physical, electrochemical, spectrophotometric, polarimetric, calorimetric, radiometric, or the like.

The analyte sensor uses any known method, including invasive, minimally invasive, and non-invasive sensing techniques, to provide an output signal indicative of the concentration of the analyte of interest. The output signal is typically a raw signal that is used to provide a useful value of the analyte of interest to a user, such as a patient or physician, who may be using the device. Accordingly, appropriate smoothing, calibration, and evaluation methods may be applied to the raw signal and/or system as a whole to provide relevant and acceptable estimated analyte data to the user.

Sensor

The analyte sensor useful with the preferred embodiments may be any device capable of measuring the concentration of an analyte of interest. One exemplary embodiment is described below, which utilizes an implantable glucose sensor. However, it should be understood that the devices and methods described herein may be applied to any device capable of detecting a concentration of analyte of and providing an output signal that represents the concentration of the analyte.

FIG. 1 is an exploded perspective view of a glucose sensor in one embodiment. The implantable glucose sensor 10 utilizes amperometric electrochemical sensor technology to measure glucose. In this exemplary embodiment, a body 12 and a head 14 house electrodes 16 and sensor electronics, which are described in more detail with reference to FIG. 2. Three electrodes 16 are operably connected to the sensor electronics (FIG. 2) and are covered by a sensing membrane 17 and a biointerface membrane 18, which are attached by a clip 19. In alternative embodiments, the number of electrodes may be less than or greater than three.

The three electrodes 16, which protrude through the head 14, including a platinum working electrode, a platinum counter electrode, and a silver/silver chloride reference electrode. The top ends of the electrodes are in contact with an electrolyte phase (not shown), which is a free-flowing fluid phase disposed between the sensing membrane and the electrodes. The sensing membrane 17 includes an enzyme, e.g., glucose oxidase, which covers the electrolyte phase. In turn, the biointerface membrane 18 covers the sensing membrane 17 and serves, at least in part, to protect the sensor from external forces that may result in environmental stress cracking of the sensing membrane 17.

In the illustrated embodiment, the counter electrode is provided to balance the current generated by the species being measured at the working electrode. In the case of a glucose oxidase based glucose sensor, the species being measured at the working electrode is $H_2O_2$. Glucose oxidase catalyzes the conversion of oxygen and glucose to hydrogen peroxide and gluconate according to the following reaction:

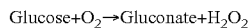

The change in $H_2O_2$ can be monitored to determine glucose concentration because for each glucose molecule metabolized, there is a proportional change in the product $H_2O_2$. Oxidation of $H_2O_2$ by the working electrode is balanced by reduction of ambient oxygen, enzyme generated $H_2O_2$, or other reducible species at the counter electrode. The $H_2O_2$ produced from the glucose oxidase reaction further reacts at the surface of working electrode and produces two protons ($2H^+$), two electrons ($2e^-$), and one oxygen molecule ($O_2$) (See, e.g., Fraser, D. M. "An Introduction to In vivo Biosensing: Progress and problems." In "Biosensors and the Body," D. M. Fraser, ed., 1997, pp. 1-56 John Wiley and Sons, New York.)

Figure 2:
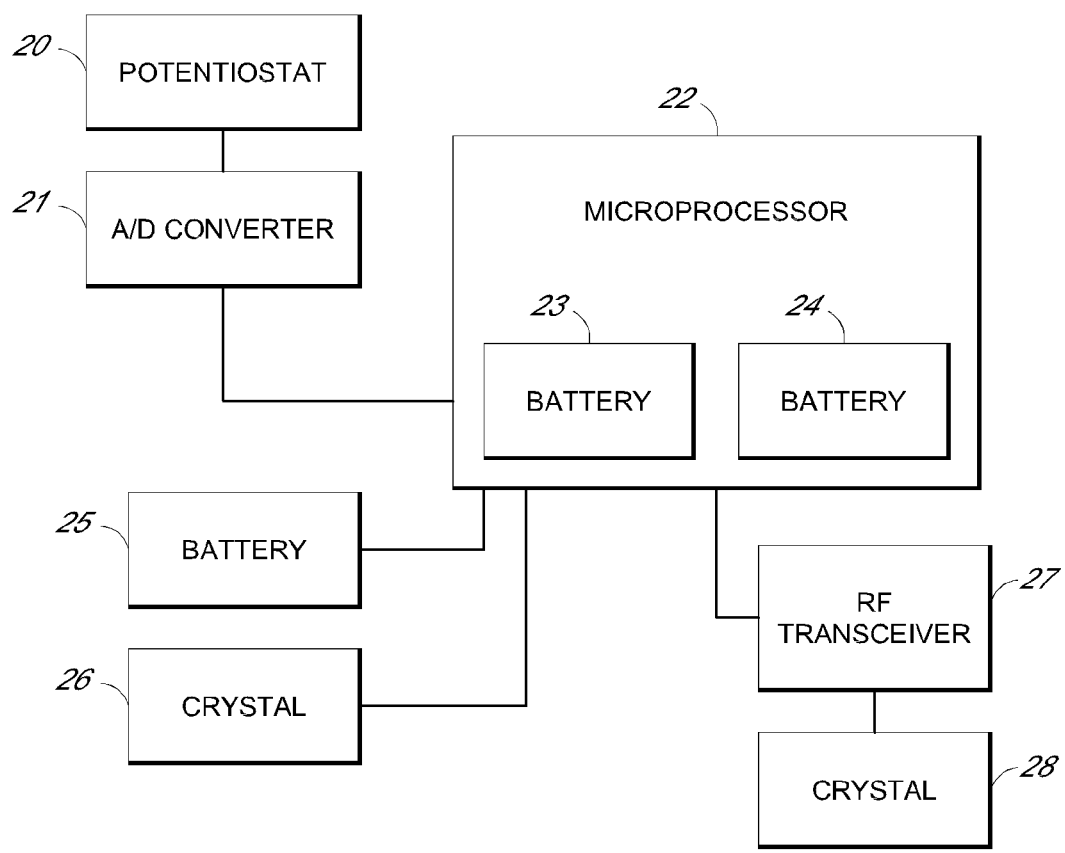
FIG. 2 is a block diagram that illustrates the sensor electronics in one embodiment.

In one embodiment, a potentiostat is used to measure the electrochemical reaction(s) at the electrode(s) (see FIG. 2).

The potentiostat applies a constant potential between the working and reference electrodes to produce a current value. The current that is produced at the working electrode (and flows through the circuitry to the counter electrode) is proportional to the diffusional flux of $H_2O_2$. Accordingly, a raw signal may be produced that is representative of the concentration of glucose in the users body, and therefore may be utilized to estimate a meaningful glucose value, such as described elsewhere herein.

One problem of enzymatic glucose sensors such as described above is the non-glucose reaction rate-limiting phenomenon. For example, if oxygen is deficient, relative to the amount of glucose, then the enzymatic reaction will be limited by oxygen rather than glucose. Consequently, the output signal will be indicative of the oxygen concentration rather than the glucose concentration.

FIG. 2 is a block diagram that illustrates the sensor electronics in one embodiment. In this embodiment, the potentiostat 20 is shown, which is operatively connected to electrodes 16 (FIG. 1) to obtain a current value, and includes a resistor (not shown) that translates the current into voltage. An A/D converter 21 digitizes the analog signal into counts for processing. Accordingly, the resulting raw data signal in counts is directly related to the current measured by the potentiostat 20.

A microprocessor 22 is the central control unit that houses EEPROM 23 and SRAM 24, and controls the processing of the sensor electronics. It may be noted that alternative embodiments utilize a computer system other than a microprocessor to process data as described herein. In some alternative embodiments, an application-specific integrated circuit (ASIC) may be used for some or all the sensor's central processing. The EEPROM 23 provides semi-permanent storage of data, storing data such as sensor ID and necessary programming to process data signals (e.g., programming for data smoothing such as described below). The SRAM 24 is used for the system's cache memory, for example for temporarily storing recent sensor data.

A battery 25 is operatively connected to the microprocessor 22 and provides the necessary power for the sensor. In one embodiment, the battery is a Lithium Manganese Dioxide battery, however any appropriately sized and powered battery may be used (e.g., AAA, Nickel-cadmium, Zinc-carbon, Alkaline, Lithium, Nickel-metal hydride, Lithium-ion, Zinc-air, Zinc-mercury oxide, Silver-zinc, or hermetically-sealed). In some embodiments, a plurality of batteries may be used to power the system. A Quartz Crystal 26 is operatively connected to the microprocessor 22 and maintains system time for the computer system as a whole.

Figure 4A:
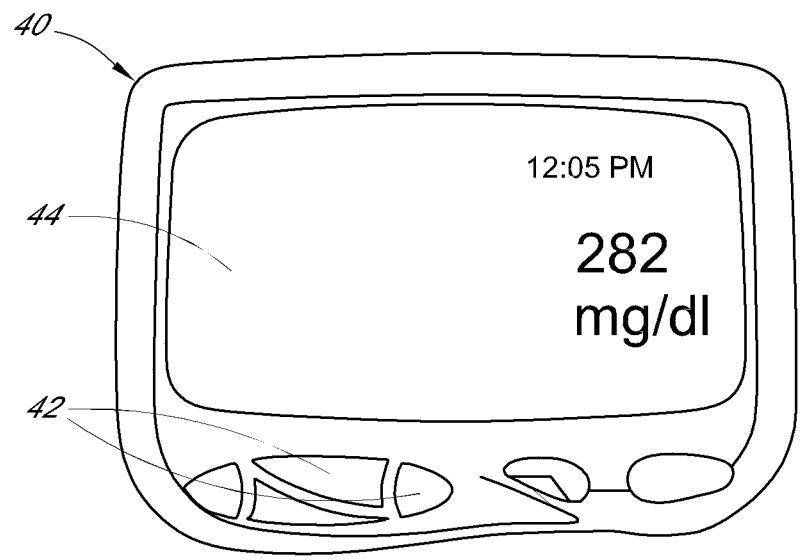
FIGS. 4A to 4D are schematic views of a receiver in first, second, third, and fourth embodiments, respectively.
Figure 4B:
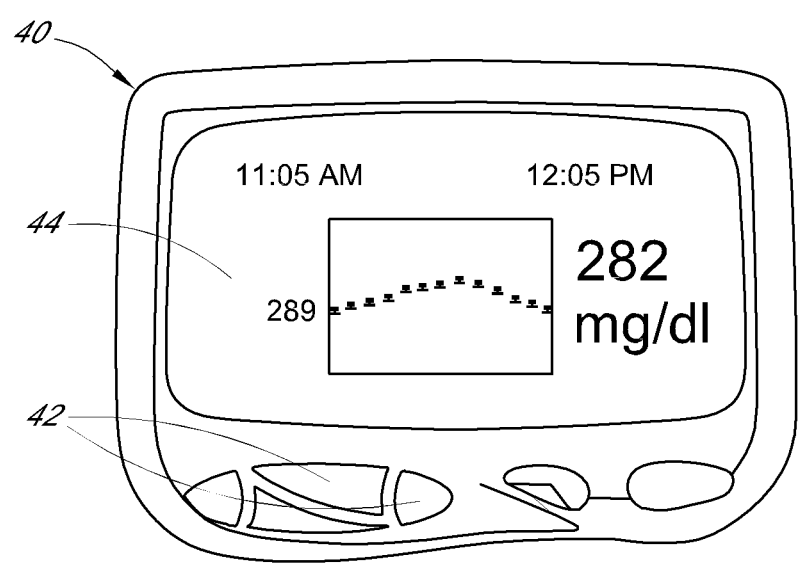
Figure 4C:
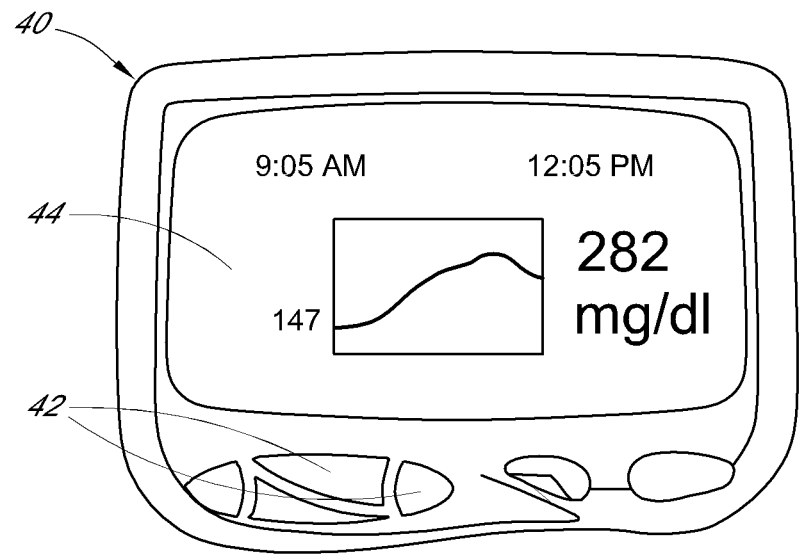
Figure 4D:
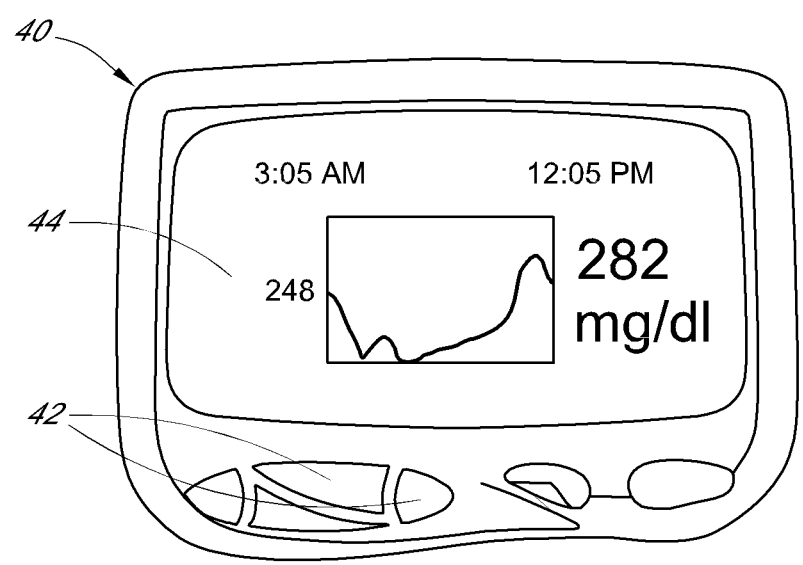
Figure 5:
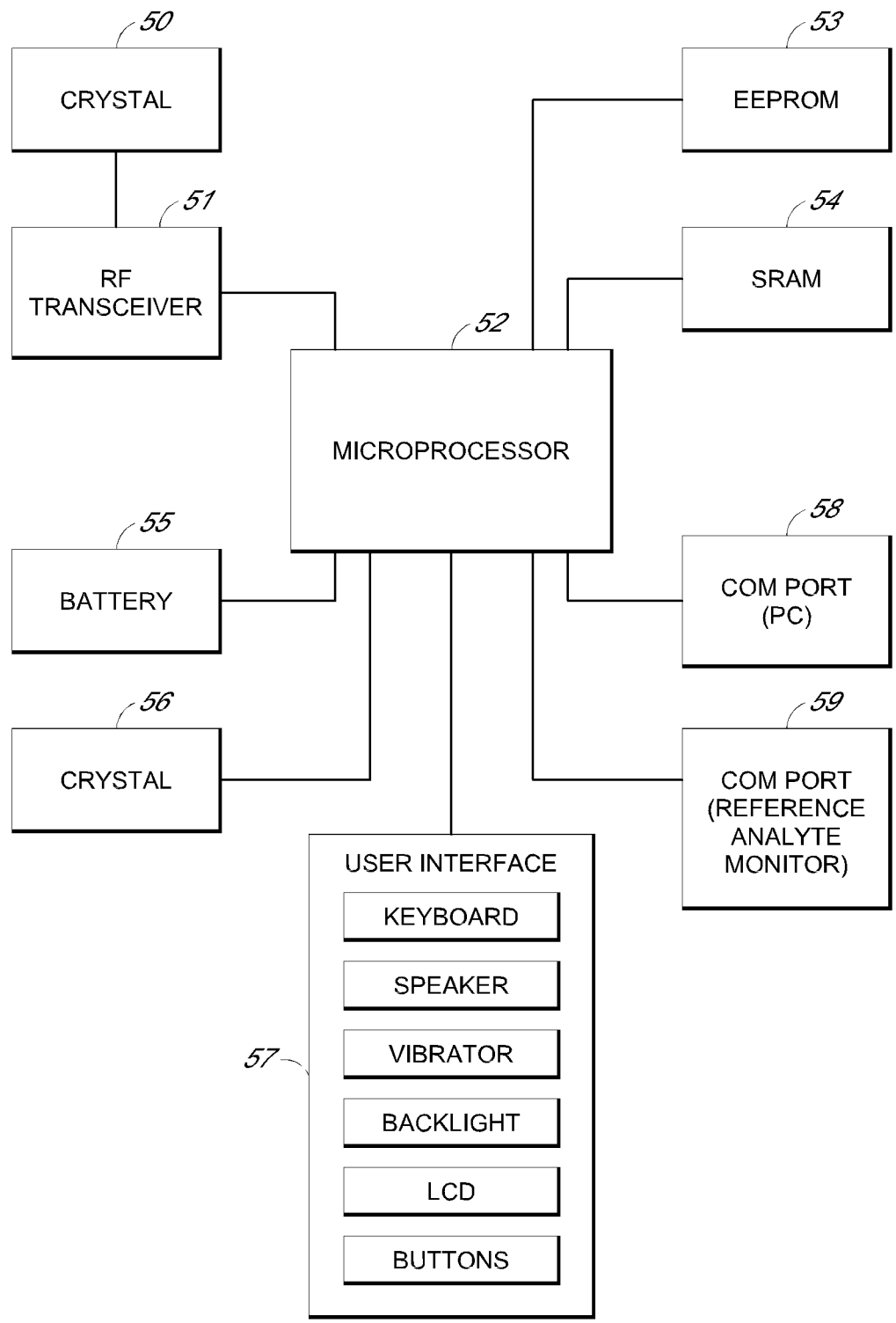
FIG. 5 is a block diagram of the receiver electronics in one embodiment.

An RF Transceiver 27 is operably connected to the microprocessor 22 and transmits the sensor data from the sensor to a receiver (see FIGS. 4 and 5). Although an RF transceiver is shown here, other embodiments include a wired rather than wireless connection to the receiver. In yet other embodiments, the receiver is transcutaneously powered via an inductive coupling, for example. A quartz crystal 28 provides the system time for synchronizing the data transmissions from the RF transceiver. It may be noted that the transceiver 27 may be substituted for a transmitter in one embodiment.

Data Smoothing

Typically, an analyte sensor produces a raw data signal that is indicative of the analyte concentration of a user, such as described in more detail with reference to FIGS. 1 and 2, above. However, it is well known that the above described glucose sensor is only one example of an abundance of analyte sensors that are able to provide a raw data signal output indicative of the concentration of the analyte of interest. Thus, it should be understood that the devices and methods of the preferred embodiments, including data smoothing, calibration, evaluation, and other data processing, may be applied to raw data obtained from any analyte sensor capable of producing a output signal.

It has been found that raw data signals received from an analyte sensor include signal noise, which degrades the quality of the data. Thus, it has been known to use smoothing algorithms help improve the signal-to-noise ratio in the sensor by reducing signal jitter, for example. One example of a conventional data smoothing algorithms include finite impulse response filter (FIR), which is particularly suited for reducing high-frequency noise (see Steil et al. U.S. Pat. No. 6,558,351). Other analyte sensors have utilized heuristic and moving average type algorithms to accomplish data smoothing of signal jitter in data signals, for example.

It is advantageous to also reduce signal noise by attenuating transient, low frequency, non-analyte related signal fluctuations (e.g., transient ischemia and/or long transient periods of postural effects that interfere with sensor function due to lack of oxygen and/or other physiological effects).

In one embodiment, this attenuation of transient low frequency non-analyte related signal noise is accomplished using a recursive filter. In contrast to conventional non-recursive (e.g., FIR) filters in which each computation uses new input data sets, a recursive filter is an equation that uses moving averages as inputs; that is, a recursive filter includes previous averages as part of the next filtered output. Recursive filters are advantageous at least in part due to their computational efficiency.

Figure 3:
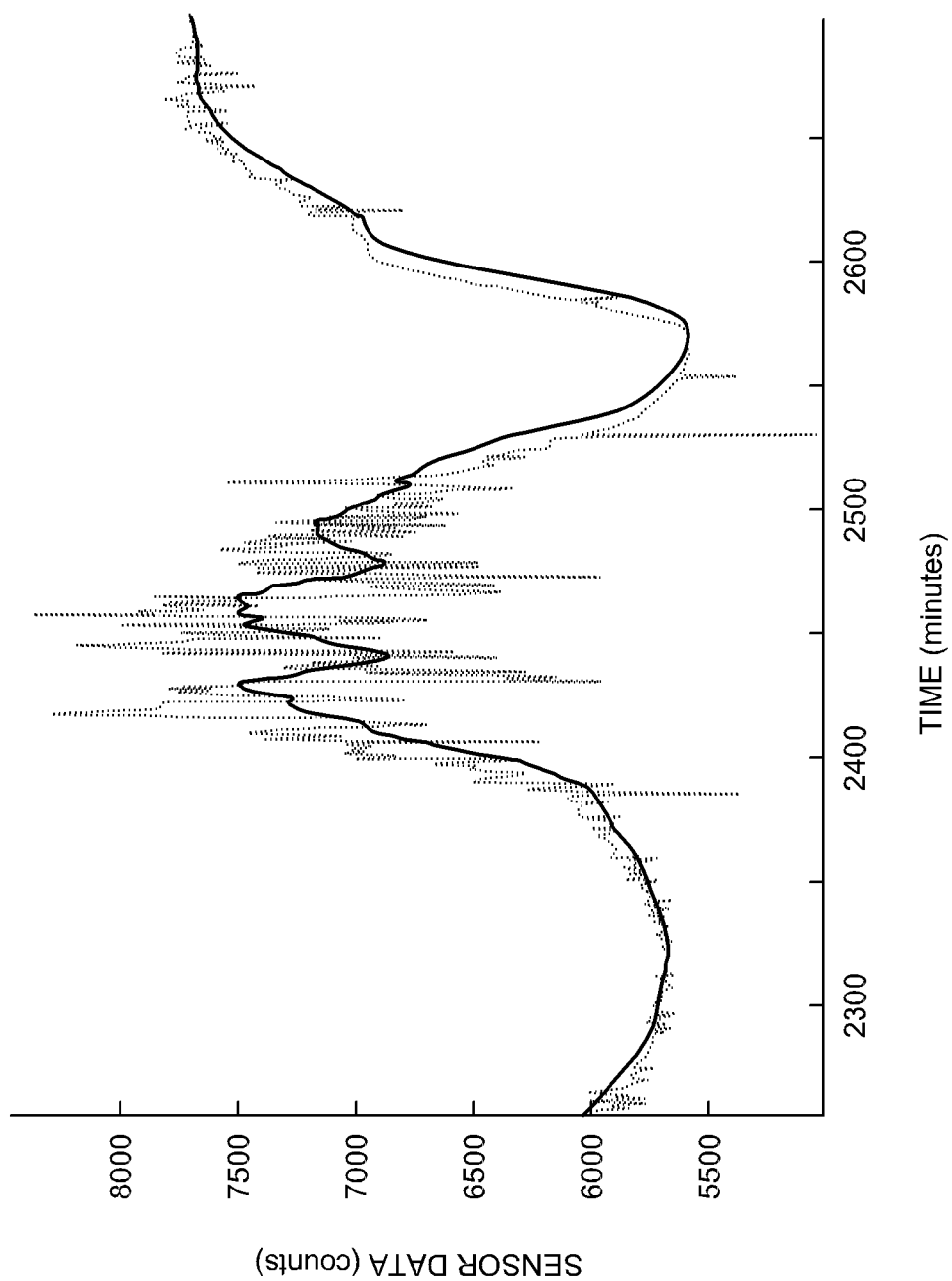
FIG. 3 is a graph that illustrates data smoothing of a raw data signal in one embodiment.

FIG. 3 is a graph that illustrates data smoothing of a raw data signal in one embodiment. In this embodiment, the recursive filter is implemented as a digital infinite impulse response filter (IIR) filter, wherein the output is computed using 6 additions and 7 multiplies as shown in the following equation:

$$y(n) = \frac{a_0 * x(n) + a_1 * x(n-1) + a_2 * x(n-2) + a_3 * x(n-3) - b_1 * y(n-1) - b_2 * y(n-2) - b_3 * y(n-3)}{b_0}$$

This polynomial equation includes coefficients that are dependent on sample rate and frequency behavior of the filter. In this exemplary embodiment, frequency behavior passes low frequencies up to cycle lengths of 40 minutes, and is based on a 30 second sample rate.

In some embodiments, data smoothing may be implemented in the sensor and the smoothed data transmitted to a receiver for additional processing. In other embodiments, raw data may be sent from the sensor to a receiver for data smoothing and additional processing therein. In yet other embodiments, the sensor is integral with the receiver and therefore no transmission of data is required.

In one exemplary embodiment, wherein the sensor is an implantable glucose sensor, data smoothing is performed in the sensor to ensure a continuous stream of data. In alternative embodiments, data smoothing may be transmitted from the sensor to the receiver, and the data smoothing performed at the receiver; it may be noted however that there may be a risk of transmit-loss in the radio transmission from the sensor to the receiver when the transmission is wireless. For example, in embodiments wherein a sensor is implemented in vivo, the raw sensor signal may be more consistent within the sensor (in vivo) than the raw signal transmitted to a source (e.g., receiver) outside the body (e.g., if a patient were to take the receiver off to shower, communication between the sensor and receiver may be lost and data smoothing in the receiver would halt accordingly.) Consequently, it may be noted that a multiple point data loss in the filter may take, for example, anywhere from 25 to 40 minutes for the smoothed data to recover to where it would have been had there been no data loss.

Receiver

FIGS. 4A to 4D are schematic views of a receiver in first, second, third, and fourth embodiments, respectively. A receiver 40 comprises systems necessary to receive, process, and display sensor data from an analyte sensor, such as described elsewhere herein. Particularly, the receiver 40 may be a pager-sized device, for example, and comprise a user interface that has a plurality of buttons 42 and a liquid crystal display (LCD) screen 44, and which may include a backlight. In some embodiments the user interface may also include a keyboard, a speaker, and a vibrator such as described with reference to FIG. 5.

FIG. 4A illustrates a first embodiment wherein the receiver shows a numeric representation of the estimated analyte value on its user interface, which is described in more detail elsewhere herein.

FIG. 4B illustrates a second embodiment wherein the receiver shows an estimated glucose value and one hour of historical trend data on its user interface, which is described in more detail elsewhere herein.

FIG. 4C illustrates a third embodiment wherein the receiver shows an estimated glucose value and three hours of historical trend data on its user interface, which is described in more detail elsewhere herein.

FIG. 4D illustrates a fourth embodiment wherein the receiver shows an estimated glucose value and nine hours of historical trend data on its user interface, which is described in more detail elsewhere herein.

In some embodiments a user is able to toggle through some or all of the screens shown in FIGS. 4A to 4D using a toggle button on the receiver. In some embodiments, the user is able to interactively select the type of output displayed on their user interface. In some embodiments, the sensor output may have alternative configurations, such as is described with reference to FIG. 6, block 69, for example.

FIG. 5 is a block diagram of the receiver electronics in one embodiment. It may be noted that the receiver may comprise a configuration such as described with reference to FIGS. 4A to 4D, above. Alternatively, the receiver may comprise any configuration, including a desktop computer, laptop computer, a personal digital assistant (PDA), a server (local or remote to the receiver), or the like. In some embodiments, a receiver may be adapted to connect (via wired or wireless connection) to a desktop computer, laptop computer, a PDA, a server (local or remote to the receiver), or the like in order to download data from the receiver. In some alternative embodiments, the receiver is housed within or directly connected to the sensor in a manner that allows sensor and receiver electronics to work directly together and/or share data processing resources. Accordingly, the receiver, including its electronics, may be generally described as a "computer system."

A quartz crystal 50 is operatively connected to an RF transceiver 51 that together function to receive and synchronize data signals (e.g., raw data signals transmitted from the RF transceiver). Once received, the microprocessor 52 processes the signals, such as described below.

The microprocessor 52 is the central control unit that provides the necessary processing, such as calibration algorithms stored within an EEPROM 53. The EEPROM 53 is operatively connected to the microprocessor 52 and provides semi-permanent storage of data, storing data such as receiver ID and necessary programming to process data signals (e.g., programming for performing calibration and other algorithms described elsewhere herein). In some embodiments, an application-specific integrated circuit (ASIC) may be used for some or all the receiver's central processing. An SRAM 54 is used for the system's cache memory and is helpful in data processing.

The microprocessor 52, which is operatively connected to EEPROM 53 and SRAM 54, controls the processing of the receiver electronics including, but not limited to, a sensor data receiving module, a reference data receiving module, a data matching module, a calibration set module, a conversion function module, a sensor data transformation module, a quality evaluation module, a interface control module, and a stability determination module, which are described in more detail below. It may be noted that any of the above processing may be programmed into and performed in the sensor electronics (FIG. 2) in place of, or in complement with, the receiver electronics (FIG. 5).

A battery 55 is operatively connected to the microprocessor 52 and provides the necessary power for the receiver. In one embodiment, the battery is a AAA battery, however any appropriately sized and powered battery may be used. In some embodiments, a plurality of batteries may be used to power the system. A quartz crystal 56 is operatively connected to the microprocessor 52 and maintains system time for the computer system as a whole.

A user interface 57 comprises a keyboard, speaker, vibrator, backlight, LCD, and a plurality of buttons. The components that comprise the user interface 57 provide the necessary controls to interact with the user. A keyboard may allow, for example, input of user information about himself/herself, such as mealtime, exercise, insulin administration, and reference analyte values. A speaker may provide, for example, audible signals or alerts for conditions such as present and/or predicted hyper- and hypoglycemic conditions. A vibrator may provide, for example, tactile signals or alerts for reasons such as described with reference to the speaker, above. A backlight may be provided, for example, to aid the user in reading the LCD in low light conditions. An LCD may be provided, for example, to provide the user with visual data output such as described in more detail with reference to FIGS. 4A to 4D and FIG. 6. Buttons may provide toggle, menu selection, option selection, mode selection, and reset, for example.

Communication ports, including a personal computer (PC) corn port 58 and a reference analyte monitor corn port 59 may be provided to enable communication with systems that are separate from, or integral with, the receiver. The PC corn port 58 comprises means for communicating with another computer system (e.g., PC, PDA, server, or the like). In one exemplary embodiment, the receiver is able to download historic data to a physician's PC for retrospective analysis by the physician. The reference analyte monitor corn port 59 comprises means for communicating with a reference analyte monitor so that reference analyte values may be automatically downloaded into the receiver. In one embodiment, the reference analyte monitor is integral with the receiver, and the reference analyte corn port 59 allows internal communication between the two integral systems. In another embodiment, the reference analyte monitor corn port 59 allows a wireless or wired connection to the reference analyte monitor such as a self-monitoring blood glucose monitor (e.g., for measuring finger stick blood samples).

Algorithms

Figure 6:
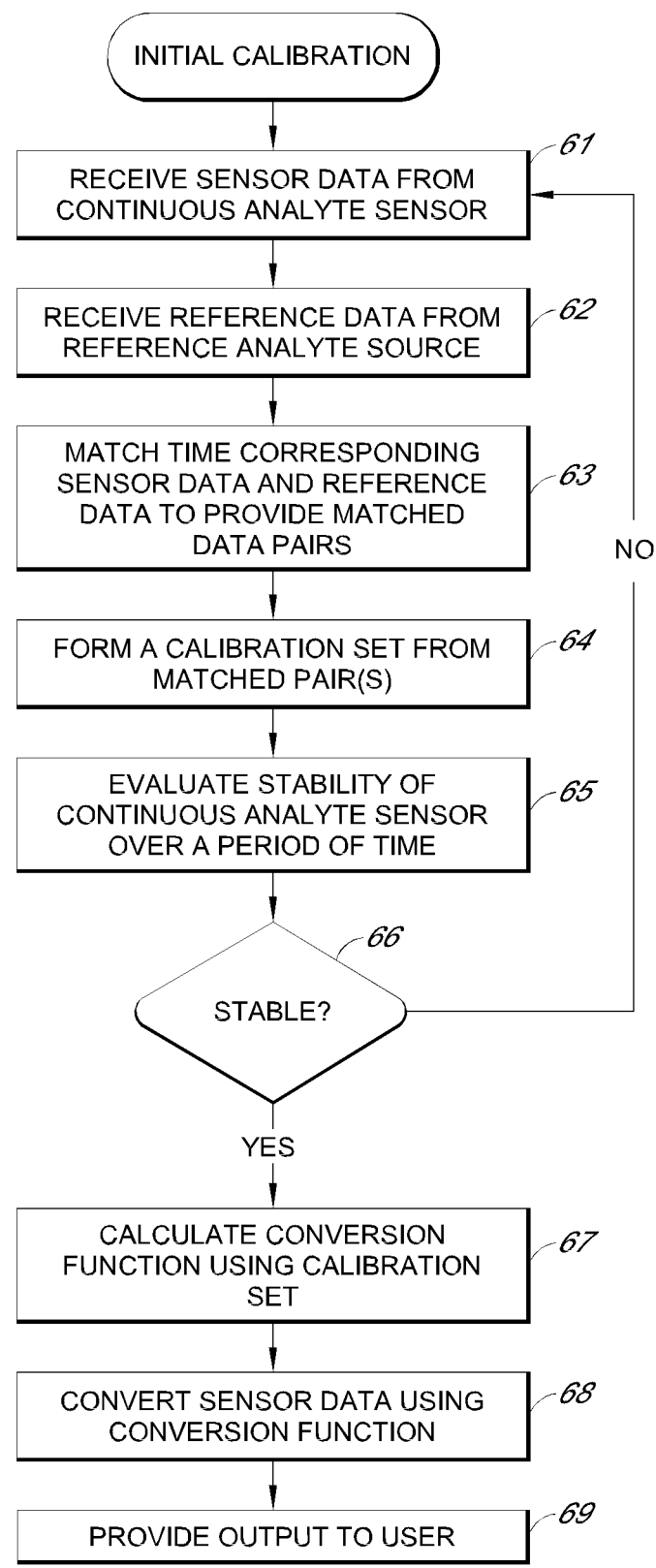
FIG. 6 is a flow chart that illustrates the initial calibration and data output of the sensor data in one embodiment.

Reference is now made to FIG. 6, which is a flow chart that illustrates the initial calibration and data output of the sensor data in one embodiment.

Calibration of an analyte sensor comprises data processing that converts sensor data signal into an estimated analyte measurement that is meaningful to a user. Accordingly, a reference analyte value is used to calibrate the data signal from the analyte sensor.

At block 61, a sensor data receiving module, also referred to as the sensor data module, receives sensor data (e.g., a data stream), including one or more time-spaced sensor data points, from a sensor via the receiver, which may be in wired or wireless communication with the sensor. The sensor data point(s) may be smoothed, such as described with reference to FIG. 3, above. It may be noted that during the initialization of the sensor, prior to initial calibration, the receiver (e.g., computer system) receives and stores the sensor data, however may not display any data to the user until initial calibration and possibly stabilization of the sensor has been determined.

At block 62, a reference data receiving module, also referred to as the reference input module, receives reference data from a reference analyte monitor, including one or more reference data points. In one embodiment, the reference analyte points may comprise results from a self-monitored blood analyte test (e.g., from a finger stick test). In one such embodiment, the user may administer a self-monitored blood analyte test to obtain an analyte value (e.g., point) using any known analyte sensor, and then enter the numeric analyte value into the computer system. In another such embodiment, a self-monitored blood analyte test comprises a wired or wireless connection to the receiver (e.g. computer system) so that the user simply initiates a connection between the two devices, and the reference analyte data is passed or downloaded between the self-monitored blood analyte test and the receiver. In yet another such embodiment, the self-monitored analyte test is integral with the receiver so that the user simply provides a blood sample to the receiver, and the receiver runs the analyte test to determine a reference analyte value.

It may be noted that certain acceptability parameters may be set for reference values received from the user. For example, in one embodiment, the receiver may only accept reference analyte values between about 40 and about 400 mg/dL. Other examples of determining valid reference analyte values are described in more detail with reference to FIG. 8.

At block 63, a data matching module, also referred to as the processor module, matches reference data (e.g., one or more reference analyte data points) with substantially time corresponding sensor data (e.g., one or more sensor data points) to provide one or more matched data pairs. In one embodiment, one reference data point is matched to one time corresponding sensor data point to form a matched data pair. In another embodiment, a plurality of reference data points are averaged (e.g., equally or non-equally weighted average, mean-value, median, or the like) and matched to one time corresponding sensor data point to form a matched data pair. In another embodiment, one reference data point is matched to a plurality of time corresponding sensor data points averaged to form a matched data pair. In yet another embodiment, a plurality of reference data points are averaged and matched to a plurality of time corresponding sensor data points averaged to form a matched data pair.

In one embodiment, a time corresponding sensor data comprises one or more sensor data points that occur 15±5 min after the reference analyte data timestamp (e.g., the time that the reference analyte data is obtained). In this embodiment, the 15 minute time delay has been chosen to account for an approximately 10 minute delay introduced by the filter used in data smoothing and an approximately 5 minute physiological time-lag (e.g., the time necessary for the analyte to diffusion through a membrane(s) of an analyte sensor). In alternative embodiments, the time corresponding sensor value may be more or less than the above-described embodiment, for example ±60 minutes. Variability in time correspondence of sensor and reference data may be attributed to, for example a longer or shorter time delay introduced by the data smoothing filter, or if the configuration of the analyte sensor incurs a greater or lesser physiological time lag.

It may be noted that in some practical implementations of the sensor, the reference analyte data may be obtained at a time that is different from the time that the data is input into the receiver. Accordingly, it should be noted that the "time stamp" of the reference analyte (e.g., the time at which the reference analyte value was obtained) is not the same as the time at which the reference analyte data was obtained by receiver. Therefore, some embodiments include a time stamp requirement that ensures that the receiver stores the accurate time stamp for each reference analyte value, that is, the time at which the reference value was actually obtained from the user.

In some embodiments, tests are used to evaluate the best matched pair using a reference data point against individual sensor values over a predetermined time period (e.g., about 30 minutes). In one such exemplary embodiment, the reference data point is matched with sensor data points at 5-minute intervals and each matched pair is evaluated. The matched pair with the best correlation may be selected as the matched pair for data processing. In some alternative embodiments, matching a reference data point with an average of a plurality of sensor data points over a predetermined time period may be used to form a matched pair.

At block 64, a calibration set module, also referred to as the processor module, forms an initial calibration set from a set of one or more matched data pairs, which are used to determine the relationship between the reference analyte data and the sensor analyte data, such as will be described in more detail with reference to block 67, below.

The matched data pairs, which make up the initial calibration set, may be selected according to predetermined criteria. It may be noted that the criteria for the initial calibration set may be the same as, or different from, the criteria for the update calibration set, which is described in more detail with reference to FIG. 10. In some embodiments, the number (n) of data pair(s) selected for the initial calibration set is one. In other embodiments, n data pairs are selected for the initial calibration set wherein n is a function of the frequency of the received reference data points. In one exemplary embodiment, six data pairs make up the initial calibration set.

In some embodiments, the data pairs are selected only within a certain analyte value threshold, for example wherein the reference analyte value is between about 40 and about 400 mg/dL. In some embodiments, the data pairs that form the initial calibration set are selected according to their time stamp. In some embodiments, the calibration set is selected such as described with reference to FIG. 10

At block 65, a stability determination module, also referred to as the start-up module, determines the stability of the analyte sensor over a period of time. It may be noted that some analyte sensors may have an initial instability time period during which the analyte sensor is unstable for environmental, physiological, or other reasons. One example of initial sensor instability is an embodiment wherein the analyte sensor is implanted subcutaneously; in this example embodiment, stabilization of the analyte sensor may be dependent upon the maturity of the tissue ingrowth around and within the sensor. Another example of initial sensor instability is in an embodiment wherein the analyte sensor is implemented transdermally; in this example embodiment, stabilization of the analyte sensor may be dependent upon electrode stabilization and/or sweat, for example.

Accordingly, in some embodiments, determination of sensor stability may include waiting a predetermined time period (e.g., an implantable sensor is known to require a time period for tissue, and a transdermal sensor is known to require time to equilibrate the sensor with the user's skin); in some embodiments, this predetermined waiting period is between about one minute and about six weeks. In some embodiments, the sensitivity (e.g., sensor signal strength with respect to analyte concentration) may be used to determine the stability of the sensor; for example, amplitude and/or variability of sensor sensitivity may be evaluated to determine the stability of the sensor. In alternative embodiments, detection of pH levels, oxygen, hypochlorite, interfering species (e.g., ascorbate, urea, and acetaminophen), correlation between sensor and reference values (e.g., R-value), baseline drift and/or offset, and the like may be used to determine the stability of the sensor. In one exemplary embodiment, wherein the sensor is a glucose sensor, it is known to provide a signal that is associated with interfering species (e.g., ascorbate, urea, acetaminophen), which may be used to evaluate sensor stability. In another exemplary embodiment, wherein the sensor is a glucose sensor such as described with reference to FIGS. 1 and 2, the counter electrode can be monitored for oxygen deprivation, which may be used to evaluate sensor stability or functionality.

At decision block 66, the system (e.g., microprocessor) determines whether the analyte sensor is sufficiently stable according to certain criteria, such as described above. In one embodiment wherein the sensor is an implantable glucose sensor, the system waits a predetermined time period believed necessary for sufficient tissue ingrowth and evaluates the sensor sensitivity (e.g., between about one minute and six weeks). In another embodiment, the receiver determines sufficient stability based on oxygen concentration near the sensor head. In yet another embodiment, the sensor determines sufficient stability based on a reassessment of baseline drift and/or offset. In yet another alternative embodiment, the system evaluates stability by monitoring the frequency content of the sensor data stream over a predetermined amount of time (e.g., 24 hours); in this alternative embodiment, a template (or templates) are provided that reflect acceptable levels of glucose physiology and are compared with the actual sensor data, wherein a predetermined amount of agreement between the template and the actual sensor data is indicative of sensor stability. It may be noted that a few examples of determining sufficient stability are given here, however a variety of known tests and parameters may be used to determine sensor stability without departing from the spirit and scope of the preferred embodiments.

If the receiver does not assess that the stability of the sensor is sufficient, then the processing returns to block 61, wherein the receiver receives sensor data such as described in more detail above. The above-described steps are repeated until sufficient stability is determined.

If the receiver does assess that the stability of the sensor is sufficient, then processing continues to block 67 and the calibration set is used to calibrate the sensor.

At block 67, the conversion function module uses the calibration set to create a conversion function. The conversion function substantially defines the relationship between the reference analyte data and the analyte sensor data.

A variety of known methods may be used with the preferred embodiments to create the conversion function from the calibration set. In one embodiment, wherein a plurality of matched data points form the initial calibration set, a linear least squares regression is performed on the initial calibration set such as described with reference to FIG. 7.

Figure 7:
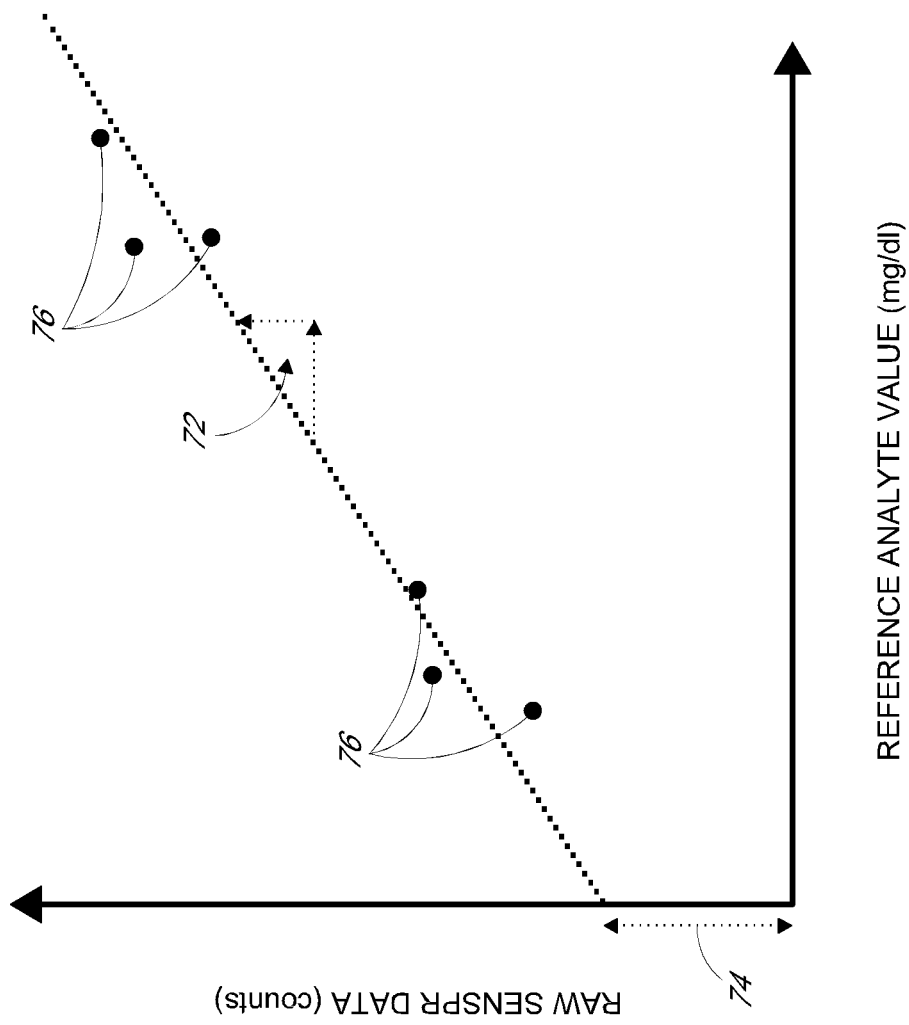
FIG. 7 is a graph that illustrates a regression performed on a calibration set to obtain a conversion function in one exemplary embodiment.

FIG. 7 is a graph that illustrates a regression performed on a calibration set to create a conversion function in one exemplary embodiment. In this embodiment, a linear least squares regression is performed on the initial calibration set. The x-axis represents reference analyte data; the y-axis represents sensor data. The graph pictorially illustrates regression of the matched pairs 76 in the calibration set. Regression calculates a slope 72 and an offset 74 (y=mx+b), which defines the conversion function.

In alternative embodiments other algorithms could be used to determine the conversion function, for example forms of linear and non-linear regression, for example fuzzy logic, neural networks, piece-wise linear regression, polynomial fit, genetic algorithms, and other pattern recognition and signal estimation techniques.

In yet other alternative embodiments, the conversion function may comprise two or more different optimal conversions because an optimal conversion at any time is dependent on one or more parameters, such as time of day, calories consumed, exercise, or analyte concentration above or below a set threshold, for example. In one such exemplary embodiment, the conversion function is adapted for the estimated glucose concentration (e.g., high vs. low). For example in an implantable glucose sensor it has been observed that the cells surrounding the implant will consume at least a small amount of glucose as it diffuses toward the glucose sensor. Assuming the cells consume substantially the same amount of glucose whether the glucose concentration is low or high, this phenomenon will have a greater effect on the concentration of glucose during low blood sugar episodes than the effect on the concentration of glucose during relatively higher blood sugar episodes. Accordingly, the conversion function is adapted to compensate for the sensitivity differences in blood sugar level. In one implementation, the conversion function comprises two different regression lines wherein a first regression line is applied when the estimated blood glucose concentration is at or below a certain threshold (e.g., 150 mg/dL) and a second regression line is applied when the estimated blood glucose concentration is at or above a certain threshold (e.g., 150 mg/dL). In one alternative implementation, a predetermined pivot of the regression line that forms the conversion function may be applied when the estimated blood is above or below a set threshold (e.g., 150 mg/dL), wherein the pivot and threshold are determined from a retrospective analysis of the performance of a conversion function and its performance at a range of glucose concentrations. In another implementation, the regression line that forms the conversion function is pivoted about a point in order to comply with clinical acceptability standards (e.g., Clarke Error Grid, Consensus Grid, mean absolute relative difference, or other clinical cost function). Although only a few example implementations are described, the preferred embodiments contemplate numerous implementations wherein the conversion function is adaptively applied based on one or more parameters that may affect the sensitivity of the sensor data over time.

Referring again to FIG. 6, at block 68, a sensor data transformation module uses the conversion function to transform sensor data into substantially real-time analyte value estimates, also referred to as calibrated data, as sensor data is continuously (or intermittently) received from the sensor. For example, in the embodiment of FIG. 7, the sensor data, which may be provided to the receiver in "counts", is translated in to estimate analyte value(s) in mg/dL. In other words, the offset value at any given point in time may be subtracted from the raw value (e.g., in counts) and divided by the slope to obtain the estimate analyte value:

$$mg/dL = \frac{(rawvalue - \text{offset})}{\text{slope}}$$

In some alternative embodiments, the sensor and/or reference analyte values are stored in a database for retrospective analysis.

At block 69, an output module provides output to the user via the user interface. The output is representative of the estimated analyte value, which is determined by converting the sensor data into a meaningful analyte value such as described in more detail with reference to block 68, above. User output may be in the form of a numeric estimated analyte value, an indication of directional trend of analyte concentration, and/or a graphical representation of the estimated analyte data over a period of time, for example. Other representations of the estimated analyte values are also possible, for example audio and tactile.

In one exemplary embodiment, such as shown in FIG. 4A, the estimated analyte value is represented by a numeric value. In other exemplary embodiments, such as shown in FIGS. 4B to 4D, the user interface graphically represents the estimated analyte data trend over predetermined a time period (e.g., one, three, and nine hours, respectively). In alternative embodiments, other time periods may be represented.

In some embodiments, the user interface begins displaying data to the user after the sensor's stability has been affirmed. In some alternative embodiments however, the user interface displays data that is somewhat unstable (e.g., does not have sufficient stability at block 66); in these embodiments, the receiver may also include an indication of instability of the sensor data (e.g., flashing, faded, or another indication of sensor instability displayed on the user interface). In some embodiments, the user interface informs the user of the status of the stability of the sensor data.

Accordingly, after initial calibration of the sensor, and possibly determination of stability of the sensor data, real-time continuous analyte information may be displayed on the user interface so that the user may regularly and proactively care for his/her diabetic condition within the bounds set by his/her physician.

In alternative embodiments, the conversion function is used to predict analyte values at future points in time. These predicted values may be used to alert the user of upcoming hypoglycemic or hyperglycemic events. Additionally, predicted values may be used to compensate for the time lag (e.g., 15 minute time lag such as described elsewhere herein), so that an estimate analyte value displayed to the user represents the instant time, rather than a time delayed estimated value.

In some embodiments, the substantially real time estimated analyte value, a predicted future estimate analyte value, a rate of change, and/or a directional trend of the analyte concentration is used to control the administration of a constituent to the user, including an appropriate amount and time, in order to control an aspect of the user's biological system. One such example is a closed loop glucose sensor and insulin pump, wherein the analyte data (e.g., estimated glucose value, rate of change, and/or directional trend) from the glucose sensor is used to determine the amount of insulin, and time of administration, that may be given to a diabetic user to evade hyper- and hypoglycemic conditions.

Figure 8:
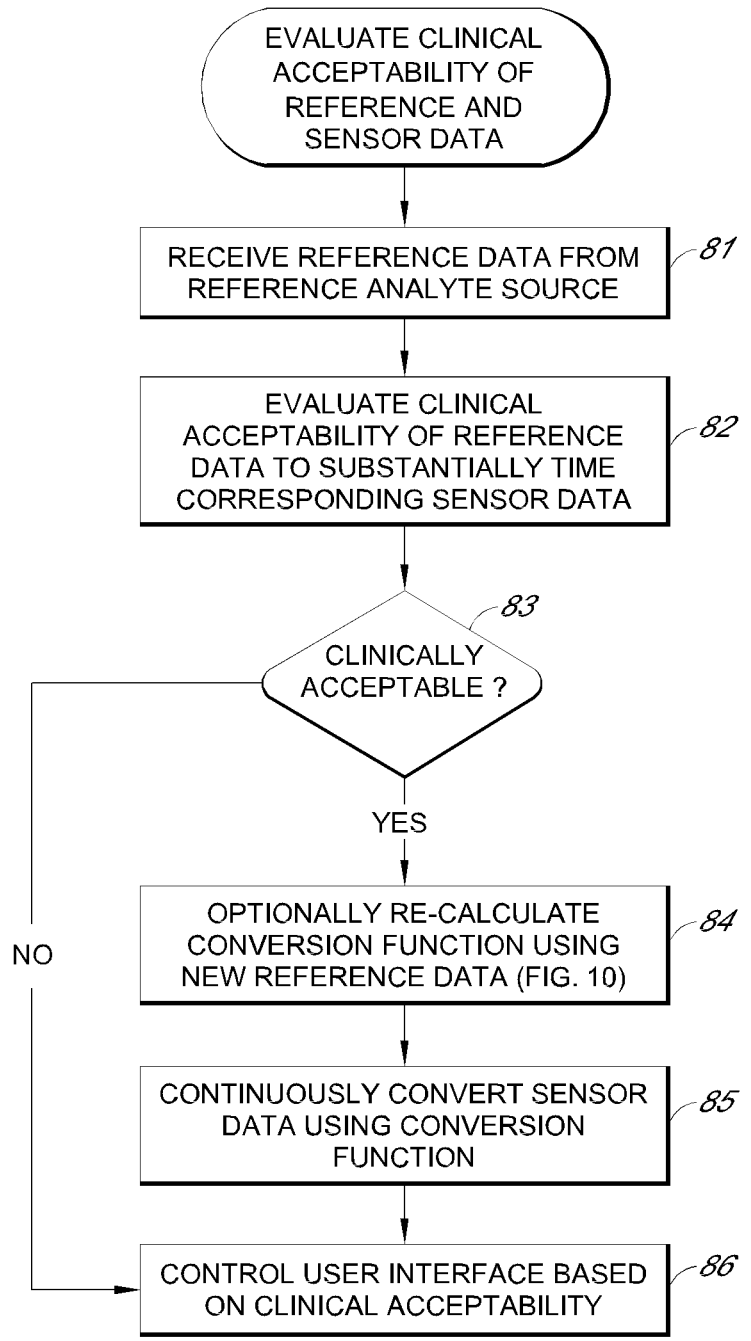
FIG. 8 is a flow chart that illustrates the process of evaluating the clinical acceptability of reference and sensor data in one embodiment.

Reference is now made to FIG. 8, which is a flow chart that illustrates the process of evaluating the clinical acceptability of reference and sensor data in one embodiment. Although some clinical acceptability tests are disclosed here, any known clinical standards and methodologies may be applied to evaluate the clinical acceptability of reference and analyte data herein.

It may be noted that the conventional analyte meters (e.g., self-monitored blood analyte tests) are known to have a +−20% error in analyte values. For example, gross errors in analyte readings are known to occur due to patient error in self-administration of the blood analyte test. In one such example, if the user has traces of sugar on his/her finger while obtaining a blood sample for a glucose concentration test, then the measured glucose value will likely be much higher than the actual glucose value in the blood. Additionally, it is known that self-monitored analyte tests (e.g., test strips) are occasionally subject to manufacturing error.

Another cause for error includes infrequency and time delay that may occur if a user does not self-test regularly, or if a user self-tests regularly but does not enter the reference value at the appropriate time or with the appropriate time stamp. Therefore, it may be advantageous to validate the acceptability of reference analyte values prior to accepting them as valid entries. Accordingly, the receiver evaluates the clinical acceptability of received reference analyte data prior to their acceptance as a valid reference value.

In one embodiment, the reference analyte data (and/or sensor analyte data) is evaluated with respect to substantially time corresponding sensor data (and/or substantially time corresponding reference analyte data) to determine the clinical acceptability of the reference analyte and/or sensor analyte data. Clinical acceptability considers a deviation between time corresponding glucose measurements (e.g., data from a glucose sensor and data from a reference glucose monitor) and the risk (e.g., to the decision making of a diabetic patient) associated with that deviation based on the glucose value indicated by the sensor and/or reference data. Evaluating the clinical acceptability of reference and sensor analyte data, and controlling the user interface dependent thereon, may minimize clinical risk.

In one embodiment, the receiver evaluates clinical acceptability each time reference data is obtained. In another embodiment, the receiver evaluates clinical acceptability after the initial calibration and stabilization of the sensor, such as described with reference to FIG. 6, above. In some embodiments, the receiver evaluates clinical acceptability as an initial pre-screen of reference analyte data, for example after determining if the reference glucose measurement is between about 40 and 400 mg/dL. In other embodiments, other methods of pre-screening data may be used, for example by determining if a reference analyte data value is physiologically feasible based on previous reference analyte data values (e.g., below a maximum rate of change).

After initial calibration such as described in more detail with reference to FIG. 6, the sensor data receiving module 61 receives substantially continuous sensor data (e.g., a data stream) via a receiver and converts that data into estimated analyte values. As used herein, "substantially continuous" is broad enough to include a data stream of individual measurements taken at time intervals (e.g., time-spaced) ranging from fractions of a second up to, e.g., 1, 2, or 5 minutes. As sensor data is continuously converted, it may be occasionally recalibrated such as described in more detail with reference FIG. 10. Initial calibration and re-calibration of the sensor requires a reference analyte value. Accordingly, the receiver may receive reference analyte data at any time for appropriate processing. These reference analyte values may be evaluated for clinical acceptability such as described below as a fail-safe against reference analyte test errors.

At block 81, the reference data receiving module, also referred to as the reference input module, receives reference analyte data from a reference analyte monitor. In one embodiment, the reference data comprises one analyte value obtained from a reference monitor. In some alternative embodiments however, the reference data includes a set of analyte values entered by a user into the interface and averaged by known methods such as described elsewhere herein.

In some embodiments, the reference data is pre-screened according to environmental and physiological issues, such as time of day, oxygen concentration, postural effects, and patient-entered environmental data. In one example embodiment, wherein the sensor comprises an implantable glucose sensor, an oxygen sensor within the glucose sensor is used to determine if sufficient oxygen is being provided to successfully complete the necessary enzyme and electrochemical reactions for glucose sensing. In another example embodiment wherein the sensor comprises an implantable glucose sensor, the counter electrode could be monitored for a "rail-effect", that is, when insufficient oxygen is provided at the counter electrode causing the counter electrode to reach operational (e.g., circuitry) limits. In yet another example embodiment, the patient is prompted to enter data into the user interface, such as meal times and/or amount of exercise, which could be used to determine likelihood of acceptable reference data.

It may be further noted that evaluation data, such as described in the paragraph above, may be used to evaluate an optimum time for reference analyte measurement. Correspondingly, the user interface may then prompt the user to provide a reference data point for calibration within a given time period. Consequently, because the receiver proactively prompts the user during optimum calibration times, the likelihood of error due to environmental and physiological limitations may decrease and consistency and acceptability of the calibration may increase.

At block 82, the clinical acceptability evaluation module, also referred to as clinical module, evaluates the clinical acceptability of newly received reference data and/or time corresponding sensor data. In some embodiments of evaluating clinical acceptability, the rate of change of the reference data as compared to previous data is assessed for clinical acceptability. That is, the rate of change and acceleration (or deceleration) of many analytes has certain physiological limits within the body. Accordingly, a limit may be set to determine if the new matched pair is within a physiologically feasible range, indicated by a rate of change from the previous data that is within known physiological and/or statistical limits. Similarly, in some embodiments any algorithm that predicts a future value of an analyte may be used to predict and then compare an actual value to a time corresponding predicted value to determine if the actual value falls within a clinically acceptable range based on the predictive algorithm, for example.

In one exemplary embodiment, the clinical acceptability evaluation module 82 matches the reference data with a substantially time corresponding converted sensor value such as described with reference to FIG. 6 above, and plots the matched data on a Clarke Error Grid such as described in more detail with reference to FIG. 9.

Figure 9:
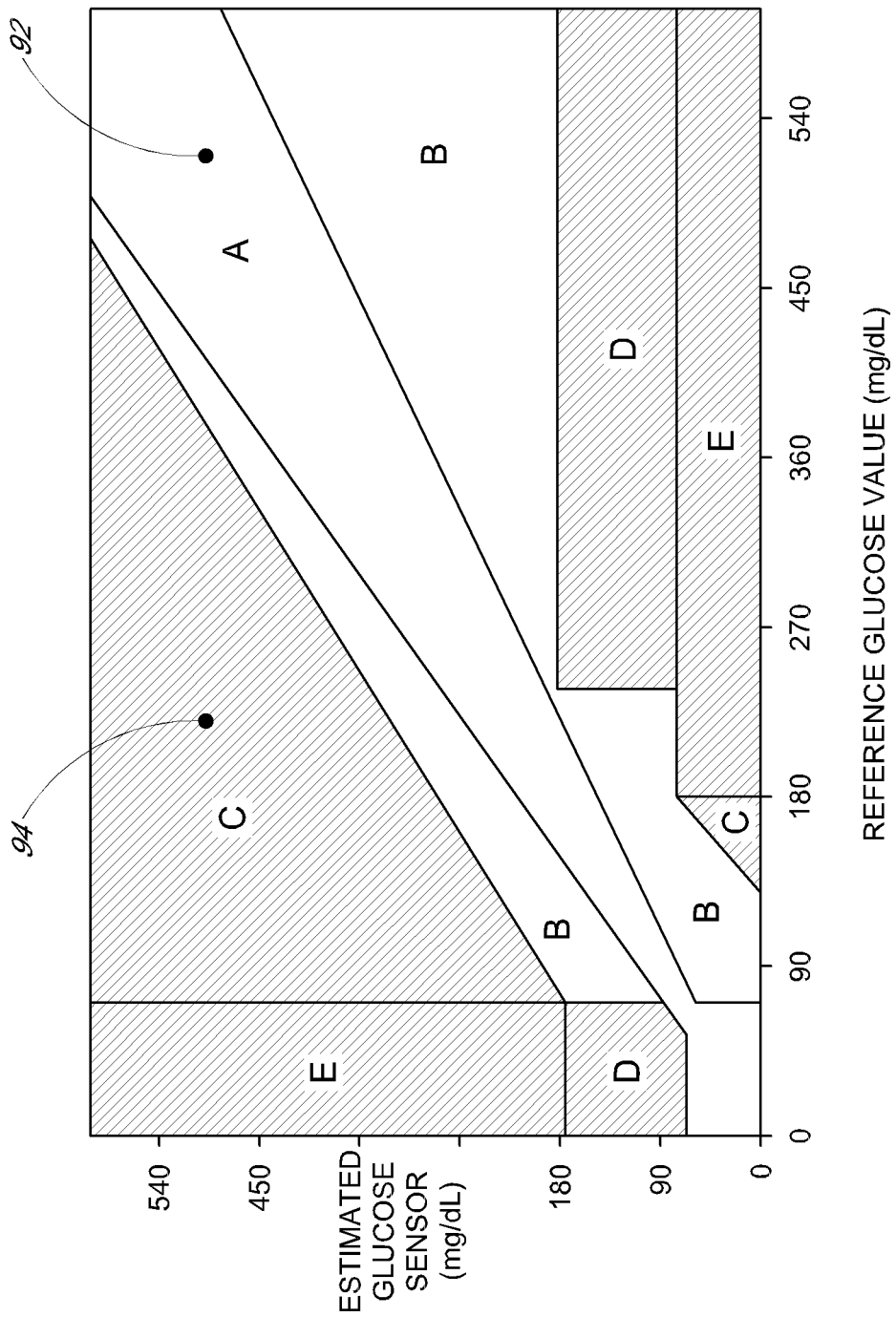
FIG. 9 is a graph of two data pairs on a Clarke Error Grid to illustrate the evaluation of clinical acceptability in one exemplary embodiment.

FIG. 9 is a graph of two data pairs on a Clarke Error Grid to illustrate the evaluation of clinical acceptability in one exemplary embodiment. The Clarke Error Grid may be used by the clinical acceptability evaluation module to evaluate the clinical acceptability of the disparity between a reference glucose value and a sensor glucose (e.g., estimated glucose) value, if any, in an embodiment wherein the sensor is a glucose sensor. The x-axis represents glucose reference glucose data and the y-axis represents estimated glucose sensor data. Matched data pairs are plotted accordingly to their reference and sensor values, respectively. In this embodiment, matched pairs that fall within the A and B regions of the Clarke Error Grid are considered clinically acceptable, while matched pairs that fall within the C, D, and E regions of the Clarke Error Grid are not considered clinically acceptable. Particularly, FIG. 9 shows a first matched pair 92 is shown which falls within the A region of the Clarke Error Grid, therefore is it considered clinically acceptable. A second matched pair 94 is shown which falls within the C region of the Clarke Error Grid, therefore it is not considered clinically acceptable.

It may be noted that a variety of other known methods of evaluation of clinical acceptability may be utilized. In one alternative embodiment, the Consensus Grid is used to evaluate the clinical acceptability of reference and sensor data. In another alternative embodiment, a mean absolute difference calculation may be used to evaluate the clinical acceptability of the reference data. In another alternative embodiment, the clinical acceptability may be evaluated using any relevant clinical acceptability test, such as a known grid (e.g., Clarke Error or Consensus), and including additional parameters such as time of day and/or the increase or decreasing trend of the analyte concentration. In another alternative embodiment, a rate of change calculation may be used to evaluate clinical acceptability. In yet another alternative embodiment, wherein the received reference data is in substantially real time, the conversion function could be used to predict an estimated glucose value at a time corresponding to the time stamp of the reference analyte value (this may be required due to a time lag of the sensor data such as described elsewhere herein). Accordingly, a threshold may be set for the predicted estimated glucose value and the reference analyte value disparity, if any.

Referring again to FIG. 8, the results of the clinical acceptability evaluation are assessed. If clinical acceptability is determined with the received reference data, then processing continues to block 84 to optionally recalculate the conversion function using the received reference data in the calibration set. If, however, clinical acceptability is not determined, then the processing progresses to block 86 to control the user interface, such as will be described with reference to block 86 below.

At block 84, the conversion function module optionally recreates the conversion function using the received reference data. In one embodiment, the conversion function module adds the newly received reference data (e.g., including the matched sensor data) into the calibration set, displaces the oldest, and/or least concordant matched data pair from the calibration set, and recalculates the conversion function accordingly. In another embodiment, the conversion function module evaluates the calibration set for best calibration based on inclusion criteria, such as described in more detail with reference to FIG. 10.

At 85, the sensor data transformation module uses the conversion function to continually (or intermittently) convert sensor data into estimated analyte values, also referred to as calibrated data, such as described in more detail with reference to FIG. 6, block 68.

At block 86, the interface control module, also referred to as the fail-safe module, controls the user interface based upon the clinical acceptability of the reference data received. If the evaluation (block 82) deems clinical acceptability, then the user interface may function as normal; that is, providing output for the user such as described in more detail with reference to FIG. 6, block 69.

If however the reference data is not considered clinically acceptable, then the fail-safe module begins the initial stages of fail-safe mode. In some embodiments, the initial stages of fail-safe mode include altering the user interface so that estimated sensor data is not displayed to the user. In some embodiments, the initial stages of fail-safe mode include prompting the user to repeat the reference analyte test and provide another reference analyte value. The repeated analyte value is then evaluated for clinical acceptability such as described with reference to blocks 81 to 83, above.

If the results of the repeated analyte test are determined to be clinically unacceptable, then fail-safe module may alter the user interface to reflect full fail-safe mode. In one embodiment, full fail-safe mode includes discontinuing sensor analyte display output on the user interface. In other embodiments, color-coded information, trend information, directional information (e.g., arrows or angled lines), gauges, and/or fail-safe information may be displayed, for example.

If the results of the repeated analyte test are determined to be clinically acceptable, then the first analyte value is discarded, and the repeated analyte value is accepted. The process returns to block 84 to optionally recalculate the conversion function, such as described in more detail with reference to block 84, above.

Figure 10:
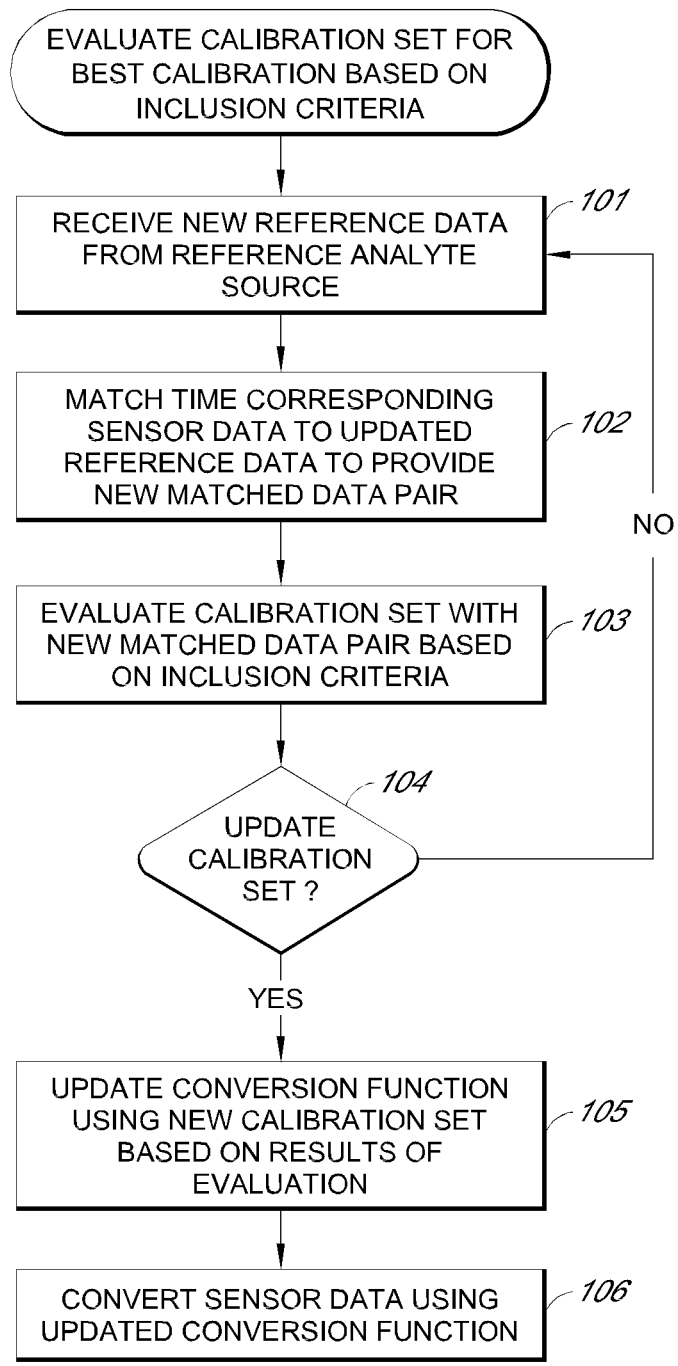
FIG. 10 is a flow chart that illustrates the process of evaluation of calibration data for best calibration based on inclusion criteria of matched data pairs in one embodiment.

Reference is now made to FIG. 10, which is a flow chart that illustrates the process of evaluation of calibration data for best calibration based on inclusion criteria of matched data pairs in one embodiment.

It may be noted that calibration of analyte sensors may be variable over time; that is, the conversion function suitable for one point in time may not be suitable for another point in time (e.g., hours, days, weeks, or months later). For example, in an embodiment wherein the analyte sensor is subcutaneously implantable, the maturation of tissue ingrowth over time may cause variability in the calibration of the analyte sensor. As another example, physiological changes in the user (e.g., metabolism, interfering blood constituents, lifestyle changes) may cause variability in the calibration of the sensor. Accordingly, a continuously updating calibration algorithm is disclosed that includes reforming the calibration set, and thus recalculating the conversion function, over time according to a set of inclusion criteria.

At block 101, the reference data receiving module, also referred to as the reference input module, receives a new reference analyte value (e.g., data point) from the reference analyte monitor. In some embodiments, the reference analyte value may be pre-screened according to criteria such as described in more detail with reference to FIG. 6, block 62. In some embodiments, the reference analyte value may be evaluated for clinical acceptability such as described in more detail with reference to FIG. 8.

At block 102, the data matching module, also referred to as the processor module, forms one or more updated matched data pairs by matching new reference data to substantially time corresponding sensor data, such as described in more detail with reference to FIG. 6, block 63.

At block 103, a calibration evaluation module evaluates the new matched pair(s) inclusion into the calibration set. In some embodiments, the receiver simply adds the updated matched data pair into the calibration set, displaces the oldest and/or least concordant matched pair from the calibration set, and proceeds to recalculate the conversion function accordingly (block 105).

In some embodiments, the calibration evaluation includes evaluating only the new matched data pair. In some embodiments, the calibration evaluation includes evaluating all of the matched data pairs in the existing calibration set and including the new matched data pair; in such embodiments not only is the new matched data pair evaluated for inclusion (or exclusion), but additionally each of the data pairs in the calibration set are individually evaluated for inclusion (or exclusion). In some alternative embodiments, the calibration evaluation includes evaluating all possible combinations of matched data pairs from the existing calibration set and including the new matched data pair to determine which combination best meets the inclusion criteria. In some additional alternative embodiments, the calibration evaluation includes a combination of at least two of the above-described embodiments.

Inclusion criteria comprise one or more criteria that define a set of matched data pairs that form a substantially optimal calibration set. One inclusion criterion comprises ensuring the time stamp of the matched data pairs (that make up the calibration set) span at least a set time period (e.g., three hours). Another inclusion criterion comprises ensuring that the time stamps of the matched data pairs are not more than a set age (e.g., one week old). Another inclusion criterion ensures that the matched pairs of the calibration set have a substantially distributed amount of high and low raw sensor data, estimated sensor analyte values, and/or reference analyte values. Another criterion comprises ensuring all raw sensor data, estimated sensor analyte values, and/or reference analyte values are within a predetermined range (e.g., 40 to 400 mg/dL for glucose values). Another criterion comprises evaluating the rate of change of the analyte concentration (e.g., from sensor data) during the time stamp of the matched pair(s). For example, sensor and reference data obtained during the time when the analyte concentration is undergoing a slow rate of change may be less susceptible inaccuracies caused by time lag and other physiological and non-physiological effects. Another criterion comprises evaluating the congruence of respective sensor and reference data in each matched data pair; the matched pairs with the most congruence may be chosen. Another criterion comprises evaluating physiological changes (e.g., low oxygen due to a user's posture that may effect the function of a subcutaneously implantable analyte sensor, or other effects such as described with reference to FIG. 6) to ascertain a likelihood of error in the sensor value. It may be noted that evaluation of calibration set criteria may comprise evaluating one, some, or all of the above described inclusion criteria. It is contemplated that additional embodiments may comprise additional inclusion criteria not explicitly described herein.

At block 104, the evaluation of the calibration set determines whether to maintain the previously established calibration set, or if the calibration set should be updated (e.g., modified) with the new matched data pair. In some embodiments, the oldest matched data pair is simply displaced when a new matched data pair is included. It may be noted however that a new calibration set may include not only the determination to include the new matched data pair, but in some embodiments, may also determine which of the previously matched data pairs should be displaced from the calibration set.

At block 105, the conversion function module recreates the conversion function using the modified calibration set. The calculation of the conversion function is described in more detail with reference to FIG. 6.

At block 106, the sensor data transformation module converts sensor data to calibrated data using the updated conversion function. Conversion of raw sensor data into estimated analyte values is described in more detail with reference to FIG. 6.

Figure 11:
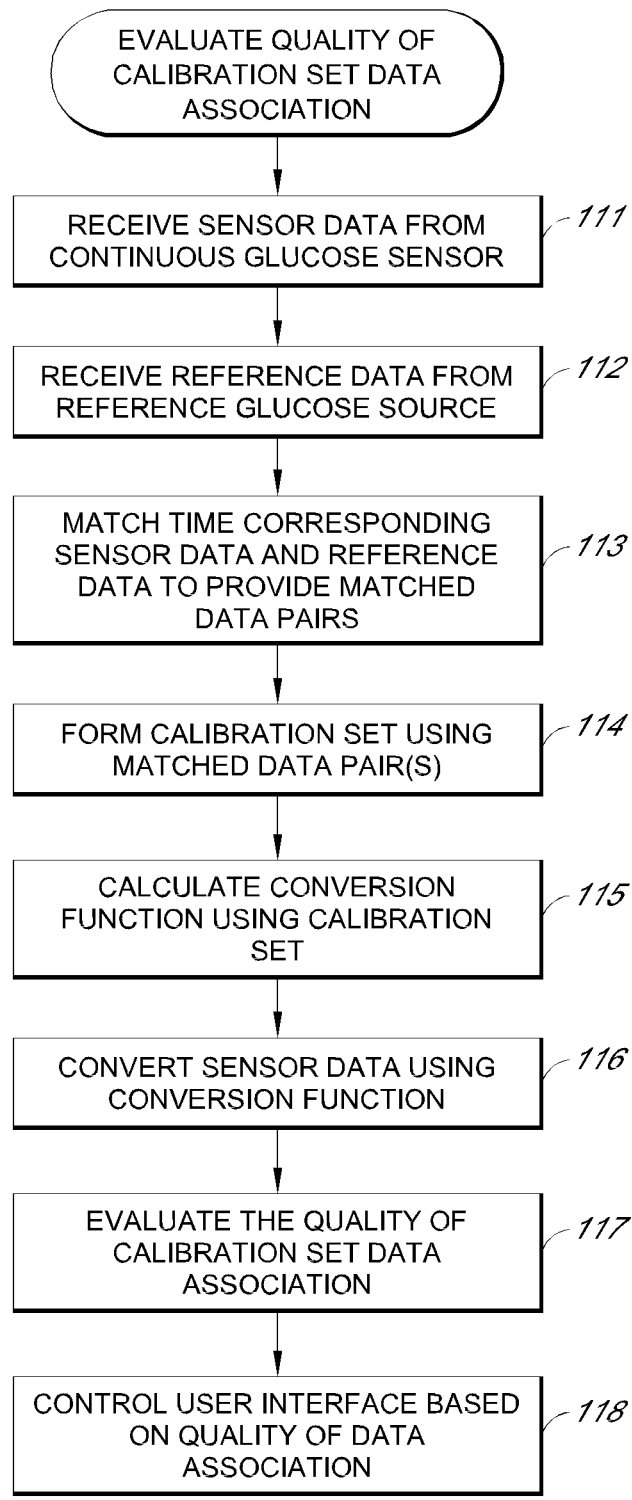
FIG. 11 is a flow chart that illustrates the process of evaluating the quality of the calibration in one embodiment.

Reference is now made to FIG. 11, which is a flow chart that illustrates the process of evaluating the quality of the calibration in one embodiment. The calibration quality may be evaluated by determining the statistical association of data that forms the calibration set, which determines the confidence associated with the conversion function used in calibration and conversion of raw sensor data into estimated analyte values.

In one embodiment calibration quality may be evaluated after initial or updated calculation of the conversion function such as described elsewhere herein. However it may be noted that calibration quality may be performed at any time during the data processing.

At block 111, a sensor data receiving module, also referred to as the sensor data module, receives the sensor data from the sensor such as described in more detail with reference to FIG. 6.

At block 112, a reference data receiving module, also referred to as the reference input module, receives reference data from a reference analyte monitor, such as described in more detail with reference to FIG. 6.

At block 113, the data matching module, also referred to as the processor module, matches received reference data with substantially time corresponding sensor data to provide one or more matched data pairs, such as described in more detail with reference to FIG. 6.

At block 114, the calibration set module, also referred to as the processor module, forms a calibration set from one or more matched data pairs such as described in more detail with reference to FIGS. 6, 8, and 10.

At block 115, the conversion function module calculates a conversion function using the calibration set, such as described in more detail with reference to FIGS. 6, 8, and 10.

At block 116, the sensor data transformation module continuously (or intermittently) converts received sensor data into estimated analyte values, also referred to as calibrated data, such as described in more detail with reference to FIGS. 6, 8, and 10.

At block 117, a quality evaluation module evaluates the quality of the calibration. In one embodiment, the quality of the calibration is based on the association of the calibration set data using statistical analysis. Statistical analysis may comprise any known cost function such as linear regression, non-linear mapping/regression, rank (e.g., non-parametric) correlation, least mean square fit, mean absolute deviation (MAD), mean absolute relative difference, and the like. The result of the statistical analysis provides a measure of the association of data used in calibrating the system. A threshold of data association may be set to determine if sufficient quality is exhibited in a calibration set.

In another embodiment, the quality of the calibration is determined by evaluating the calibration set for clinical acceptability, such as described with reference to blocks 82 and 83 (e.g., Clarke Error Grid, Consensus Grid, or clinical acceptability test). As an example, the matched data pairs that form the calibration set may be plotted on a Clarke Error Grid, such that when all matched data pairs fall within the A and B regions of the Clarke Error Grid, then the calibration is determined to be clinically acceptable.

In yet another alternative embodiment, the quality of the calibration is determined based initially on the association of the calibration set data using statistical analysis, and then by evaluating the calibration set for clinical acceptability. If the calibration set fails the statistical and/or the clinical test, the processing returns to block 115 to recalculate the conversion function with a new (e.g., optimized) set of matched data pairs. In this embodiment, the processing loop (block 115 to block 117) iterates until the quality evaluation module 1) determines clinical acceptability, 2) determines sufficient statistical data association, 3) determines both clinical acceptability and sufficient statistical data association, or 4) surpasses a threshold of iterations; after which the processing continues to block 118.

Figure 12A:
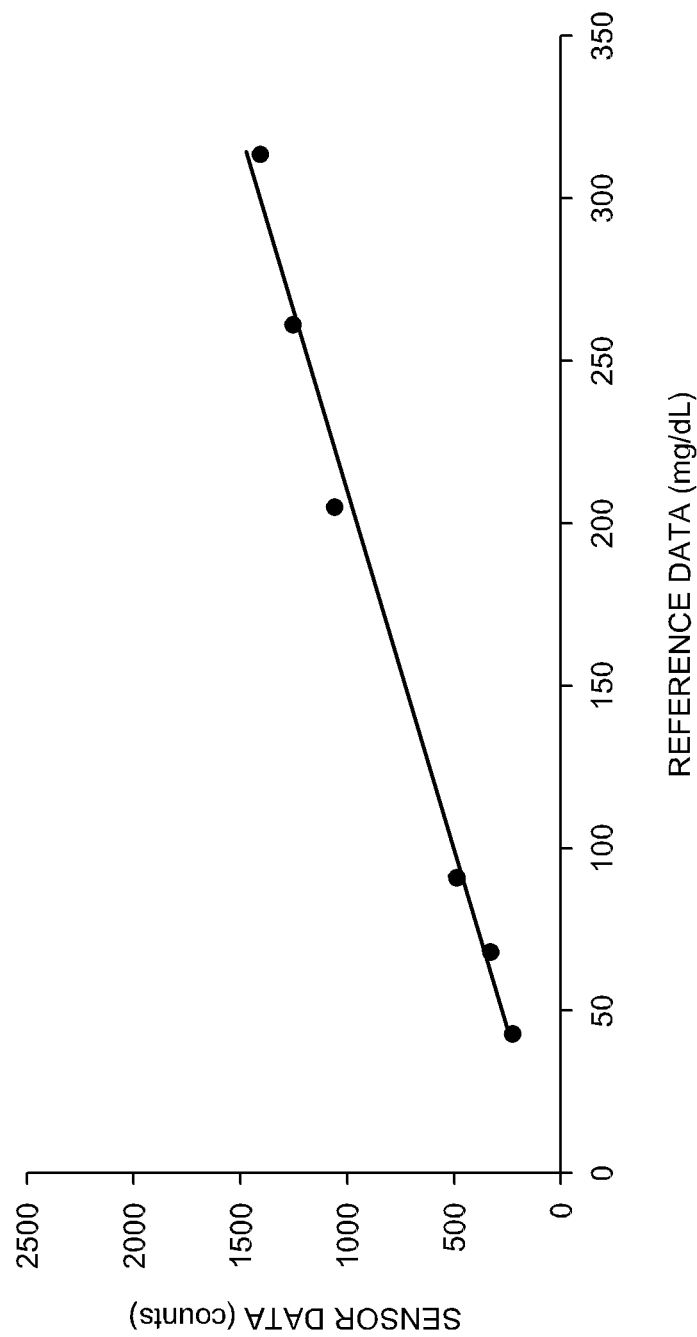
FIGS. 12A and 12B are graphs that illustrate an evaluation of the quality of calibration based on data association in one exemplary embodiment using a correlation coefficient.
Figure 12B:
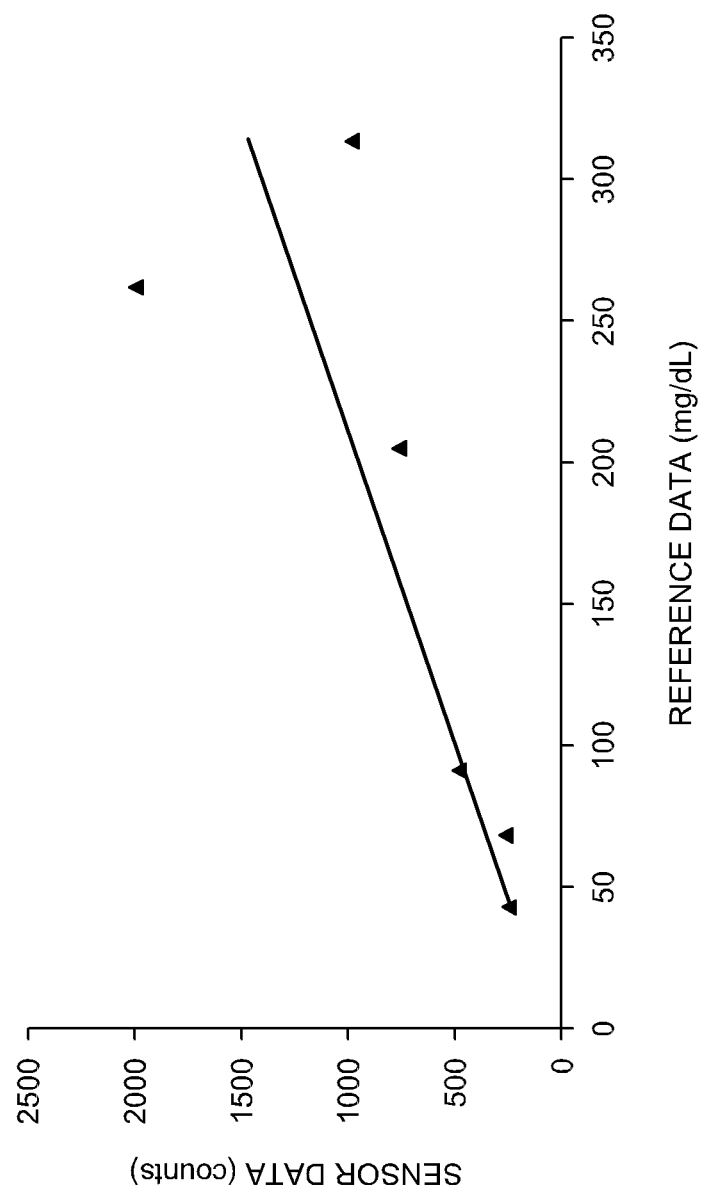

FIGS. 12A and 12B illustrate one exemplary embodiment wherein the accuracy of the conversion function is determined by evaluating the correlation coefficient from linear regression of the calibration set that formed the conversion function. In this exemplary embodiment, a threshold (e.g., 0.79) is set for the R-value obtained from the correlation coefficient.

FIGS. 12A and 12B are graphs that illustrate an evaluation of the quality of calibration based on data association in one exemplary embodiment using a correlation coefficient. Particularly, FIGS. 12A and 12B pictorially illustrate the results of the linear least squares regression performed on a first and a second calibration set (FIGS. 12A and 12B, respectively). The x-axis represents reference analyte data; the y-axis represents sensor data. The graph pictorially illustrates regression that determines the conversion function.

It may be noted that the regression line (and thus the conversion function) formed by the regression of the first calibration set of FIG. 12A is the same as the regression line (and thus the conversion function) formed by the regression of the second calibration set of FIG. 12B. However, the correlation of the data in the calibration set to the regression line in FIG. 12A is significantly different than the correlation of the data in the calibration set to the regression line in FIG. 12A. In other words, there is a noticeably greater deviation of the data from the regression line in FIG. 12B than the deviation of the data from the regression line in FIG. 12A.

In order to quantify this difference in correlation, an R-value may be used to summarize the residuals (e.g., root mean square deviations) of the data when fitted to a straight line via least squares method, in this exemplary embodiment. R-value may be calculated according to the following equation:

$$R = \frac{\sum_i (x_i - \bar{x})(y_i - \bar{y})}{\sqrt{\sum_i (x_i - x)^2} \sqrt{\sum_i (y_i - y)^2}}$$

In the above equation: i is an index (1 to n), x is a reference analyte value, y is a sensor analyte value, $\bar{x}$ is an average of 1/n reference analyte values, and $\bar{y}$ is an average of 1/n sensor analyte values.

In the exemplary calibration set shown in FIG. 12A, the calculated R-value is about 0.99, which may also be expressed as the correlation coefficient of regression. Accordingly, the calibration exhibits sufficient data association (and thus insufficient quality) because it falls above the 0.79 threshold set in this exemplary embodiment.

In the exemplary calibration set shown in FIG. 12B, the calculated R-value is about 0.77, which may also be expressed as the correlation coefficient of regression. Accordingly, the calibration exhibits insufficient data association (and thus insufficient quality) because it falls below the 0.79 threshold set in this exemplary embodiment.

Reference is again made to FIG. 11, at block 118, the interface control module, also referred to as the fail-safe module, controls the user interface based upon the quality of the calibration. If the calibration is exhibits sufficient quality, then the user interface may function as normal; that is providing output for the user such as described in more detail with reference to FIG. 6.

If however the calibration is not deemed sufficient in quality, then fail-safe module 118 begins the initial stages of fail-safe mode, which are described in more detail with reference to FIG. 8. In some embodiments, the initial stages of fail-safe mode include altering the user interface so that estimated sensor data is not displayed to the user. In some embodiments, the initial stages of fail-safe mode also include prompting the user to provide an updated reference analyte value. The updated analyte value is then processed as described above and the updated conversion function that results from the repeated reference analyte test, if any, is evaluated for statistical accuracy.

If the results of the updated evaluation again exhibit insufficient quality, then the fail-safe module alters user interface to reflect full fail-safe mode, which is described in more detail with reference to FIG. 8. If however the results of the updated evaluation exhibit sufficient quality, then the first reference analyte value is discarded, and the repeated reference analyte value is accepted and the process continues as described herein.

It may be noted that the initial stages of fail-safe mode and full fail safe mode may be similar to that described with reference to FIG. 8, including user interface control for example. Additionally, it is contemplated herein that a variety of difference modes between initial and full fail-safe mode may be provided depending on the relative quality of the calibration. In other words, the confidence level of the calibration quality may control a plurality of different user interface screens providing error bars, ±values, and the like. Similar screens may be implements in the clinical acceptability embodiments described with reference to FIG. 8.

The above description discloses several methods and materials of the disclosed invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention as embodied in the attached claims. All patents, applications, and other references cited herein are hereby incorporated by reference in their entirety.

What is claimed is:

1. A method for evaluating a quality of a calibration of an analyte sensor, the method comprising:
receiving sensor data from an analyte sensor during a time period of continuous analyte sensing of a host, including one or more sensor data points;
receiving reference data during the time period of continuous analyte sensing of the host, including one or more reference data points;
providing one or more matched data pairs by matching a reference data point to a substantially time corresponding sensor data point;
forming a calibration set including a plurality of matched data pairs;

evaluating a quality of the calibration set, during the time period of continuous analyte sensing of the host, based on a statistical association of the calibration set and a clinical association of the one or more matched data pairs, wherein the statistical association comprises a statistical analysis of the plurality of matched data pairs' correlation to or deviation from a curve;

modifying the calibration set in response to the statistical association not meeting a criterion or the clinical association not meeting a criterion; and processing the sensor data in response to the statistical association meeting a criterion and the clinical association meeting a criterion.

2. The method of claim 1, wherein receiving sensor data comprises receiving sensor data that has been smoothed.

3. The method of claim 1, wherein receiving sensor data comprises smoothing the sensor data.

4. The method of claim 1, wherein the sensor data is recursively filtered.

5. The method of claim 1, wherein receiving sensor data comprises receiving the sensor data from a substantially continuous glucose sensor.

6. The method of claim 1, wherein receiving reference data comprises receiving reference data from an in vitro blood glucose test.

7. The method of claim 1, wherein receiving reference data comprises downloading reference data via a wireless connection.

8. The method of claim 1, wherein receiving reference data comprises receiving within a receiver an internal communication from a reference analyte monitor integral with the receiver.

9. The method of claim 1, wherein the clinical association is based at least in part on an analysis using a clinical cost function.

10. The method of claim 9, wherein the clinical cost function comprises a Clarke Error Grid, a Consensus Grid or a mean absolute relative difference.

11. The method of claim 1, wherein the statistical analysis uses a statistical cost function.

12. The method of claim 11, wherein the statistical cost function comprises linear regression, non-linear regression, rank correlation, least mean square fit, or mean absolute deviation.

13. The method of claim 1, wherein processing the sensor data comprises calibrating the sensor data.

14. The method of claim 1, wherein processing the sensor data comprises displaying the sensor data.

15. The method of claim 1, further comprising requesting additional reference data in response to the statistical association not meeting a criterion or the clinical association not meeting a criterion.

16. The method of claim 15, wherein modifying the calibration set comprises adding a matched data pair to the calibration set based on the additional received reference data.

17. The method of claim 1, wherein modifying the calibration set comprises removing a most discordant or oldest matched data pair in response to the statistical association not meeting a criterion or the clinical association not meeting a criterion.

18. A computer system for evaluating a quality of a calibration of an analyte sensor, the system comprising:

a sensor data receiving module configured to receive, during a time period of continuous analyte sensing of a host, a data stream comprising one or more sensor data points;

a reference data receiving module configured to receive, during the time period of continuous analyte sensing of the host, reference data, including one or more reference data points;

a data matching module configured to form one or more matched data pairs by matching one or more reference data points to one or more substantially time corresponding sensor data points;

a calibration set module configured to form a calibration set including a plurality of matched data pairs;

an evaluation module configured to evaluate, during the time period of continuous analyte sensing of the host, a quality of the calibration set based on a statistical association of the calibration set and a clinical association of the one or more matched data pairs, wherein the calibration set is modified in response to the statistical association not meeting a criterion or the clinical association not meeting a criterion, wherein the statistical association comprises a statistical analysis of the plurality of matched data pairs' correlation to or deviation from a curve; and a processor module configured to process the sensor data in response to the statistical association meeting a criterion and the clinical association meeting a criterion.

19. The computer system of claim 18, wherein the reference data receiving module is configured to receive sensor data that has been smoothed.

20. The computer system of claim 18, wherein the reference data receiving module is configured to smooth the sensor data.

21. The computer system of claim 18, wherein the sensor data is recursively filtered.

22. The computer system of claim 18, wherein the reference data receiving module is configured to receive the sensor data from a substantially continuous glucose sensor.

23. The computer system of claim 18, wherein the reference data receiving module is configured to receive the reference data from an in vitro blood glucose test.

24. The computer system of claim 18, wherein the reference data receiving module is configured to download the reference data via a wireless connection.

25. The computer system of claim 18, wherein reference data receiving module is configured to receive within a receiver an internal communication from a reference analyte monitor integral with the receiver.

26. The computer system of claim 18, wherein the clinical association is based at least in part on an analysis using a clinical cost function.

27. The computer system of claim 26, wherein the clinical cost function comprises a Clarke Error Grid, a Consensus Grid or a mean absolute relative difference.

28. The computer system of claim 18, wherein the statistical analysis uses a statistical cost function.

29. The computer system of claim 28, wherein the statistical cost function comprises linear regression, non-linear regression, rank correlation, least mean square fit, or mean absolute deviation.

30. The computer system of claim 18, wherein the processor module is configured to calibrate the sensor data in response to the statistical association meeting a criterion and the clinical association meeting a criterion.

31. The system of claim 18, wherein the processor module is configured to display the sensor data in response to the statistical association meeting a criterion and the clinical association meeting a criterion.

32. The system of claim 18, wherein the evaluation module is configured to request additional reference data in response to the statistical association not meeting a criterion or the clinical association not meeting a criterion.

33. The system of claim 32, wherein the evaluation module or the calibration set module is configured to add a matched data pair to the calibration set based on the additional received reference data in response to the statistical association not meeting a criterion or the clinical association not meeting a criterion.

34. The system of claim 18, wherein the calibration set module is modified to remove a most discordant or oldest matched data pair in response to the statistical association not meeting a criterion or the clinical association not meeting a criterion.

\* \* \* \* \*

UNITED STATES PATENT AND TRADEMARK OFFICE
CERTIFICATE OF CORRECTION

PATENT NO. : 8,774,888 B2
APPLICATION NO. : 12/690792
DATED : July 8, 2014
INVENTOR(S) : Apurv Ullas Kamath et al.

It is certified that error appears in the above-identified patent and that said Letters Patent is hereby corrected as shown below:

On the Title Page

In column 2 (page 6, item 56) at line 43, Under Other Publications, change "systme" to --system--.

In column 1 (page 7, item 56) at line 32, Under Other Publications, change "Filder" to --Filter--.

In column 1 (page 7, item 56) at line 43, Under Other Publications, change "Respons(es)" to --Response(s)--.

In column 2 (page 7, item 56) at line 11, Under Other Publications, change "hypoglycaemic" to --hypoglycemic--.

In column 2 (page 7, item 56) at line 37, Under Other Publications, change "Thechnol." to --Technol.--.

In column 2 (page 7, item 56) at line 42, Under Other Publications, change "Senso" to --Sensor--.

In column 1 (page 8, item 56) at line 59, Under Other Publications, change "Potentially-implntable," to --Potentially-implantable,--.

In column 1 (page 8, item 56) at line 64, Under Other Publications, change "reliablity" to --reliability--.

In column 2 (page 8, item 56) at line 6, Under Other Publications, change "Enzymlology," to --Enzymology,--.

In column 2 (page 8, item 56) at line 17, Under Other Publications, change "systme" to --system--.

In column 2 (page 8, item 56) at line 22, Under Other Publications, change "artifical" to --artificial--.

Signed and Sealed this
Twenty-fourth Day of February, 2015

Michelle K. Lee
*Deputy Director of the United States Patent and Trademark Office*

In column 2 (page 8, item 56) at line 40, Under Other Publications, change "your and your" to --you and your--.

In column 2 (page 8, item 56) at line 53, Under Other Publications, change "dynamcs" to --dynamics--.

In column 2 (page 8, item 56) at line 56, Under Other Publications, change "glocuse" to --glucose--.

In column 2 (page 8, item 56) at line 57, Under Other Publications, change "Diabetese" to --Diabetes--.

In column 2 (page 8, item 56) at line 70, Under Other Publications, change "Hypoglycaemia-warning" to --Hypoglycemia-warning--.

In column 1 (page 9, item 56) at line 13, Under Other Publications, change "Thechnol." to --Technol.--.

In column 1 (page 9, item 56) at line 18, Under Other Publications, change "Diabetese" to --Diabetes--.

In column 1 (page 9, item 56) at line 40, Under Other Publications, change "inactiviation" to --inactivation--.

In column 1 (page 10, item 56) at line 26, Under Other Publications, change "activitiy," to --activity,--.

In column 1 (page 10, item 56) at line 43, Under Other Publications, change "Biosensors& Beioelectronics," to --Biosensors & Bioelectronics,--.

In column 1 (page 10, item 56) at line 44, Under Other Publications, change "glocuse" to --glucose--.

In column 1 (page 10, item 56) at line 55, Under Other Publications, change "valication" to --validation--.

In column 1 (page 10, item 56) at line 56, Under Other Publications, change "glucose-iunsulin interaaction in tyhpe" to --glucose-insulin interaction in type--.

In column 2 (page 10, item 56) at line 4, Under Other Publications, change "Electronanalysis" to --Electroanalysis--.

In column 2 (page 10, item 56) at line 30, Under Other Publications, change "artifical" to --artificial--.

In column 2 (page 10, item 56) at line 44, Under Other Publications, change "amperometeric" to --amperometric--.

In column 2 (page 10, item 56) at line 51, Under Other Publications, change "Thechnol." to --Technol.--.

CERTIFICATE OF CORRECTION (continued)
U.S. Pat. No. 8,774,888 B2

In column 1 (page 11, item 56) at line 25, Under Other Publications, change "termistor" to --thermistor--.

In column 1 (page 11, item 56) at line 26, Under Other Publications, change "metobolites," to --metabolites,--.

In column 1 (page 11, item 56) at line 28, Under Other Publications, change "cholesteral and cholesteral" to --cholesterol and cholesterol--.

In column 1 (page 11, item 56) at line 32, Under Other Publications, change "Apllied" to --Applied--.

In column 2 (page 11, item 56) at line 1, Under Other Publications, change "Phillps." to --Phillips.--.

In column 2 (page 11, item 56) at line 60, Under Other Publications, change "Subcutaenous" to --Subcutaneous--.

In column 1 (page 12, item 56) at line 2, Under Other Publications, change "assitance" to --assistance--.

In column 1 (page 12, item 56) at line 3, Under Other Publications, change "Thechnol." to --Technol.--.

In column 1 (page 12, item 56) at line 14, Under Other Publications, change "Membran," to --Membrane,--.

In column 1 (page 12, item 56) at line 37, Under Other Publications, change "Aced" to --Acad--.

In column 1 (page 12, item 56) at line 57, Under Other Publications, change "pancrease" to --pancreas--.

In column 2 (page 12, item 56) at line 9, Under Other Publications, change "Thechnol." to --Technol.--.

In column 2 (page 12, item 56) at line 41, Under Other Publications, change "Membrance" to --Membrane--.

In column 2 (page 12, item 56) at line 49, Under Other Publications, change "cholesteral" to --cholesterol--.

In column 1 (page 13, item 56) at line 8, Under Other Publications, change "Deabetes" to --Diabetes--.

In column 1 (page 13, item 56) at line 41, Under Other Publications, change "Tranducers" to --Transducers--.

In the Specification

In column 20 at line 6, Change "andrenostenedione;" to --androstenedione;--.

In column 20 at line 8, Change "camosinase;" to --carnosinase;--.

In column 20 at line 20, Change "diptheria/" to --diphtheria/--.

In column 20 at line 27, Change "perioxidase;" to --peroxidase;--.

In column 20 at line 40, Change "duodenalisa," to --duodenalis,--.

In column 20 at line 48, Change "Trepenoma pallidium," to --Treponema pallidum,--.

In column 20 at line 49, Change "stomatis" to --stomatitis--.

In column 21 at line 2, Change "(barbituates," to --(barbiturates,--.

In column 23 at line 3, Change "the a" to --the--.

In column 23 at line 47, Change "and or" to --and/or--.

In column 23 at line 63, Change "(e.g." to --(e.g.,--.

In column 24 at line 13, Change "(e.g." to --(e.g.,--.

In column 24 at lines 14-15, Change "by product," to --byproduct,--.

In column 29 at line 49, Change "corn" to --com--.

In column 29 at line 49, Change "corn" to --com--.

In column 29 at line 51, Change "corn" to --com--.

In column 29 at line 56, Change "corn" to --com--.

In column 29 at line 61, Change "corn" to --com--.

In column 29 at line 63, Change "corn" to --com--.

In column 31 at line 59, Change "FIG. 10" to --FIG. 10.--.